(12) United States Patent  
Quake

(10) Patent No.: US 7,981,604 B2
(45) Date of Patent: Jul. 19, 2011

(54) METHODS AND KITS FOR ANALYZING POLYNUCLEOTIDE SEQUENCES

(75) Inventor: Stephen Quake, Stanford, CA (US)

(73) Assignee: California Institute of Technology, Pasadena, CA (US)

( * ) Notice: Subject to any disclaimer, the term of this patent is extended or adjusted under 35 U.S.C. 154(b) by 299 days.

(21) Appl. No.: 11/054,243

(22) Filed: Feb. 9, 2005

(65) Prior Publication Data

US 2006/0019267 A1     Jan. 26, 2006

Related U.S. Application Data

(60) Provisional application No. 60/546,277, filed on Feb. 19, 2004, provisional application No. 60/547,611, filed on Feb. 24, 2004.

(51) Int. Cl.
*C12Q 1/68* (2006.01)
*C07H 21/02* (2006.01)
*C07H 21/04* (2006.01)

(52) U.S. Cl. ............................. 435/6; 536/23.1; 536/24.3
(58) Field of Classification Search ..... 435/6; 536/23.1, 536/24.3
See application file for complete search history.

(56) References Cited

U.S. PATENT DOCUMENTS

| | | |
|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Kosler et al. |
| 4,739,044 A | 4/1988 | Slabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin et al. |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A * | 4/1994 | Cheeseman ....................... 435/6 |
| 5,304,487 A | 4/1994 | Wilding et al. |
| 5,306,403 A | 4/1994 | Vo-Dinh |
| 5,320,952 A * | 6/1994 | Deutch et al. ................ 435/69.1 |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Jett et al. |
| 5,405,783 A | 4/1995 | Pirrung et al. |

(Continued)

FOREIGN PATENT DOCUMENTS

DE     10256898 A1     9/2004

(Continued)

OTHER PUBLICATIONS

Hacia et al., Detection of heterozygous mutations in BRAC1 using high density oligonucleotide arrays and two-color fluorescence analysis. Nature Genetics 14(4) :441-447 (1996).*
Kurg et al., Arrayed primer extension: Solid-phase four-color DNA Resequencing and mutation detection technology. Genetic Testing 4 (1) : 1-7 (2000).*
Ansorge et al., High-throughput automated DNA sequencing facility with fluorescent labels at the European Molecular Biology Laboratory. Electrophoresis 13 : 616-619 (1992).*

(Continued)

*Primary Examiner* — Ethan C Whisenant
(74) *Attorney, Agent, or Firm* — Thomas Meyers; Adam Schoen; Brown Rudnick LLP

(57) ABSTRACT

The present invention features methods for analyzing a sequence of a target polynucleotide by detecting incorporation of a nucleotide into its complementary strand, where the polynucleotides may be bound at high density and at single molecule resolution. The invention also features labeling moieties and blocking moieties, which facilitate chain termination or choking. Certain aspects provide for temporal detection of the incorporations; some allow for asynchronous analysis of a plurality of target polynucleotides and the use of short sequencing cycles. Surface chemistry aspects of the sequencing methods are also provided. The method may also be used in kits, said kits designed to carry out and facilitate the methods provided herein.

22 Claims, 26 Drawing Sheets

(3 of 26 Drawing Sheet(s) Filed in Color)

U.S. PATENT DOCUMENTS

| | | |
|---|---|---|
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,547,859 A | 8/1996 | Goodman et al. |
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | Fuller |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz et al. |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,763,594 A | 6/1998 | Hiatt et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,808,045 A | 9/1998 | Hiatt et al. |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Afromowitz et al. |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster et al. |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |
| 6,049,380 A | 4/2000 | Goodwin et al. |
| 6,051,380 A | 4/2000 | Sosnowski et al. |
| 6,066,454 A | 5/2000 | Lipshutz et al. |
| 6,071,394 A | 6/2000 | Cheng et al. |
| 6,077,664 A | 6/2000 | Slater et al. |
| 6,077,674 A | 6/2000 | Schleifer et al. |
| 6,087,095 A | 7/2000 | Rosenthal et al. |
| 6,087,099 A | 7/2000 | Gupte et al. |
| 6,094,274 A | 7/2000 | Yokoi |
| 6,107,032 A | 8/2000 | Kilger et al. |
| 6,107,044 A | 8/2000 | Nikiforov |
| 6,107,061 A | 8/2000 | Johnson |
| 6,132,580 A | 10/2000 | Mathies et al. |
| 6,133,436 A | 10/2000 | Koster et al. |
| 6,136,212 A | 10/2000 | Mastrangelo et al. |
| 6,136,962 A | 10/2000 | Shi et al. |
| 6,140,053 A | 10/2000 | Koster |
| 6,140,494 A | 10/2000 | Hamilton et al. |
| 6,141,096 A | 10/2000 | Stern et al. |
| 6,143,151 A | 11/2000 | Middendorf et al. |
| 6,147,205 A | 11/2000 | McGall et al. |
| 6,156,501 A | 12/2000 | McGall et al. |
| 6,165,694 A | 12/2000 | Liu |
| 6,177,249 B1 | 1/2001 | Kwok et al. |
| 6,197,506 B1 | 3/2001 | Fodor et al. |
| 6,197,595 B1 | 3/2001 | Anderson et al. |
| 6,207,381 B1 | 3/2001 | Larsson et al. |
| 6,207,960 B1 | 3/2001 | Stern |
| 6,210,896 B1 | 4/2001 | Chan |
| 6,214,246 B1 | 4/2001 | Craighead |
| 6,214,987 B1 | 4/2001 | Hiatt et al. |
| 6,221,592 B1 | 4/2001 | Schwartz et al. |
| 6,221,654 B1 | 4/2001 | Quake et al. |
| 6,225,052 B1 | 5/2001 | Batz et al. |
| 6,225,062 B1 | 5/2001 | Dunn et al. |
| 6,225,092 B1 | 5/2001 | Kilger et al. |
| 6,225,109 B1 | 5/2001 | Juncosa et al. |
| 6,225,567 B1 | 5/2001 | Kester |
| 6,225,625 B1 | 5/2001 | Pirrung et al. |
| 6,228,593 B1 | 5/2001 | Lipshutz et al. |
| 6,232,075 B1 | 5/2001 | Williams |
| 6,232,103 B1 | 5/2001 | Short |
| 6,235,465 B1 | 5/2001 | Kolberg et al. |
| 6,235,473 B1 | 5/2001 | Friedman et al. |
| 6,242,180 B1 | 6/2001 | Chee |
| 6,242,528 B1 | 6/2001 | Clark et al. |
| 6,245,506 B1 | 6/2001 | Laugharn, Jr. et al. |
| 6,245,507 B1 | 6/2001 | Bogdanov |
| 6,245,518 B1 | 6/2001 | Baier |

| | | |
|---|---|---|
| 6,251,610 B1 | 6/2001 | Gupte et al. |
| 6,255,083 B1 | 7/2001 | Williams |
| 6,255,475 B1 | 7/2001 | Kwiatkowski |
| 6,258,533 B1 | 7/2001 | Jones |
| 6,261,775 B1 | 7/2001 | Bastian et al. |
| 6,261,776 B1 | 7/2001 | Pirrung et al. |
| 6,261,848 B1 | 7/2001 | Anderson et al. |
| 6,262,838 B1 | 7/2001 | Montagu |
| 6,263,286 B1 | 7/2001 | Gilmanshin et al. |
| 6,268,152 B1 | 7/2001 | Fodor et al. |
| 6,268,219 B1 | 7/2001 | Mcbride et al. |
| 6,269,846 B1 | 8/2001 | Overbeck et al. |
| 6,270,644 B1 | 8/2001 | Mathies et al. |
| 6,270,961 B1 | 8/2001 | Drmanac |
| 6,274,320 B1 | 8/2001 | Rothberg et al. |
| 6,274,351 B1 | 8/2001 | Peponnet |
| 6,277,604 B1 | 8/2001 | Peponnet |
| 6,280,954 B1 | 8/2001 | Ulfendahl |
| 6,284,460 B1 | 9/2001 | Fodor et al. |
| 6,287,821 B1 | 9/2001 | Shi et al. |
| 6,294,336 B1 | 9/2001 | Boyce-Jacino et al. |
| 6,294,337 B1 | 9/2001 | Hayashizaki |
| 6,306,607 B2 | 10/2001 | Williams |
| 6,309,601 B1 | 10/2001 | Juncosa et al. |
| 6,309,701 B1 | 10/2001 | Barbera-Guillem |
| 6,309,824 B1 | 10/2001 | Drmanac |
| 6,309,836 B1 | 10/2001 | Kwiatkowski |
| 6,309,886 B1 | 10/2001 | Ambrose et al. |
| 6,310,189 B1 | 10/2001 | Fodor et al. |
| 6,312,893 B1 | 11/2001 | Van Ness et al. |
| 6,316,191 B1 | 11/2001 | Drmanac et al. |
| 6,322,968 B1 | 11/2001 | Head et al. |
| 6,331,439 B1 | 12/2001 | Cherukuri et al. |
| 6,333,183 B1 | 12/2001 | Evans et al. |
| 6,335,824 B1 | 1/2002 | Overbeck |
| 6,337,185 B1 | 1/2002 | Asp et al. |
| 6,337,188 B1 | 1/2002 | Head et al. |
| 6,342,326 B1 | 1/2002 | Milton |
| 6,344,325 B1 | 2/2002 | Quake et al. |
| 6,346,379 B1 | 2/2002 | Gelfand et al. |
| 6,346,413 B1 | 2/2002 | Fodor et al. |
| 6,355,420 B1 | 3/2002 | Chan |
| 6,355,432 B1 | 3/2002 | Fodor et al. |
| 6,361,671 B1 | 3/2002 | Mathies et al. |
| 6,361,937 B1 | 3/2002 | Stryer |
| 6,368,562 B1 | 4/2002 | Yao |
| 6,368,699 B1 | 4/2002 | Gilbert et al. |
| 6,383,749 B2 | 5/2002 | Bochkariov et al. |
| 6,387,626 B1 | 5/2002 | Shi et al. |
| 6,395,232 B1 | 5/2002 | McBride |
| 6,395,559 B1 | 5/2002 | Swenson |
| 6,397,150 B1 | 5/2002 | Izmailov |
| 6,399,364 B1 | 6/2002 | Reeve et al. |
| 6,401,267 B1 | 6/2002 | Drmanac |
| 6,403,311 B1 | 6/2002 | Chan |
| 6,403,315 B1 | 6/2002 | Drmanac |
| 6,403,317 B1 | 6/2002 | Anderson |
| 6,403,320 B1 | 6/2002 | Read et al. |
| 6,403,957 B1 | 6/2002 | Fodor et al. |
| 6,404,907 B1 | 6/2002 | Gilchrist et al. |
| 6,406,893 B1 | 6/2002 | Knapp et al. |
| 6,407,858 B1 | 6/2002 | Montagu |
| 6,408,878 B2 | 6/2002 | Unger et al. |
| 6,416,952 B1 | 7/2002 | Pirrung et al. |
| 6,420,169 B1 | 7/2002 | Read et al. |
| 6,423,273 B1 | 7/2002 | O'Mara |
| 6,432,634 B1 | 8/2002 | Digby et al. |
| 6,436,641 B1 | 8/2002 | Izmailov |
| 6,436,646 B1 | 8/2002 | Nikiforov |
| 6,440,664 B1 | 8/2002 | Digby et al. |
| 6,440,722 B1 | 8/2002 | Knapp et al. |
| 6,444,106 B1 | 9/2002 | Mcbride et al. |
| 6,444,173 B1 | 9/2002 | Sjursen et al. |
| 6,444,424 B1 | 9/2002 | Chatterjee et al. |
| 6,444,461 B1 | 9/2002 | Knapp et al. |
| 6,447,724 B1 | 9/2002 | Jensen et al. |
| 6,448,090 B1 | 9/2002 | McBride |
| 6,451,536 B1 | 9/2002 | Fodor et al. |
| 6,479,267 B1 | 11/2002 | Davis et al. |
| 6,485,690 B1 | 11/2002 | Pfost et al. |
| 6,485,909 B1 | 11/2002 | Hong et al. |
| 6,485,944 B1 | 11/2002 | Church et al. |
| 6,495,363 B2 | 12/2002 | Bogdanov |
| 6,506,560 B1 | 1/2003 | Hughes et al. |
| 6,511,803 B1 | 1/2003 | Church et al. |
| 6,514,706 B1 | 2/2003 | Von Kalle et al. |
| 6,521,428 B1 | 2/2003 | Senapathy |
| 6,524,829 B1 | 2/2003 | Seeger |
| 6,528,258 B1 | 3/2003 | Russell |
| 6,528,288 B1 | 3/2003 | Senapathy |
| 6,537,755 B1 | 3/2003 | Drmanac |
| 6,537,757 B1 | 3/2003 | Langmore et al. |
| 6,546,340 B2 | 4/2003 | Lipshutz et al. |
| 6,551,784 B2 | 4/2003 | Fodor et al. |
| 6,551,817 B2 | 4/2003 | Besemer et al. |
| 6,554,987 B1 | 4/2003 | Gilchrist et al. |
| 6,555,349 B1 | 4/2003 | O'Donnell |
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehleger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 * | 9/2003 | Parce et al. ............... 435/6 |
| 6,623,928 B2 | 9/2003 | Van Ness et al. |
| 6,627,748 B1 | 9/2003 | Ju et al. |
| 6,632,655 B1 | 10/2003 | Mehta et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham |
| 6,911,345 B2 | 6/2005 | Quake et al. |
| 7,018,794 B2 * | 3/2006 | Berka et al. ............... 435/6 |
| 7,033,764 B2 | 4/2006 | Korlach et al. |
| 7,052,847 B2 * | 5/2006 | Korlach et al. ............... 435/6 |
| 7,169,560 B2 * | 1/2007 | Lapidus et al. ............... 435/6 |
| 2001/0024790 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 * | 8/2002 | Ju et al. ............... 435/6 |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0137046 A1 | 9/2002 | Koster |
| 2002/0137052 A1 | 9/2002 | Bridgham et al. |
| 2002/0137062 A1 | 9/2002 | Williams et al. |
| 2002/0138205 A1 | 9/2002 | Miller et al. |
| 2002/0142329 A1 | 10/2002 | Matray et al. |

| | | | | | |
|---|---|---|---|---|---|
| 2002/0142333 A1 | 10/2002 | Gelfand et al. | EP | 0579997 A1 | 1/1994 |
| 2002/0146704 A1 | 10/2002 | Head et al. | EP | 0703364 A1 | 3/1996 |
| 2002/0146726 A1 | 10/2002 | Matray et al. | EP | 0706004 A2 | 4/1996 |
| 2002/0150903 A1 | 10/2002 | Koster | EP | 0779436 A2 | 6/1997 |
| 2002/0150938 A1 | 10/2002 | Kneipp et al. | EP | 0845603 A1 | 6/1998 |
| 2002/0164629 A1* | 11/2002 | Quake et al. ............. 435/6 | EP | 0932700 B1 | 8/1999 |
| 2002/0168642 A1 | 11/2002 | Drukier | EP | 0946752 B1 | 10/1999 |
| 2002/0168678 A1 | 11/2002 | Williams et al. | EP | 0955085 A2 | 11/1999 |
| 2002/0172948 A1 | 11/2002 | Perlin | EP | 0999055 A2 | 5/2000 |
| 2002/0177129 A1 | 11/2002 | Paabo et al. | EP | 0706004 B1 | 8/2003 |
| 2002/0182601 A1 | 12/2002 | Sampson et al. | GB | 2155152 A | 9/1985 |
| 2002/0192661 A1 | 12/2002 | Paabo et al. | GB | 2308460 A | 6/1997 |
| 2002/0192662 A1 | 12/2002 | Boyce-Jacino et al. | GB | 2400518 A | 10/2004 |
| 2002/0192691 A1 | 12/2002 | Drmanac | SE | 9500589 | 2/1995 |
| 2002/0197618 A1 | 12/2002 | Sampson | WO | 89/03432 A1 | 4/1989 |
| 2003/0003272 A1 | 1/2003 | Laguitton | WO | 89/09283 A1 | 10/1989 |
| 2003/0003498 A1 | 1/2003 | Digby et al. | WO | 90/13666 A1 | 11/1990 |
| 2003/0008285 A1 | 1/2003 | Fischer | WO | 90/15070 A1 | 12/1990 |
| 2003/0008413 A1 | 1/2003 | Kim et al. | WO | 91/06678 A1 | 5/1991 |
| 2003/0017461 A1 | 1/2003 | Singh et al. | WO | 92/10092 A1 | 6/1992 |
| 2003/0022207 A1 | 1/2003 | Balasubramanian et al. | WO | 92/10587 A1 | 6/1992 |
| 2003/0027140 A1 | 2/2003 | Ju et al. | WO | 93/05183 A1 | 3/1993 |
| 2003/0036080 A1 | 2/2003 | Jensen et al. | WO | 93/06121 A1 | 4/1993 |
| 2003/0044778 A1 | 3/2003 | Goelet et al. | WO | 93/21340 A1 | 10/1993 |
| 2003/0044779 A1 | 3/2003 | Goelet et al. | WO | 95/12608 A1 | 5/1995 |
| 2003/0044781 A1 | 3/2003 | Korlach et al. | WO | 95/27080 A1 | 10/1995 |
| 2003/0044816 A1 | 3/2003 | Denison et al. | WO | 96/04547 A1 | 2/1996 |
| 2003/0054181 A1 | 3/2003 | Swerdlow et al. | WO | 96/12014 A1 | 4/1996 |
| 2003/0054361 A1 | 3/2003 | Heller | WO | 96/12039 A1 | 4/1996 |
| 2003/0058440 A1 | 3/2003 | Scott et al. | WO | 96/27025 A1 | 9/1996 |
| 2003/0058799 A1 | 3/2003 | Yamakawa et al. | WO | 97/02488 A1 | 1/1997 |
| 2003/0059778 A1 | 3/2003 | Berlin et al. | WO | 97/22076 A1 | 6/1997 |
| 2003/0060431 A1 | 3/2003 | Simmonds et al. | WO | 97/23650 A2 | 6/1997 |
| 2003/0064366 A1 | 4/2003 | Hardin et al. | WO | 97/37041 A2 | 10/1997 |
| 2003/0064398 A1 | 4/2003 | Barnes | WO | 97/39150 A1 | 10/1997 |
| 2003/0064483 A1 | 4/2003 | Shaw et al. | WO | 97/40184 A1 | 10/1997 |
| 2003/0087237 A1 | 5/2003 | Hong et al. | WO | 97/41258 A1 | 11/1997 |
| 2003/0087300 A1 | 5/2003 | Knapp et al. | WO | 97/41259 A1 | 11/1997 |
| 2003/0092005 A1 | 5/2003 | Levene et al. | WO | 97/42348 A1 | 11/1997 |
| 2003/0092007 A1 | 5/2003 | Gibbs et al. | WO | 98/00708 A1 | 1/1998 |
| 2003/0096258 A1 | 5/2003 | Fu et al. | WO | 98/02575 A1 | 1/1998 |
| 2003/0100006 A1 | 5/2003 | Senapathy | WO | 98/03684 A1 | 1/1998 |
| 2003/0104437 A1 | 6/2003 | Barnes et al. | WO | 98/07069 A1 | 2/1998 |
| 2003/0104466 A1 | 6/2003 | Knapp et al. | WO | 98/13523 A1 | 4/1998 |
| 2003/0108867 A1 | 6/2003 | Chee et al. | WO | 98/08978 A1 | 5/1998 |
| 2003/0138809 A1 | 7/2003 | Williams et al. | WO | 98/20019 A1 | 5/1998 |
| 2003/0148344 A1 | 8/2003 | Rothberg et al. | WO | 98/20020 A2 | 5/1998 |
| 2003/0162213 A1 | 8/2003 | Fuller et al. | WO | 98/20166 A2 | 5/1998 |
| 2003/0186227 A1 | 10/2003 | Balasubramanian et al. | WO | 98/21361 A1 | 5/1998 |
| 2003/0186255 A1 | 10/2003 | Williams et al. | WO | 98/27228 A1 | 6/1998 |
| 2003/0190627 A1 | 10/2003 | Zhao et al. | WO | 98/28440 A1 | 7/1998 |
| 2003/0190647 A1 | 10/2003 | Odera | WO | 98/33939 A1 | 8/1998 |
| 2003/0190663 A1 | 10/2003 | Yang et al. | WO | 98/40520 A1 | 9/1998 |
| 2003/0194722 A1 | 10/2003 | Odedra et al. | WO | 98/41650 A2 | 9/1998 |
| 2003/0194740 A1 | 10/2003 | Williams | WO | 98/41657 A1 | 9/1998 |
| 2003/0211486 A1* | 11/2003 | Frudakis ............. 435/6 | WO | 98/44152 A1 | 10/1998 |
| 2003/0215862 A1 | 11/2003 | Parce et al. | WO | 98/45481 A1 | 10/1998 |
| 2004/0009487 A1 | 1/2004 | Kadushin et al. | WO | 98/53300 A2 | 11/1998 |
| 2004/0014096 A1 | 1/2004 | Anderson et al. | WO | 98/54669 A1 | 12/1998 |
| 2004/0029115 A9 | 2/2004 | Dower et al. | WO | 98/55593 A1 | 12/1998 |
| 2004/0038206 A1 | 2/2004 | Zhang et al. | WO | 99/01768 A1 | 1/1999 |
| 2004/0054162 A1 | 3/2004 | Hanna | WO | 99/05221 A1 | 2/1999 |
| 2004/0106110 A1 | 6/2004 | Balasubramanian et al. | WO | 99/05315 A2 | 2/1999 |
| 2004/0126770 A1 | 7/2004 | Kumar et al. | WO | 99/06422 A2 | 2/1999 |
| 2005/0014175 A1 | 1/2005 | Quake et al. | WO | 99/13109 A1 | 3/1999 |
| 2005/0100932 A1* | 5/2005 | Lapidus et al. ............. 435/6 | WO | 99/13110 A1 | 3/1999 |
| 2005/0147992 A1 | 7/2005 | Quake et al. | WO | 99/09616 A1 | 4/1999 |
| 2005/0170367 A1 | 8/2005 | Quake et al. | WO | 99/17093 A1 | 4/1999 |
| 2005/0239085 A1 | 10/2005 | Buzby et al. | WO | 99/19516 A1 | 4/1999 |
| 2006/0134684 A1* | 6/2006 | Freimuth et al. ............. 435/6 | WO | 99/24797 A1 | 5/1999 |
| 2006/0154288 A1* | 7/2006 | Korlach et al. ............. 435/6 | WO | 99/27137 A1 | 6/1999 |
| 2008/0051294 A1* | 2/2008 | Gormley et al. ............. 506/4 | WO | 99/31278 A1 | 6/1999 |
| 2008/0274511 A1* | 11/2008 | Tan et al. ............. 435/91.2 | WO | 99/37810 A1 | 7/1999 |
| 2010/0094563 A1* | 4/2010 | Sorenson ............. 702/20 | WO | 99/39001 A2 | 8/1999 |
| 2010/0216153 A1* | 8/2010 | Lapidus et al. ............. 435/6 | WO | 99/40105 A2 | 8/1999 |
| | | | WO | 99/40223 A1 | 8/1999 |
| | FOREIGN PATENT DOCUMENTS | | WO | 99/41410 A1 | 8/1999 |
| EP | 0223618 A2 | 5/1987 | WO | 99/44045 A1 | 9/1999 |
| EP | 0412883 A1 | 2/1991 | WO | 99/45153 A2 | 9/1999 |

| | | | |
|---|---|---|---|
| WO | 99/47539 A1 | 9/1999 | |
| WO | 99/47706 A1 | 9/1999 | |
| WO | 99/53423 A1 | 10/1999 | |
| WO | 99/57321 A1 | 11/1999 | |
| WO | 99/61888 A2 | 12/1999 | |
| WO | 99/64437 A1 | 12/1999 | |
| WO | 99/64840 A1 | 12/1999 | |
| WO | 99/65938 A2 | 12/1999 | |
| WO | 99/66076 A1 | 12/1999 | |
| WO | 99/66313 A1 | 12/1999 | |
| WO | 00/00637 A2 | 1/2000 | |
| WO | 00/06770 A1 | 2/2000 | |
| WO | 00/09753 A1 | 2/2000 | |
| WO | WO 00/06770 | * 2/2000 | |
| WO | 00/11223 A1 | 3/2000 | |
| WO | 00/17397 A1 | 3/2000 | |
| WO | 00/26935 A2 | 5/2000 | |
| WO | 00/30591 A1 | 6/2000 | |
| WO | 00/34523 A1 | 6/2000 | |
| WO | 00/37680 A1 | 6/2000 | |
| WO | 00/40750 A1 | 7/2000 | |
| WO | 00/40758 A2 | 7/2000 | |
| WO | 00/42223 A1 | 7/2000 | |
| WO | 00/43540 A1 | 7/2000 | |
| WO | 00/43752 A1 | 7/2000 | |
| WO | 00/50642 A1 | 8/2000 | |
| WO | 00/53805 A1 | 9/2000 | |
| WO | 00/53812 A2 | 9/2000 | |
| WO | 00/56937 A2 | 9/2000 | |
| WO | 00/58507 A1 | 10/2000 | |
| WO | 00/58516 A2 | 10/2000 | |
| WO | 00/68410 A1 | 11/2000 | |
| WO | 00/70073 A1 | 11/2000 | |
| WO | 00/71755 A2 | 11/2000 | |
| WO | 00/79007 A1 | 12/2000 | |
| WO | 01/01025 A3 | 1/2001 | |
| WO | 01/16375 A2 | 3/2001 | |
| WO | 01/23610 A2 | 4/2001 | |
| WO | 01/24937 A2 | 4/2001 | |
| WO | 01/25480 A2 | 4/2001 | |
| WO | 01/31055 A2 | 5/2001 | |
| WO | 01/32930 A1 | 5/2001 | |
| WO | 01/38574 A1 | 5/2001 | |
| WO | 01/48184 A2 | 5/2001 | |
| WO | 01/42496 A2 | 6/2001 | |
| WO | 01/57248 A2 | 8/2001 | |
| WO | 01/57249 A1 | 8/2001 | |
| WO | 01/61044 A1 | 8/2001 | |
| WO | 01/64838 A2 | 9/2001 | |
| WO | 01/75154 A2 | 10/2001 | |
| WO | 01/79536 A1 | 10/2001 | |
| WO | 01/85991 A2 | 11/2001 | |
| WO | 01/92284 A1 | 12/2001 | |
| WO | 01/96607 A2 | 12/2001 | |
| WO | 02/00343 A2 | 1/2002 | |
| WO | 02/02584 A1 | 1/2002 | |
| WO | 02/02795 A2 | 1/2002 | |
| WO | 02/02813 A2 | 1/2002 | |
| WO | 02/03305 A2 | 1/2002 | |
| WO | 02/04680 A2 | 1/2002 | |
| WO | 02/20836 A2 | 3/2002 | |
| WO | 02/20837 A2 | 3/2002 | |
| WO | 02/27032 A1 | 4/2002 | |
| WO | 02/29106 A2 | 4/2002 | |
| WO | 02/30486 A3 | 4/2002 | |
| WO | 02/35441 A2 | 5/2002 | |
| WO | 02/36832 A2 | 5/2002 | |
| WO | 02/44414 A2 | 6/2002 | |
| WO | 02/061126 A2 | 8/2002 | |
| WO | 02/061127 A2 | 8/2002 | |
| WO | 02/072779 A2 | 9/2002 | |
| WO | 02/072892 A1 | 9/2002 | |
| WO | 02/077694 A1 | 10/2002 | |
| WO | 02/079519 A1 | 10/2002 | |
| WO | 02/088381 A2 | 11/2002 | |
| WO | 02/088382 A2 | 11/2002 | |
| WO | 02/097113 A2 | 12/2002 | |
| WO | 02/099398 A1 | 12/2002 | |
| WO | 03/002767 A1 | 1/2003 | |
| WO | 03/016565 A2 | 2/2003 | |
| WO | 03/020895 A2 | 3/2003 | |
| WO | 03/020968 A2 | 3/2003 | |
| WO | 03/021010 A2 | 3/2003 | |
| WO | 03/031947 A2 | 4/2003 | |
| WO | 03/044678 A1 | 5/2003 | |
| WO | 03/048178 A2 | 6/2003 | |
| WO | 03/048991 A2 | 6/2003 | |
| WO | 03/062897 A1 | 7/2003 | |
| WO | 03/106642 A2 | 12/2003 | |
| WO | 2004/061119 A2 | 7/2004 | |
| WO | 2004/074503 A2 | 9/2004 | |
| WO | 2005/047523 A2 | 5/2005 | |
| WO | 2005/080605 A2 | 9/2005 | |

OTHER PUBLICATIONS

Henikoff S., Unidirectiomnal Digestion with Exonuclease III in DNA sequence analysis. Methods in Enzymology 155 : 156-165 (1987).*
Adam et al., "Individual genomes targeted in sequencing revolution", *Nature*, vol. 411, p. 402 (May 2001).
Agrawal, S. et al., "Site Specific Functionalization of Oligodeoxynucleotides for Non-Radioactive Labelling", *Tetrahedron Letters*, vol. 31, No. 11, pp. 1543-1546 (1990).
Ambrose, W. et al., "Single Molecule Detection With Total Internal Reflection Excitation: Comparing Signal-toBackground and Total Signals in Different Geometries", *Cytometry*, vol. 36, pp. 224-231 (1999).
Amit, B. et al., "Photosensitive Protecting Groups of Amino Sugars and Their Use in Glycoside Synthesis . . . Derivatives", 1. *Org. Chem.*, 39(2):192-6 (1974).
Arndt-Jovin, B. et al., "Immunofluorescence Localization of Z-DNA in Chromosomes: Quantitation by Scanning Microphotometry and Computer-assisted Image Analysis", 1. *The Journal of Cell Biology*, vol. 101, pp. 1422-1433, (Oct. 1985).
Augustin, M.A., W. Ankenbauer, and B. Angerer, "Progress towards single-molecule sequencing: enzymatic synthesis of nucleotide-specifically labeled DNA." *Journal of Biotechnology*, 8(13): 289-301 (2001).
Axelrod, D., "Cell-Substrate Contacts Illuminated by Total Internal Reflection Fluorescence", 1. *The Journal of Cell Biology*, vol. 89, pp. 141-145, (Apr. 1981).
Axelrod, D. et al., "Total internal reflection fluorescent microscopy", *J Microscopy*, vol. 129, pp. 19-28, (1983).
Bai, X., et al., "Photocleavage of a 2-nitrobenzyl linker bridging a fluorophore to the 5' end of DNA." Proc Natl Acad Sci USA, 2003, vol. 100(2). p. 409-13.
Basche, T. et al., "Single Molecule Optical Detection, Imaging and Spectroscopy", Chs. 2 and 3, Weinheim:VCM, Germany (1997).
Beaucage, S. et al., "Advances in the Synthesis of Oligonucleotides by the Phosphoramidite Approach" *Tetrahedron*, 48:2223-2311 (1992).
Beese, L. et al., "Structure of DNA Polymerase I Klenow Fragment Bound to Duplex DNA", *Science*, 260:352-355 (1993).
Bennett et. al., "Solexa Sequencing chemistry can be applied to different platforms which will have common elements in detection and data processing",*Pharmacogenomics* 5(4), pp. 433-438, (2004).
Biesalski et al., "Preparation and Characterization of a Polyelectrolyte Monolayer Covalently Attached to a Planar Solid Surface", *Macromolecules* 111, 32, 2309-2316. Article was published on the web Mar. 10, 1999.
Black, D.L., "Protein diversity from alternating splicing: A challenge for bioinformatics and post genome biology", *Cell*, 2000. 103(3): p. 367-370.
Blattner, F.R., et al., "The Complete genome sequence of *Escherichia coli* K-12.", *Science*, 277: 1453-74 (1997).
Boles et. al., "High-Resolution Mapping of Carcinogen Binding Sites on DNA", *Biochemistry*, 1986, 25, 3039-3043.
Brakmann, S. and P. Nieckchen, "The large fragment of *Escherichia coli* DNA polymerase I can synthesize DNA exclusively from fluorescently labeled nucleotides." *Chembiochem*, 2(10): 773-777 (2001).
Brakmann et. al, "Optimal Enzymes for Single-Molecule Sequencing", *Current Pharmaceutical Biotechnology*, 5, pp. 119-126 (2004).

Braslavsky, I. et al., "Sequence information can be obtained from single DNA molecules", *PNAS*, vol. 100, No. 7, pp. 3960-3964 (Apr. 2003).

Braslavsky, I. et al., "Objective-type dark-field illumination for scattering from microbeads", *Applied Optics*, vol. 40, No. 31, pp. 5650-5657, (Nov. 2001).

Braslavsky, I. et al., "Single Molecule Measurements of DNA Polymerase Activity: A Step Towards Single Molecule Sequencing", *Biophys. 1. Abstracts*, p. 507A (2002).

Brechtel, R. et al., "Control of the electro osmotic flow by metal-salt-containing buffers", *J Chromatoraphy A*, vol. 716, pp. 97-105, (1995).

Bridgman, A. et al., "An improved method for the synthesis of mercurated dUTP. Enzymatic synthesis of Hg-labelled DNA of high molecular weight suitable for use in an image based DNA sequencing strategy", *DNA Seq.*, vol. 6, No. 4, pp. 199-209 (1996).

Bruggert, J. et al., "Microfabricated tools for nanoscience", *J. Micromech. Microeng.*, 3, pp. 161-167 (1993).

Bryzek, J. etal., "Micromachines on the march", *IEEE Spectrum*, vol. 31, No. 5, pp. 20-31, (1994).

Buchaillot, L. et al., "Silicon Nitride Thin Films Young's Modulus Determination by an Optical Non Destructive Method", *Jpn. J. Appl. Phys.*, vol. 36, pp. L794-L797, (Jun. 1997).

Burghardt, T. et al., "Total Internal Reflection Fluorescence Study of Energy Transfer in Surface-Adsorbed and Dissolved Bovine Serum Albumin", *Biochemistry*, vol. 22, pp. 979-985 (1983).

Burghardt, et al., "Total Internal Reflection/Fluorescence Photobleaching Recovery Study of Serum Albumin Adsorption Dynamics", *Biophys. Journal*, vol. 33, pp. 455-468 (Mar. 1981).

Butler, D. et al., "Draft data leave geneticists with a mountain still to climb", *Nature*, vol. 405, Issue 6782, pp. 984-985 (May 2000).

Canard, B., B. Cardona, and R.S. Sarfati, "Catalytic editing properties of DNA polymerases," *Proc Natl Acad Sci USA*, 92(24): p. 10859-63 (1995).

Canard, et al., "DNA polymerase fluorescent substrates with reversible 3'-tags", *Gene*, 148(1): 1-6 (1994).

Cheng et al., "High-speed DNA sequence analysis," *Prog. in Biochem. and Biophys.*, vol. 22, pp. 223-227 (1995).

Chicurel, M., "Faster, better, cheaper genotyping", *Nature*, vol. 412, Issue 6847, pp. 580-582, (Aug. 2001).

Chidgeavadze et al., 2',3'-Dideoxy-3' aminonucleoside 5'-triphosphates are the terminators of DNA synthesis catalyzed by DNA polymerases, *Nuc. Acids Res.*, 12(3):1671-1686 (1984).

Chidgeavadze, Z. et al., "3'-Fluro-2',3'-dideoxyribonucleoside 5'-triphosphates: terminators of DNA synthesis", *FEBS Letters*, 183(2):275-278 (1985).

Chiu, D. et al., "Patterned deposition of cells and proteins onto surfaces by using three-dimensional microfluidic systems," *PNAS*; vol. 97, No. 6, pp. 2408-2413 (2000).

Chou et al., "A microfabricated device for sizing and sorting DNA molecules", Applied Sciences, Biophysics: Proc. Natl. Acad. Sci. USA 96, pp. 11-13 (1999).

Chou et al., "A Microfabricated Rotary Pump", *Biomedical Microdevices*. vol. 3: p. 323-330 (2001).

Close, D. et al., "Ultraviolet Photobleaching of Free Radicals Created in y-Irradiated Amino Acids", *Radiation Research*, vol. 53, pp. 349-357 (1973).

Cooper, J. et al., "Analysis of Fluorescence Energy Transfer in Duplex and Branched DNA Molecules", *Biochemistry*, vol. 29, pp. 9261-9268 (1990).

Crocker, J.C. and D.G. Grier, "Methods of digital video microscopy for colloidal studies." *Journal of Colloid and Interface Science*, 179(1): p. 298-310 (1996).

Dapprich, J., "Single-molecule DNA digestion by lambda-exonuclease." *Cytometry*, 36(3): p. 163-168 (1999).

Debenham, J.S., et al., "Two New Orthogonal Amine-Protecting Groups that can be Cleaved under Mild or Neutral Conditions." *Journal of the American Chemical Society*, 117(11): p. 3302-3 (1995).

Decher, G. et al. "Buildup of ultrathin multiplayer films by a self-assembly process: III. Consecutively alternating absorption of anionic and cationic polyelectrolytes on charged surfaces", *Thin Solid Films*, 210:831-835 (1992).

Decher G.;et al., "Fuzzy nanoassemblies : Toward layered polymeric multicomposites." *Science*, 277(5330): p. 1232-1237 (1997).

Delamarche, E. et al., "Patterned Delivery of Immunoglobulins to Surfaces Using Microfluidic Networks", *Science* 276:779-781 (1997).

Dickson et al., "Simultaneous Imaging of Individual Molecules aligned both parallel and perpendicular to the optic axis", *The American Physical Society*, vol. 81, No. 24, pp. 5322-5325 (1998).

Doktycz, M. et al., "Genosensors and Model Hybridization Studies", *Automation Technologies for Genome Characterization*, Ch. 10 T. Beugelsdijk (Ed), John Wiley & Sons, Inc., pp. 205-225 (1997).

Doublie, S. et al., "Crystal structure of a bacteriophage T7 DNA replication complex at 2.2 A resolution", *Nature*, vol. 391, pp. 251-258 (Jan. 1998).

Driscoll et al., "Atomic-Scale Imaging of DNA Using Scanning Tunneling Microscopy." *Nature*, 346(6281): p. 294-296 (1990).

Drmanac, R. et al., "Sequencing by hybridization: Towards an automated sequencing of one million M13 clones arrayed on membranes", *Electrophoresis*, 13:566-573 (1992).

Duffy et al., "Patterning Electroluminescence Materials with Feature Sizes as Small as 5 um Using Elastomeric Membranes as Masks for Dry Lift-Off," *Advanced Materials* vol. 11, No. 7, pp. 546-552 (1999).

Duffy et al., "Rapid prototyping of microfluidic switches in poly(dimethyl siloxane) and their acuation by electroosmotic flow," *J. Micromech. Microeng.*, vol. 9, pp. 211-217 (1999).

Duffy et al., "Rapid Prototyping of Microfluidic Systems in Poly(dimethylsiloxane)", *Analytical Chemistry*, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).

Effenhauser et al., "Integrated chip-based capillary electrophoresis," *Electrophoresis*, vol. 18, pp. 2203-2213 (1997).

Eigen, M. et al., "Sorting single molecules: Application to diagnostics and evolutionary biotechnology", *PNAS*, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," *J. Micromech. Microeng.*, vol. 5, pp. 169-171(1995).

Ferguson, et al., "A fiber-optic DNA biosensor microarray for the analysis of gene expression," *Nature Biotechnology*, vol. 14, pp. 1681-1684 (1996).

Forster, T, "Delocalized Excitation and Excitation Transfer", Modem Quantum Chem., *Istanbul Lectures*, Part TII, pp. 93-137, Academic Press, New York (1965).

Fritz, 1. et al., "Electronic detection of DNA by its intrinsic molecular charge", *PNAS*, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual ATP turnovers by single myosin molecules in aqueous solution", *Nature*, vol. 374, pp. 555-559 (Apr. 1995).

Garcia, A., "Determination of Ion Penneability by Fluorescence Quenching", *Meth. in Enzymology*, 207:501-511 (1992).

Gardner, A., et al., "Acyclic and dideoxy terminator preferences denote divergent sugar recognition by archaeon and *Taq* DNA polymerases",*Nucleic Acids Research*, vol. 30, No. 2, pp. 605-613 (2002).

Gardner et al., "Comparative kinetics of nucleotide analog incorporation by Vent DNA polymerase," *J. Biol. Chem.*, 279, No. 12, p. 11834-11842 (2004).

Giller et al., "Incorporation of reporter molecule-labeled nucleotides by DNA polymerases. I. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5'-Fluorescent-dye-labeled Oligonucleotides", *PCR Methods and Applications*, 2:223-227 (1993).

Goll et al., "Microvalves with bistable buckled polymer diaphragms," *J. Micromech. Microeng.*, vol. 6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley & Sons, Inc.: New York, 1999 3rd Ed.

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C., et al., "A general method for the synthesis of 3'-sulfhydryl and phosphate group containing oligonucleotides", *Nucleic Acids Res.*, 1901:3019-25 (1991).

Gyllenstein, U. et al., "Generation of single-stranded DNA by the polymerase chain reaction and its application to direct sequencing of the *HLA-DQA* locus", *PNAS*, 85:7652-56 (1988).

Ha, "Single molecule dynamics studied by polarization modulation," *Phys. Rev. Lett.*, 77, No. 19, 3979-3982 (1996).

Ha, "Single molecule spectroscopy with automated positioning," *Appl. Phys. Lett.* 70, No. 6, 782-784 (1997).

Ha, "Single-molecule fluorescence methods for the study of nucleic acids," *Current Opinion in Struct Bio*, 11, 287-292 (2001).

Ha et al., "Single-molecule fluorescence spectroscopy of enzyme conformational dynamics and cleavage mechanism," *PNAS*, 96(3): p. 893-898 (1999).

Ha, T., "Single-molecue fluorescence resonance energy transfer," *Methods*, 25(1): p. 78-86 (2001).

Hanna, M. et al., "Synthesis and characterization of a new photocrosslinking CTP analog and its use in photoaffmity labeling *E. coli* and T7 RNA polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99 (26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and biomedical applications of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp, 895-897 (1993).

Harrison, D., et al., "Towards miniaturized electrophoresis and chemical analysis systems on silicon: an alternative to chemical sensors", *Sensors and Actuators B*, 10, pp. 107-116 (1993).

Hasan, A. et al., "Photolabile Protecting Groups for Nucleosides: Synthesis and Photodeprotection Rates", *Tetrahedron*, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," *Anal. Chem.*, vol. 71, No. 20, pp. 4781-4785 (1999).

Houseal, T. et al., "Real-time imaging of single DNA molecules with fluorescence microscopy", *Biophys. I.*, vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct observation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", *BioTechniques*, vol. 10, No. 1, pp. 84-93 (1991).

Hyman, E., "A New Method of Sequencing DNA", *Anal. Biochem.*, 174:423-436 (1988).

Ikuta et al., "Three dimensional micro integrated fluid systems (MIFS) fabricated by stereo lithography", *IEEE Kyushu Institute of Technology*, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", *Cell*, vol. 92, pp. 161-171, (Jan. 1998).

Ishikawa, M. et al., "Single-Molecule Detection by Laser-Induced Fluorescence Technique with a Position-Sensitive Photon-Counting Apparatus", *Appl. Phys.*, vol. 33, Part 1, No. 3A, pp. 1571-1576 (1994).

Jacobs et al., "Combinatorial chemistry—applications of light-directed chemical synthesis", *TIBTech*, vol. 12, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", *J. Biomolecular Structure & Dynamics*, vol. 7, No. 2, pp. 301-309, (1989).

Johnston, R. et al., "Autoradiography using storage phosphor technology", *Electrophoresis*, 11 :355-360 (1990).

Jongeneel, C.V., et al., "Comprehensive sampling of gene expression in human cell lines with massively parallel signature sequencing". Proc Natl Acad Sci U S A, 100(8): p. 636-639 (2003).

Zoos, B. et al., "Covalent Attachment of Hybridizable Oligonucleotides to Glass Supports", *Anal. Biochem.* 247(1):96-101 (1997).

Kambara, H. et al., "Optimization of Parameters in a DNA Sequenator using Fluorescence Detection", *Biotechnology*, vol. 6, pp. 816-821 (1988).

Kartalov, Emil P., et al., "Microfluidic device reads up to four consecutive base pairs in DNA sequencing-by-synthesis", *Nucleic Acids Research*, vol. 32, No. 9, pp. 2873-2879 (2004).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass", http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", *Analytical Biochemistry*, 209:63-69 (1993).

Kelso et al., "Single-cell analysis by RT-PCR reveals differential expression of multiple type 1 and 2 cytokine genes among cells within polarized CD4+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", *Mole. Bio. Rep.* 11:107-115 (1986).

Khrapko, K. et al., "A method for DNA sequencing by hybridization with oligonucleotide matrix", *DNA Sequence-J. DNA Sequencing and Mapping*, vol. 1, pp. 375-388 (1991).

Kiefer, J. et al., "Crystal structure of a thermostable *Bacillus* DNA polymerase I large fragment at 2.1 A resolution", *Structure*, 5:95-108 (1997).

Kim, Y. et al., "Crystal structure of *Thermus aquaticus* DNA polymerase", *Nature*, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R.R. Schmidt, "Application of a ring-closing-metathesis-based linker to the solid phase synthesis of oligosaccharides" Synlett, 11: p. 1802-1804 (1999).

Kopp, et al., "Chemical Amplification: Continuous-Flow PCR on a Chip", Science, vol. 280, pp. 1046-1048 (May 1998).

Korolev, S. et al., "Crystal structure of the large fragment of *Thermus aquaticus* DNA polymerase I at 2.5 A resolution: Structural basis for thermo stability", *PNAS*, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch. 1 and Table 1x, Academic Press, New York, pp. 3-40, (1995).

Krider, E. et al., "2'-Modified Nucleosides for Site-Specific Labeling of Oligonucleotides", *Bioconjugate Chem.*, vol. 13, No. 1, pp. 155-162 (2002).

Kuhn, L. et al., "Silicon Charge Electrode Array for Ink Jet Printing", *IEEE Trans. On Electron Dev.*, vol. ED-25, No. 10, pp. 1257-1260 (Oct. 1978).

Lacoste, T. et al., "Ultrahigh-resolution multicolor colocalization of single fluorescent probes", *PNAS*, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", *Antisense and Nucleic Acid Drug Dev.*, vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", *Anal. Chem.*, vol. 66, pp. 4142-4149 (1994).

Levene, M. et al., "Zero-Mode Waveguides for Single-Molecule Analysis at High Concentrations", *Science*, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", *Anal. Chem.*, 75:1664-1670 (2003).

Li, Y. et al., "Design, Synthesis, and Spectroscopic Properties of Peptide-Bridged Fluorescence Energy-Transfer Cassettes", *Bioconjuate Chem.*, 10:241-245 (1999).

Li, Y. et al., "Structural Studies of the Klentaq 1 DNA Polymerase", *Current Organic Chem.*, 5:871-883 (2001).

Li, Z. et al., "A photocleavable fluorescent nucleotide for DNA sequencing and analysis", *PNAS*, vol. 100, No. 2, pp. 414-419 (2003).

Lin, L. et al., "Free-Space Micromachined Optical Switches for Optical Networking", *IEEE J. of Selected Topics in Quanturn Electronics*, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2002).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", Science 243:217-220 (1989).

Lok, Corie, "Deciphering DNA, Top Speed—Helicos BioSciences aims to expedite sequencing, enable genomic medicine," *Technology Review*, pp. 27-28 (May 2005).

Lopez, G. et al., "Fabrication and Imaging of Two-Dimensional Patterns of Proteins Adsorbed on Self-Assembled Monolayers by Scanning Electron Microscopy", *J. Arner. Chem. Soc.*, 115:10774-81 (1993).

Lotters et al., "The mechanical properties of the rubber elastic polymer polydimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'-0-(1-Thiotriphosphates), 5+-triphosphates and 2',3'-Cyclophosphorothioates Using 2-Chloro-4$H$-1,3,2-benzodioxaphosphorin-4-one." Journal of Organic Chemistry, 54(3): p. 631-635 (1989).

Lvov, Yu. et al., "Assembly of Thin Films by Means of Successive Deposition of Alternate Layers of DNA and Poly(allylamine)", *American Chemical Society, Macromolecules*, 26, pp. 5396-5399, (1993).

Macklin, J. et al., "Imaging and Time-Resolved Spectroscopy of Single Molecules at an Interface", *Science*, vol. 272, No. 5259, pp. 255-258 (Apr. 1996).

Maier, B., D. Bensimon, and V. Croquette, "Replication by a single DNA polymerase of a stretched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", *Biophys. J.*, vol. 60, pp. 1374-1387 (Dec. 1991).

Marziali, A. and M. Akeson, "New DNA sequencing methods." Annual Review of Biomedical Engineering, 3: p. 195-223 (2001).

Mastrangelo, C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA molecules." Phys Rev Lett, 84(21): p. 5014-7 (2000).

Meldrum, Kevin, "Microfluidics-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." *PNAS*, 97(3): p. 1079-1084 (2000).

Mertz, J. et al., "Single-molecule detection by two-photon-excited fluorescence", *Optics Letters*, vol. 20, No. 24, pp. 2532-34 (Dec. 1995).

Metzker et al., "Elimination of residual natural nucleotides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'-triphosphates." Nucleic Acids Res, 22(20): p. 4259-67 (1994).

Mitra, Robi, et al., "Fluorescent in situ sequencing on polymerase colonies", *Analytical Biochemistry*, 320, pp. 55-65 (2003).

Moe et al., Rapid Detection of Clinically Relevant Bacteria in Platelets Using the Hybriscan Baceterial Detection system, Journal of the American Society of Hematology, 96, No. 11, 4155 (2000).

Moore, P., "To affinity and beyond", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 518'/, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, vol. 208, pp. 171-175 (1993).

Ochman, H. et al., "Genetic Applications of an Inverse Polymerase Chain Reaction", *Genetics* 120:621-623 (1988).

Ohara, To et at, "'Wired' Enzyme Electrodes for Amperometric Determination of Glucose or Lactate in the Presence of Interfering Substances", *Anal. Chem.*, vol. 66, No. 15, pp. 2451-2457 (Aug. 1994).

Ohara, T. et al., "Glucose Electrodes Based on Cross-Linked [Os(bpY)2CItH Complexed Poly(1-vinylimidazole) Films", *Anal. Chem.*, vol. 65, pp. 3512-3517 (1993).

Okabe, S. et al., "Do Photobleached Fluorescent Microtubules Move?: Re-evaluation of Fluorescence Laser Photobleaching both In Vitro and in Growing Xenopus Axon", *J. Cell Bio.*, vol. 120, No. 5, pp. 1177-1186 (1993).

Ollis, D. et al., Structure of large fragment of *E. coli* DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Amer. Chem. Soc.*, 92(21):6333-37 (1970).

Padmaja, T., et al., "Enzymatically degradable prodrugs: a novel methodology for drug linkage." Journal of Applied Polymer Science, 85(10): p. 2108-2118 (2002).

Pennisi, E., "Gene researchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et at, "Applications of dielectrophoresis in biotechnology", *Tibtech*, vol. 15, pp. 426-432 (Oct. 1997).

Pisani, F. et at, "Domain Organization and DNA-Induced Conformational Changes of an Archaeal Family B DNA Polymerase", *Biochemistry*, vol. 35, pp. 9158-9166 (Jul. 1996).

Plakhotnik, T. et at, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Lascr Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Rapp, R. et al., "LIGA micropump for gases and liquids", *Sensors and Actuators A*, vol. 40, pp. 57-61 (1994).

Rasolonjatovo I. and S.R. Sarfati, "6-N-(N-methylanthranyamido)-4-oxo-hexanoic acid: a new florescent protecting group applicable to a new DNA sequencing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides, 18(4 & 5): p. 1021-1022 (1999).

Reha-Krantz, L. et al., "Genetic and Biochemical Studies of Bacteriophage T4 DNA Polymerase 3'→5'-Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primer Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Ronaghi, M et al., "Real-Time DNA Sequencing Using Detection of Pyrophosphate Release." *Analytical BioChemistry*, 242, No. 0432, (1996).

Rosenblum, B. et al., "New dye-labeled terminators for improved DNA sequencing patterns", *Nucleic Acids Research*, vol. 25, No. 22, pp. 4500-4504 (Nov. 1997).

Rosenblum, B. et al., "Improved single-strand DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917 (1979).

Ruparel, Hameer, "Design and synthesis of a 3'-*O*-allyl photocleavable fluorescent nucleotide as a reversible terminator for DNA sequencing by synthesis", *PNAS*, vol. 102, No. 17, pp. 5932-5937 (Apr. 26, 2005).

Ruth, J. et al., "Nucleoside Analogues with Clinical Potential-in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-*O*-(6-aminohexanoyl)-pyrimidine nucleosides 5'-triphosphates that act as DNA polymerase substrates reversibly tagged at C-3'." Journal of the Chemical Society, Perkin Transactions 1: Organic and Bio-Organic Chemistry, 9: p. 1163-71 (1995).

Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts*, vol. 110, No. 16, pp. 409-413 (1988).

Sauer, M., et al., "Single molecule DNA sequencing in submicrometer channels: state of the art and future prospects." Journal of Biotechnology, 86(3): p. 181-201 (2001).

Schasfoort et al., "Field-effect flow control for microfabricated fluidic networks," Science, vol. 286, pp. 942-945 (1999).

Schueller, O., et al., "Reconfigurable diffraction gratings based on elastomeric microfluidic devices", *Sensors and Actuators*, 78, pp. 149-159 (1998).

Seeger, S. et al., "Single molecule fluorescence—High Performance Molecular Diagnosis and Screening", translated from *BIOforum*, pp. 179-185, (Apr. 1998).

Selvin, P., "Fluorescence Resonance Energy Transfer", *Meth. In Enzymology*, vol. 246, pp. 300-335, Academic Press (1995).

Seo, Tae Seok, "Four-color DNA sequencing by synthesis on a chip using photocleavable fluorescent nucleotides", *PNAS*, vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAS*, vol. 101, No. 15, pp. 5488-5493 (Apr. 13, 2004).

Shackelford, James F., "Intro. to Materials Science for Engineers," 3rd Edition, Prentice-Hall, Inc., Macmillan Publ. Co. (1992).

Shendure et al., "Advanced sequencing technologies: Methods and goals," *Nature Reviews*, vol. 5, No. 5, pp. 335-344 (2004).

Shoji, S. et al., "Smallest Dead Volume Microvalves for Integrated Chemical Analyzing Systems", *Proceedings of Transducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature*, vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", *Nucleic Acids Res.*, vol. 13, No. 7, pp. 2399-2412 (1985).

Smith, S. et al., "Direct Mechanical Measurements of the Elasticity of Single DNA Molecules by Using Magnetic Beads", *Science* 258:1122-26 (1992).

Smits, I., "Piezoelectric Micropump with Three Valves Working Peristaltically", *Sensors and Actuators*, vol. A21-A23, pp. 203-206 (1990).

Song et al., "Influence of the triplet excited state on the photobleaching kinetics of fluorescein in microscopy," Biophysics J., 70, 2959-2968 (1996).

Sproat, B. et al., "The synthesis of protected 5'-mercapto-2',5'-dideoxyribonucleoside-3'-O-phosphoramidities; uses of 5'-mercapto-oligodeosyribonucleotides", *Nucleic Acids Res.*, I5(12):4837-48 (1987).

Stocki, S. et al., "Dynamics of Bacteriophage T4 DNA Polymerase Function: Identification of Amino Acid Residues that Affect Switching between Polymerase and 3'43 5'-Exonuclease Activities", *J. Mol. Biol.*, 254, pp. 15-28 (1995).

Strausberg, R L, et al., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", *Thin Solid Films*, 284-285, pp. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", *Mol. Cell Probes*, vol. 6, No. 4, pp. 265-270 (1992).

Taylor, D. et al., "Characterization of chemisorbed monolayers by surface potential measurements", J. *Phys. D. Appl. Phys*. 24:1443-50 (1991).

Terry, S. et al., "A Gas Chromatographic Air Analyzer Fabricated on a Silicon Wafer", *IEEE Trans. on Electron Dev.*, vol. ED-26, No. 12, pp. 1880-1886 (1979).

Theisen, P. et al., "Fluorescent dye phosphoramidite labeling of oligonucleotides", *Nucleic Acids Symp. Ser.*, vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.*, vol. 33, pp. 435-454 (Mar. 1981).

Thompson, N. et al., "Immunoglobulin Surface-Binding Kinetics Studied by Total Internal Reflection with Fluorescence Correlation Spectroscopy", *Biophys. J.*, vol. 43, pp. 103-114 (Jul. 1983).

Thorsen, T. S.J. Maerkl, and S.R. Quake, "Microfluidic large-scale integration." Science, 298(5593): p. 580-4 (2002).

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.*, vol. 235, pp. 47-53 (1997).

Toneguzzo, F. et al., "Use of a Chemically Modified T7 DNA Polymerase for Manual and Automated Sequencing of Super coiled DNA", *BioTech*, vol. 6, No. 5, pp. 460-469 (1988).

Trager, R. S., "DNA sequencing—Venter's next goal: 1000 human genomes." Science, 298(5595): p. 947 (2002).

Tufte, O. et al., "Silicon Diffused-Element Piezoresistive Diaphragms", *J. Applied Phys.*, vol. 31, No. 11, pp. 3322-3327 (Nov. 1962).

Tyagi, S. et al., "Multicolor molecular beacons for allele discrimination", *Nat. Biotechnol.*, 16:49-53 (1998).

Ullman's Encyclopedia of industrial Chemistry, 6ID Edition, vol. 6, Sections 6 to 6.3, Subject: Carbon Black, Wiley-VCH (1999).

Unger et al., "Monolithic microfabricated valves and pumps by multilayer soft lithography," Science 288: 113-116 (2000).

Unger, M. et al, "Single-Molecule Fluorescence Observed with Mercury Lamp Illumination", *BioTechniques*, vol. 27, PD. 1008-1014 (Nov. 1999).

Vale, R. et al., "Direct observation of single kinesin molecules moving along microtubules", *Nature*, vol. 380, pp. 451-453, (Apr. 1996).

Van Dam, R.M. and S.R Quake, "Gene expression analysis with universal n-mer arrays." Genome Res, 12(1): p. 145-52 (2002).

Van De Pol, F. et al., "Micro-liquid handling devices: A Review", Micro System Technologies 90, 1st Intl. Conf. On Micro Electro, Opto, Mechanic Systems and Components, pp. 799-805, Berlin, Springer-Verlag, (1990).

Van Oijen et al., "Single molecule kinetics of X. exonuclease reveal base dependence and dynamic disorder," Science, 301, 1235-1238 (2003).

Venter, J.L., et al., "The sequence of the human genome." Science, 291(5507): p. 1304-1351 (2001).

Vieider, C. et al., "A Pneumatically Actuated Micro Valve With a Silicone Rubber Membrane for Integration With Fluid-Handling Systems", *Proceedings of Transducers* '95, pp. 284-286, Stockholm (1995).

Walker, M.G., et al., "Prediction of gene function by genome-scale expression analysis: Prostate cancer-associated genes.": Genome Researce, 9(12): p. 1198-1203 (1999).

Wang, G. et al., "Design and Synthesis of New Fluorogenic HIV Protease Substrates Based on Resonance Energy Transfer", *Tetrahedron Lett.*, 31(45):6493-96 (1990).

Wang, M.D., et al., "Force and Velocity measured for single molecules of RNA polymerase." Science, 282(5390): p. 902-907 (1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", *J. Biomed. Mater. Res.*, vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", Intl. Con£ on MEMS (MEMS 96), pp. 491-496 (1996).

Wedekind, P. et al., "Scanning microphotolysis: a new photobleaching technique based on fast intensity modulation of a scanned laser beam and confocal imaging", *J. Microscopy*, vol. 176, Pt. 1, pp. 23-33 (Oct. 1994).

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", *Science*, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme." Nucleosides & Nucleotides, 18(2): p. 197-201 (1999).

Werner et al "Progress towards single-molecule DNA sequencing: a one color demonstration." J Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", *J. Bioi. Chem.*, 237(6):2834-41 (1982).

Winter et al., "Direct gene expression analysis," Curr. Pharm. Biotech., 5, p. 191-197 (2004).

Wu, et al., "Synthesis and Properties of Adenosine-5'-triphosphoro-γ-1-(5-sulfonic acid)naphthyl Ethylamide: A Fluorescent Nucleotide Substrate for DNA-Dependent RNA Polymerase from *Escherichia coli*," Archives of Biochemistry and Biophysics, vol. 246, No. 2, pp. 564-571 (1986).

Wuite, G. et al., "Single-molecule studies of the effect of template tension on T7 DNA polymerase activity", *Nature*, 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 550-575 (1998).

Xia, G., et al., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", *Science*, vol. 275, pp. 1106-1109, (Feb. 1997).

Xu, X. et al., "Long-Range Electrostatic Trapping of Single-Protein Molecules at a Liquid-Solid Interface", *Science*, vol. 281, pp. 1650-1653 (Sep. 1998).

Yang et al., "A Mems Thermopneumatic Silicone Rubber Membrane Valve", Proceedings of IEEE 10$^{th}$ Annual International Workshop on MicroElectro Mechanical Systems, Sensors and Actuators, vol. A64, No. 1, pp. 101-108 (1998).

Yazdi, N. et al., "Micromachined Inertial Sensors", *Proceedings of the IEEE*, vol. 86, No., pp. 1640-1659 (Aug. 1998).

Yershov, G. et al., "DNA analysis and diagnostics on oligonucleotide microchips", *Proc. Natl. Acad. Sci. USA*, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et al., "Cyanine dye dUTP analogs for enzymatic labeling of DNA probes." Nucleic Acids Res, 22(15): p. 3226-32 (1994).

Zdeblick, M. et al., "A Microminiature Electric-To-Fluidic Valve", Transducers '87, reprinted in *Micromechanics and MEMS Classic and Seminal Papers to 1990*, IEEE Press, pp. 437-439 (1987).

Zhu, Z. et al., "Molecular Mechanism Controlling the Incorporation of Fluorescent Nucleotides into DNA by PCR", *Cytometry*, 28:206-211 (1997).

Zhu, Z. et al., "Directly labeled DNA probes using fluorescent nucleotides with different length linkers", *Nucleic Acids Res.*, vol. 22, No. 16, pp. 3418-3422 (1994).

Zuckerman, R. et al., "Efficient methods for attachment of thiol specific probes to the 3' ends of synthetic oligodeoxyribonucleotides", *Nucleic Acids Res.*, 15(13):5305-5321 (1987).

Therminator DNA Polymerase FAQ, http://www.neb.com/nebecomm/products/faqproductM0261.asp downloaded Jun. 1, 2005, 1 page.

Pending claims (as of Jun. 4, 2008) from related U.S. Appl. No. 11/588,108; unpublished.

* cited by examiner

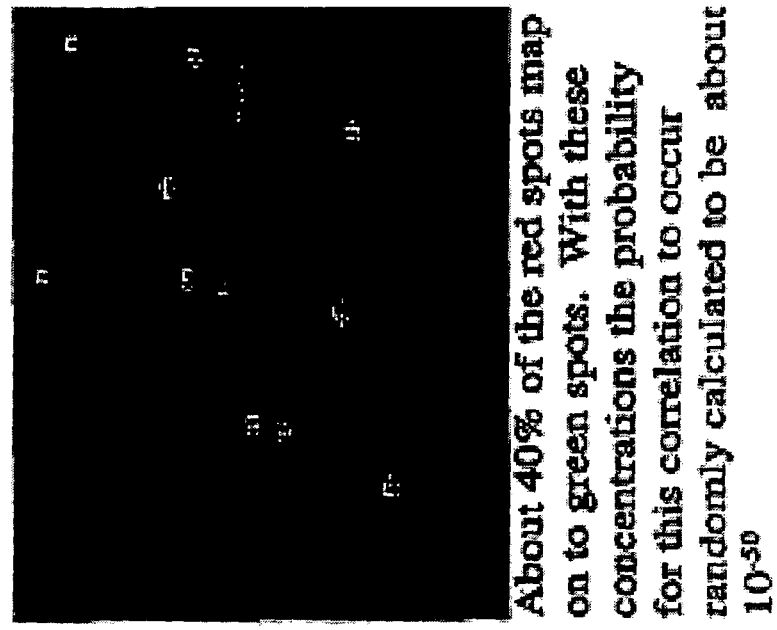
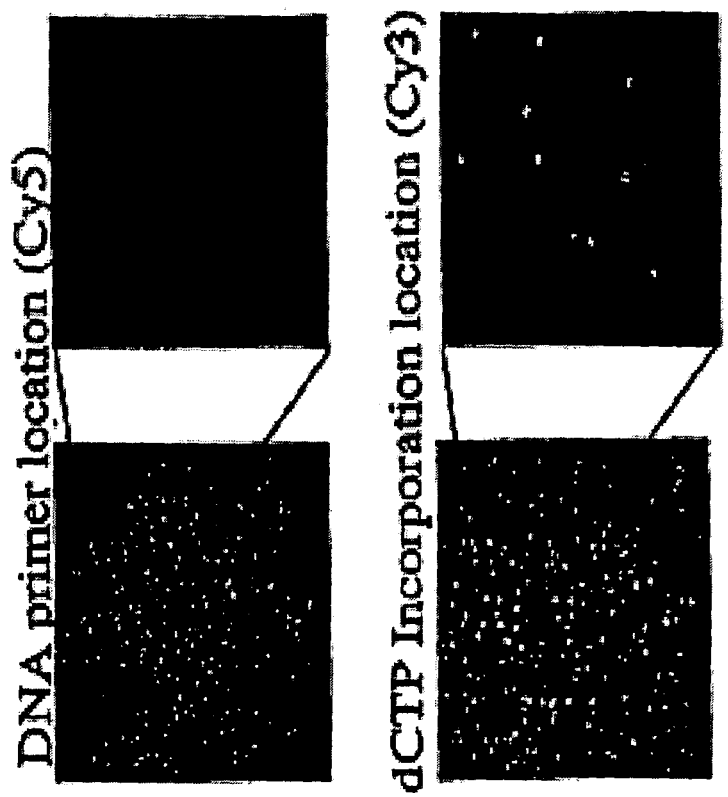
FIG. 4

FIG. 16 On-surface incorporation in anchored DNA can be visualized at the single-DNA level.
(a) Positive incorporation (A-Lis,C,G,T, polymerase).
(b) DNA polymerase withheld (A-Lis,C,G,T).
(c) Fluorescent nucleotide and DNA polymerase withheld (A,C,G,T).

Example 12:

Inputs

Number of half-lives till dNTP's are flushed   0.8
*0.1-10.0 in increments of 0.1*

Number of wash cycles   60
*1-50 in increments of 1*

Number of strands to analyze (1100 max)   200

Outputs

| | | |
|---|---|---|
| Longest extension in the ensemble of molecules | 48 | Bases |
| Shortest extension in the ensemble of molecules | 20 | Bases |
| Average Extension | 32.00 | Bases |
| Fraction of molecules which had 2 extensions in a homopolymer: | | 78.5% |
| Fraction of molecules which had 3+ extensions in a homopolymer: | | 4.0% |
| Fraction of molecules for which at least 25 bases sequenced: | | 95.5% |

Target Strand Analysis

| Length | Frequency |
|---|---|
| 1-mer | 5769 |
| 2-mer | 1406 |
| 3-mer | 304 |
| 4-mer | 94 |
| 5-mer | 19 |
| 6-mer | 6 |
| 7-mer | 0 |
| 8-mer | 0 |
| >=9-mer | 0 |

Synthesized Strand Analysis

| Length | Frequency |
|---|---|
| 1-mer | |
| 2-mer | |
| 3-mer | |
| 4-mer | |
| 5-mer | |
| 6-mer | |
| 7-mer | |
| 8-mer | |
| >=9-mer | |

*FIG. 20*

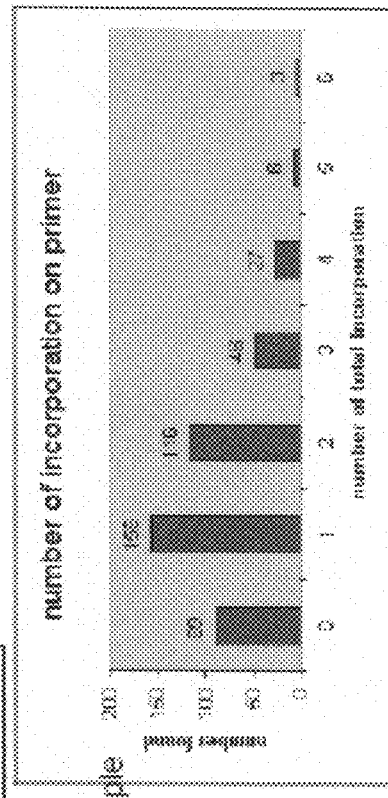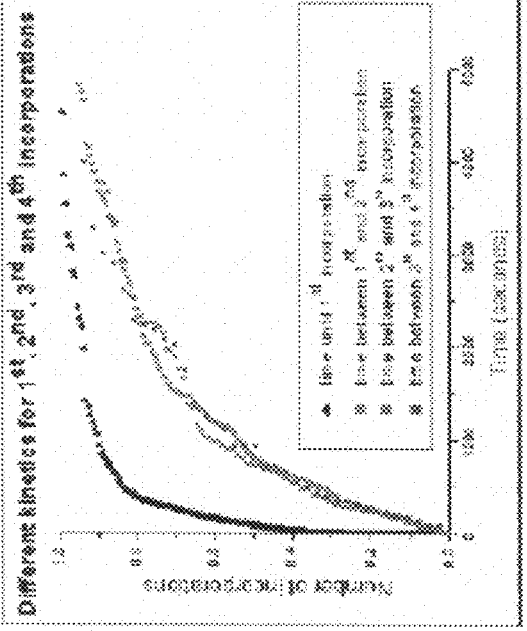
FIG. 21

US 7,981,604 B2

METHODS AND KITS FOR ANALYZING POLYNUCLEOTIDE SEQUENCES

REFERENCE TO RELATED APPLICATIONS

This non-provisional patent application claims the benefit of and priority to U.S. provisional application No. 60/546,277, filed Feb. 19, 2004, and U.S. provisional application No. 60/547,611, filed Feb. 24, 2004. Reference also is made to U.S. non-provisional application Ser. No. 09/605,520, filed Jun. 27, 2000; U.S. provisional patent application No. 60/141,503, filed Jun. 28, 1999; U.S. provisional patent application No. 60/147,199, filed Aug. 3, 1999; U.S. provisional patent application No. 60/163,742, filed Nov. 4, 1999; U.S. provisional patent application No. 60/186,856, filed Mar. 3, 2000, and U.S. provisional patent application No. 60/275,232, filed Mar. 12, 2001; U.S. non-provisional application Ser. No. 09/707,737, filed Nov. 6, 2000; U.S. non-provisional application Ser. No. 09/908,830, filed Jul. 18, 2001; and U.S. non-provisional application Ser. No. 10/099,459, filed Mar. 12, 2002; as well as U.S. provisional application No. 60/519,862, filed Nov. 12, 2003. The text of each of the foregoing patent applications is hereby incorporated by reference.

TECHNICAL FIELD OF THE INVENTION

The invention generally relates to methods for analyzing the sequence of a target polypeptide. More particularly, the invention involves detecting incorporation of a nucleotide into the complementary strand of the target polypeptide.

BACKGROUND OF THE INVENTION

Genetic sequencing finds many important applications in biotechnology, genetics, and pharmacology, as well as medical diagnoses and therapeutic treatments. For example, sequencing individual genomes and individual cells can be used to determine genetic variability, disease susceptibility and pharmaceutical efficacy. While earlier methods have proved useful in these applications, there remains a need in the art for even better methods of analyzing genetic information.

SUMMARY OF THE INVENTION

I. Introduction

The present invention provides methods and kits for analyzing the sequence of a target polypeptide by detecting incorporation of a nucleotide into its complementary strand. Certain embodiments provide for detection of a single nucleotide into a single target polynucleotide. Some embodiments use labeling moieties that facilitate chain termination or choking. Some embodiments use separate labeling and blocking moieties, but still allow single step reversal of chain termination and reduction of incorporated signals. Some embodiments use bleachable labeling moieties, whose signal can be reduced without cleavage of the structural moiety. Some embodiments use quenched labeling moieties, which become detectable upon incorporation and/or upon further reaction. Certain aspects provide for allowing successive incorporations of a number of nucleotides on a support; other aspects allow for temporal detection of the incorporations.

Certain embodiments of the present invention are directed to analysis of a plurality of target polynucleotides in parallel. For example, methods of parallel analysis of a plurality of polynucleotide molecules randomly bound to a substrate are provided. In certain embodiments, the polynucleotide molecules are bound at high density and at single molecule resolution. Moreover, certain embodiments allow for asynchronous analysis of the plurality of target polynucleotides and the use of short sequencing cycles.

The present invention also provides numerous applications of the sequencing and analysis methods. Some embodiments provide for identifying the address of a polynucleotide molecule randomly bound to a substrate, while some embodiments provide for counting copies of identified molecules.

Certain aspects of the invention relate to analyzing DNA sequences and applications corresponding thereto. For example, some embodiments provide for identifying a mutation useful, for example, in diagnosis and/or prognosis of conditions such as cancer. Certain embodiments provide methods of doing genetic cancer research, for example, by identifying changes in cell diploidy.

Other aspects of the invention relate to analyzing RNA sequences and applications corresponding thereto. Such embodiments include methods for enumerating copy number of RNA transcripts, methods for identifying alternate splice sites, and methods for analyzing the RNA sequences of a cell in parallel. These methods find use in a number of applications also provided herein, including identifying unknown RNA molecules, annotating genomes based on transcribed sequences, and determining phylogenic relationships of various species. Other embodiments provide for determining cellular responses to different stimuli, while still other embodiments provide for compiling transcriptional patterns of cells in different stages of cellular differentiation, thereby facilitating methods of tissue engineering.

Yet other aspects of the present invention relate to surface chemistry. Some such embodiments provide substrates and methods for hindering an anchored polynucleotide from lying down, as well as for reducing background fluorescence when detecting fluorescently-labeled nucleotides incorporated into the complementary strand. Moreover, some of these embodiments permit high density anchoring of polynucleotide molecules at single molecule resolution.

II. Aspects of the Present Invention

A. Fluorescent Single Base Extension on a Substrate

In one aspect, the present invention provides methods for analyzing the sequence of a target polynucleotide. The methods include the steps of:

(a) providing a primed target polynucleotide immobilized to a surface of a substrate; wherein the target polynucleotide is attached to the surface with single molecule resolution;

(b) in the presence of a polymerase, adding a first fluorescently labeled nucleotide to the surface of the substrate under conditions whereby the first nucleotide attaches to the primer, if a complementary nucleotide is present to serve as template in the target polynucleotide;

(c) determining presence or absence of a fluorescence signal on the surface where the target polynucleotide is immobilized, the presence of a signal indicating that the first nucleotide was incorporated into the primer, and hence the identity of the complementary base that served as a template in the target polynucleotide; and (d) repeating steps (b)-(c) with a further fluorescently labeled nucleotide, the same or different from the first nucleotide, whereby the further nucleotide attaches to the primer or a nucleotide previously incorporated into the primer.

B. Choking (Including Sanger-like Sequencing Using Choking Moieties)

Some embodiments of the invention provide methods for analyzing a sequence of a target polynucleotide by synthesizing a complementary strand, comprising: providing a labeled nucleotide, said labeled nucleotide comprising a labeling moiety hindering further chain elongation by steric hindrance; allowing incorporation of said nucleotide into said complementary strand in the presence of a polymerizing agent; and detecting incorporation, thereby analyzing said sequence of said target polynucleotide. Methods also may be used in kits, said kits designed to carry out and facilitate the methods provided herein.

C. Single Step Bleaching & Cleaving

Some embodiments of the invention provide methods for analyzing a sequence of a target polynucleotide by synthesizing a complementary strand, comprising: providing a labeled nucleotide, said labeled nucleotide comprising a labeling moiety and a blocking moiety, wherein said moieties are capable of being bleached and cleaved, respectively, in a single step of bleaching and cleaving; allowing incorporation of said nucleotide into said complementary strand in the presence of a polymerizing agent; and detecting incorporation, thereby analyzing said sequence of said target polynucleotide. Methods also may be used in kits, said kits designed to carry out and facilitate the methods provided herein.

D. Noncleavable Labeling Moiety Approach

Some embodiments of the invention provide methods for analyzing a sequence of a target polynucleotide by synthesizing a complementary strand, comprising: anchoring said target polynucleotide to a surface of a substrate; providing two or more types of labeled nucleotide, said labeled nucleotide comprising a non-cleavable labeling moiety and a blocking moiety; allowing incorporation of said nucleotide into said complementary strand in the presence of a polymerizing agent; and detecting incorporation; thereby analyzing said sequence of said target polynucleotide. Methods also may be used in kits, said kits designed to carry out and facilitate the methods provided herein.

E. Non-α-Phosphate-Quenching

Some embodiments of the invention provide methods for analyzing a sequence of a target polynucleotide by synthesizing a complementary strand, comprising: providing a labeled nucleotide, said labeled nucleotide comprising a quenching moiety on at least one of a non-α-phosphate of said nucleotide and a fluorescent moiety; allowing incorporation of said nucleotides into said complementary strand in the presence of a polymerizing agent; and detecting incorporation, thereby analyzing said sequence of said target polynucleotide. Methods also may be used in kits, said kits designed to carry out and facilitate the methods provided herein.

F. Asynchronous and Short-Cycle Sequencing

Some embodiments of the invention provide methods for analyzing sequences of two or more target polynucleotides by asynchronously synthesizing two or more complementary stands in parallel, comprising: localizing said target polynucleotides on a surface of a substrate at individually-addressable locations; providing a labeled nucleotide, said nucleotide comprising a labeling moiety; allowing incorporation of said nucleotide into said complementary strands in the presence of a polymerizing agent wherein different numbers of said nucleotide may be incorporated into at least two of said complementary strands in a given period of time; detecting incorporation at said individually-addressable locations for said given period of time; thereby analyzing said sequences of said target polynucleotides. Methods may also be used in kits, said kits designed to carry out and facilitate the methods provided herein.

Some embodiments of the invention also provide methods for analyzing a sequence of a target polynucleotide by synthesizing a complementary strand, comprising:

localizing said target polynucleotide on a surface of a substrate; providing a labeled nucleotide, said nucleotide comprising a labeling moiety; allowing a cycle of incorporation reactions of said nucleotide into said complementary strand in the presence of a polymerizing agent; halting said cycle after a period of time, said period permitting at least a chance of incorporation of two or less of said nucleotides into said complementary strand; and detecting incorporation, thereby analyzing said sequence of said target polynucleotide. Methods also may be used in kits, said kits designed to carry out and facilitate the methods provided herein.

G. Movie Mode

Some embodiments of the invention provide methods for analyzing a sequence of a target polynucleotide by synthesizing a complementary strand, comprising: providing four types of nucleotides wherein at least one of said types of nucleotides is a labeled nucleotide comprising a labeling moiety; allowing incorporation of said labeled nucleotide into said complementary strand in the presence of a polymerizing agent; and temporally detecting incorporation, thereby analyzing said sequence of said target polynucleotide. Methods may also be used in kits, said kits designed to carry out and facilitate the methods provided herein.

H. Single Base Extension of Randomly Bound Molecule

Some embodiments of the invention provide methods for analyzing a sequence of a randomly-localized target polynucleotide by synthesizing a complementary strand, comprising: permitting random localization of said target polynucleotide on a surface of a substrate; providing a labeled nucleotide, said nucleotide comprising a labeling moiety; allowing incorporation of said nucleotide into said complementary strand in the presence of a polymerizing agent; and detecting incorporation, thereby analyzing said sequence of said target polynucleotide. Methods also may be used in kits, said kits designed to carry out and facilitate the methods provided herein.

I. High Density Single Base Extension

Some embodiments of the invention provide methods for analyzing a sequence of a target polynucleotide at high density by synthesizing a complementary stand, comprising: permitting localization of said target polynucleotide on a surface of a substrate at a density of at least 1,000 target polynucleotides per $cm^2$; providing a labeled nucleotide, said nucleotide comprising a labeling moiety; allowing incorporation of said nucleotide into said complementary stand in the presence of a polymerizing agent; and detecting incorporation, thereby analyzing said sequence of said target polynucleotide. Methods also may be used in kits, said kits designed to carry out and facilitate the methods provided herein.

J. Address Identification of Randomly Bound Molecule

Some embodiments of the invention provide methods for identifying an address of a randomly-localized target polynucleotide, comprising: permitting random localization of said target polynucleotide on a surface of a substrate; providing a labeled nucleotide, said nucleotide comprising a labeling moiety; allowing hybridization of said labeled nucleotide to a complementary base of said target polynucleotide before or after said step of permitting random localization; and detecting said labeled nucleotide, thereby identifying said location of said randomly-localized target polynucleotide. Methods also may be used in kits, said kits designed to carry out and facilitate the methods provided herein.

K. Achieving Sequencing of a Given Number of Bases on a Support

Some embodiments of the invention provide methods of analyzing a number of bases of a sequence of a target polynucleotide by synthesizing a complementary strand, comprising: permitting localization of said target polynucleotide on a surface of a substrate; providing up to four types of nucleotides, at least one of said types comprising a labeling moiety and allowing incorporations of said number of said nucleotides into said complementary strand in the presence of a polymerizing agent wherein said number is at least six; and detecting said incorporations after incorporation of one or more of said number of said nucleotides, thereby analyzing said number of bases of said sequence of said target polynucleotide. Methods also may be used in kits, said kits designed to carry out and facilitate the methods provided herein.

L. Polynucleotide Counting and Identification, and Applications Thereof

Some embodiments of the invention provide methods of enumerating a number of copies of a target polynucleotide by synthesizing a complementary stand, comprising: permitting random localization of said target polynucleotide on a surface of a substrate at an individually-addressable location; providing a labeled nucleotide, said nucleotide comprising a labeling moiety; allowing incorporation of said nucleotide into said complementary strand in the presence of a polymerizing agent; detecting incorporation; repeating said providing, said allowing, and said detecting steps a number of times sufficient to identify a copy of said target polynucleotide; and counting said identified copies, thereby enumerating said number of copies of said target polynucleotide. Methods also may be used in kits, said kits designed to carry out and facilitate the methods provided herein.

M. Surface Chemistry

Some embodiments of the invention provide methods of analyzing a sequence of a target polynucleotide by synthesizing a complementary strand, comprising: coating a surface of a substrate with a polyelectrolyte multilayer; permitting localization of said target polynucleotide on said surface of said substrate; providing a labeled nucleotide, said nucleotide comprising a labeling moiety; allowing incorporation of said nucleotide into said complementary strand in the presence of a polymerizing agent; and detecting incorporation, thereby analyzing said sequence of said target polynucleotide. Methods also may be used in kits, said kits designed to carry out and facilitate the methods provided herein.

Another aspect of the present invention provides a substrate comprising: a layer of polyanions; and a polynucleotide molecule anchored onto said layer of polyanions wherein said polynucleotide molecule is hindered from lying down on said layer.

N. Flow Cell

In another aspect, the invention provides apparatuses for carrying out the methods of the invention. Typically, apparatuses include:

(a) a flow cell which houses a substrate for immobilizing target polynucleotide(s) with single molecule resolution;

(b) an inlet port and an outlet port in fluid communication with the flow cell for flowing fluids into and through the flow cell;

(c) a light source for illuminating the surface of the substrate; and (d) a detection system for detecting a signal from said surface.

In another aspect of the present invention, apparatuses for analyzing the sequence of a polynucleotides are provided. Some of the apparatus are microfabricated. In some of these embodiments, the substrate is a microfabricated synthesis channel. Thus, the apparatuses may include:

(a) a flow cell with at least one micro-fabricated synthesis channel; and (b) an inlet port and an outlet port which are in fluid communication with the flow cell and which flow fluids and reagents, such as deoxynucleoside triphosphates and polymerase in to and through the flow cell.

In some embodiments of the invention, a light source for illuminating the surface of said substrate and a detection system for detecting a signal from said surface are employed. Thus, some of the apparatuses additionally include:

(c) a light source to direct light at a surface of the synthesis channel; and (d) a detector to detect a signal from the surface.

Optionally, an appropriately programmed computer is also employed for recording identity of a nucleotide when the nucleotide becomes incorporated into the immobilized primer or template.

In some embodiments, the synthesis channel is formed by bonding a microfluidic chip to a flat substrate. In some apparatuses, the microfluidic chip also contains micro-fabricated valves and micro-fabricated pumps in an integrated system with the synthesis channel. In some of these embodiments, a plurality of reservoirs for storing reaction reagents are also present, and the micro-fabricated valve and pump are connected to the reservoirs. In some embodiments, the detector is a photon counting camera. In some of the apparatuses, the microfluidic chip is fabricated with an elastomeric material such as RTV silicone. The substrate of some of the apparatuses is a glass cover slip. The cross section of the synthesis channel is some of the apparatuses has a linear dimension of less than about 100 µm×100 µm, less than about 10 µm×100 µm, less than about 1 µm×10 µm, or less than about 0.1 µm×1 µm.

In a further aspect, the present invention provides methods for analyzing the sequence of a target polynucleotide using such apparatuses, including the steps of:

(a) providing a primed target polynucleotide linked to a microfabricated synthesis channel;

(b) flowing a first nucleotide through the synthesis channel under conditions whereby the first nucleotide attaches to the primer, if a complementary nucleotide is present to serve as template in the target polynucleotide;

(c) determining presence or absence of a signal, the presence of a signal indicating that the first nucleotide was incorporated into the primer, and hence the identity of the complementary base that served as a template in the target polynucleotide;

(d) removing or reducing the signal, if present; and (e) repeating steps (b)-(d) with a further nucleotide that is the same or different from the first nucleotide, whereby the further nucleotide attaches to the primer or a nucleotide previously incorporated into the primer.

In some embodiments, step (a) comprises providing a plurality of different primed target polynucleotides linked to different synthesis channels; step (b) comprises flowing the first nucleotide through each of the synthesis channels; and step (c) comprises determining presence or absence of a signal in each of the channels, the presence of a signal in a synthesis channel indicating the first nucleotide was incorporated into the primer in the synthesis channel, and hence the identity of the complementary base that served as a template in the target polynucleotide in the synthesis channel. In some embodiments, a plurality of different primed target polynucleotides are linked to each of the synthesis channels.

Some embodiments include the further steps of flushing the synthesis channel to remove unincorporated nucleotides. In some methods, steps (b)-(d) are performed at least four times with four different types of nucleotides. In some methods, steps (b)-(d) are performed until the identity of each base in the target polynucleotide has been identified. In some of these embodiments, the removing or reducing step is performed by photobleaching. In some methods, all ingredients are present simultaneously, facilitating a continuous monitoring of the incorporation.

O. Single Molecule, Single Base Extension

Some embodiments of the invention provide methods for forming a spatially addressable array, which comprises determining the sequences of a plurality of polynucleotide molecules in an array that has a surface density such that a molecule in said array is in an optically resolvable area. Methods also may be used in kits, said kits designed to carry out and facilitate the methods provided herein.

A further understanding of the nature and advantages of the present invention may be realized by reference to the remaining portions of the specification, the figures and claims.

All publications, patents, and patent applications cited herein are hereby expressly incorporated by reference in their entirety and for all purposes to the same extent as if each was so individually denoted.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 shows schematically immobilization of a primed polynucleotide and incorporation of labeled nucleotides.

FIG. 4 shows results which indicate that DNA polymerase incorporating labeled nucleotide into the immobilized primer is visualized with single molecule resolution.

FIG. 19 illustrates the advantage of using short cycle sequencing with respect to avoiding long homopolymer reads.

FIG. 20 illustrates a short cycle embodiment for analyzing 200 target polynucleotides in a stimulated synthesis of their complementary strands using short-cycle periods of 0.8 half life periods and repeating the cycles 60 times.

FIG. 21 illustrates the statistics of incorporation, showing that polymerizing agent may incorporate repeat labeled nucleotides less readily than the first labeled nucleotide.

DETAILED DESCRIPTION OF THE INVENTION

I. Overview

Figure 1A:
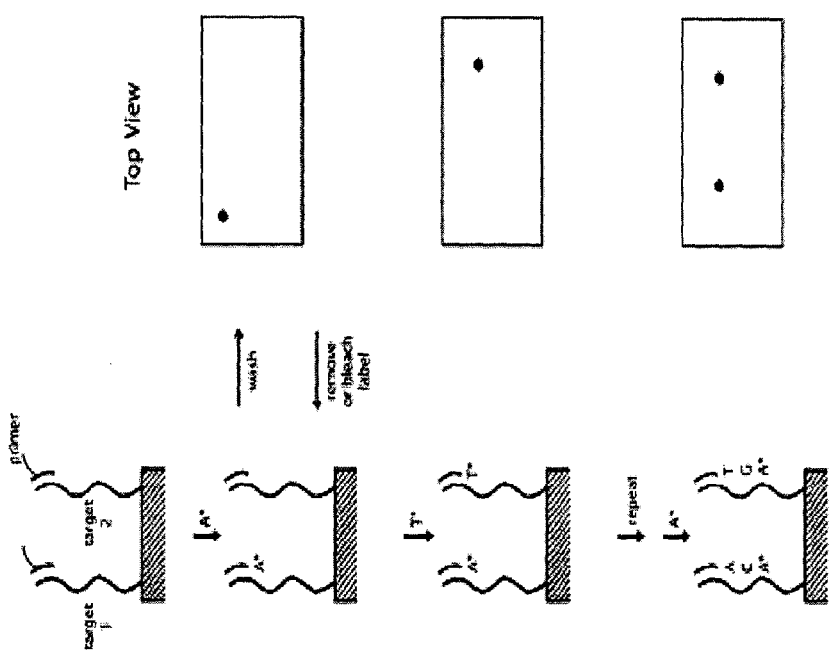
FIG. 1a is a schematic illustration and top field view of single molecule sequencing of a target polynucleotide.

The present invention provides methods and kits for analyzing one or more target polynucleotides with high sensitivity, parallelism, and long read frames. The analysis involves detecting incorporation of one or more nucleotides into the target's complementary strand in the presence of polymerizing agent, one or more types of nucleotides, and possibly other reaction reagents.

In some embodiments, methods for analyzing the sequence of a single target polynucleotide by single base extension are provided. Such embodiments can detect incorporation of a single nucleotide molecule into the complementary strand of a single target polynucleotide molecule. Such single molecule, single base extension embodiments can read a single target molecule individually, even where multiple copies of the same or different targets are analyzed in parallel.

In other embodiments, methods are applicable to sequencing by bulk single base extension. Such embodiments detect incorporation of nucleotides into a plural number of copies of a given target polynucleotide. That is, bulk single base extension embodiments read multiple copies of the same target, even where there are also multiple copies of different targets being analyzed in parallel.

In some embodiments of the present invention, the surface of a substrate is pretreated to create surface chemistry that facilitates polynucleotide attachment and subsequent sequence analysis. In some of these embodiments, the substrate surface is coated with a polyelectrolyte multilayer (PEM). Biotin can be applied to the PEM, followed by application of streptavidin. The substrate surface can then be used to attach biotinylated-templates. The PEM-coated substrate may provide substantial advantages for immobilizing polynucleotides and for polymerization reactions. First, PEM can easily be terminated with polymers bearing carboxylic acids, facilitating polynucleotide attachment. Second, the attached template is available for extension by polymerizing agents—most probably because repulsion of like charges between the negative carboxylic groups, for example, and the negative polynucleotide backbone hinders the template from "lying down" on the surface. Finally, the negative charges repel unincorporated nucleotides, reducing nonspecific binding and hence background interference.

Certain embodiments involve immobilizing target polynucleotides on the surface of a substrate (e.g., a glass or plastic slide, a nylon membrane, or gel matrix). The targets can be hybridized to a labeled primer (e.g., using a fluorescent dye) to form a target polynucleotide-primer complex, and their locations on the surface can be detected with single molecule sensitivity. In some aspects of the invention, single molecule resolution was achieved by anchoring the template molecules at low concentration to a surface of a substrate coated to create surface chemistry that facilitates template attachment and reduces background noise, and then imaging nucleotide incorporation, for example, with total internal reflection fluorescence microscopy.

In certain embodiments, the signals of already-incorporated nucleotides are removed, reduced, and/or neutralized after one or more rounds of incorporation. This may be achieved, for example, by photobleaching fluorescent signals, by chemical means, such as chemically bleaching the labeling moiety, and/or chemically or photo-chemically cleaving all or a portion of the labeling moiety, and/or by enzymatically cleaving all or a portion of the labeling moiety from the nucleotide. In some embodiments, extinguishing the labeling is not necessary after every extension cycle, reducing the number of cycle steps.

In certain embodiments, blocking moieties are used to hinder or halt the polymerization reaction. Removal of a portion or all of the blocking moiety reverses the inhibition, allowing chain elongation to resume. Such an approach makes it possible to read long runs of identical bases that may not be quantifiable due to increasing signal intensity. Another approach to reading homopolymer stretches involves uses short cycle times, wherein only a limited number of nucleotides are allowed to incorporate in the growing complementary strands during each cycle.

Certain embodiments use a labeling moiety that is sufficiently large to prevent or hinder further chain elongation by "choking" the polymerizing agent, thereby halting chain elongation without a 3' blocking group. Subsequent removal of the labeling moiety, or at least the steric-hindering portion of the moiety, can concomitantly reverse chain termination and allow chain elongation to proceed.

Some embodiments use separate labeling and blocking moieties, but still allow single step reversal of chain termination and reduction of incorporated signals. In such embodiments, for example, chemically cleaving or photo-cleaving the blocking moiety may also chemically-bleach or photo-bleach the labeling moiety, respectively.

In some other embodiments of the present invention, for example, in bulk single base extension embodiments, only a small percentage of each type of nucleotides present in the extension reaction is labeled, e.g., with fluorescent dye. As a result, relatively small numbers of incorporated nucleotides are fluorescently labeled, interference of energy transfer is minimized, and the polymerizing agent is less likely to fall off the template or be "choked" by incorporation of two labeled nucleotides sequentially. This may provide more efficient consumption of polymerizing agent. In other embodiments, on the other hand, inefficient incorporation is desirable. For example, stopping or stalling incorporation by choking may be desired. Also, inefficient incorporation may lead to longer half lives for the slowed down incorporation, which is desirable in some short cycle sequencing embodiments.

Analysis with single molecule resolution provides the advantage of monitoring the individual properties of different molecules. As each of the immobilized template molecules can be read individually, no synchronization is needed between the different molecules. Instead, with methods of the present invention, asynchronous base extension is sufficient for analyzing a target polynucleotide sequence. This allows identification of properties of an individual molecule that can not be revealed by bulk measurements in which a large number of molecules are measured together. For example, to determine kinetics, bulk measurements require synchronization, whereas in single molecule analysis there is no such need. Further, asynchronous analysis allows for short cycles, that can facilitate analysis of homopolymer stretches, as mentioned above.

The polynucleotides suitable for analysis with the invention can be DNA or RNA, as defined below. The analysis can provide sequence analysis, DNA fingerprinting, polymorphism identification, for example single nucleotide polymorphisms (SNP) detection, as well as methods for genetic cancer research. Applied to RNA sequences, the analysis can also identify alternate splice sites, enumerate copy number, measure gene expression, identify unknown RNA molecules present in cells at low copy number, annotate genomes by determining which sequences are actually transcribed, determine phylogenic relationships, elucidate differentiation of cells, and facilitate tissue engineering. The methods can also be used to analyze activities of other biomacromolecules such as RNA translation and protein assembly. Certain aspects of the present invention lead to more sensitive detection of incorporated signals and faster sequencing, lending themselves to these applications.

In certain embodiments, the sequencing apparatuses comprise a microfabricated flow channel to which polynucleotide templates are attached. Optionally, the apparatuses comprise a plurality of microfabricated channels, and diverse polynucleotide templates can be attached to each channel. The apparatuses can also have a plurality of reservoirs for storing various reaction reagents, and pumps and valves for controlling flow of the reagents. The flow cell can also have a window to allow optical interrogation.

In some embodiments, single stranded polynucleotide templates with primers are immobilized to the surface of the microfabricated channel or to the surface of reaction chambers that are disposed along a microfabricated flow channel, e.g., with streptavidin-biotin links. After immobilization of the templates, a polymerizing agent and one or more of the four nucleotide triphosphates are flowed into the flow cell, incubated with the template, and flowed out. If no signal is detected, the process is repeated with one or more different types of nucleotides.

The use of microfabricated sequencing apparatuses can reduce reagent consumption. It also increases reagent exchange rate and the speed of sequence analysis. Indeed, using a microfluidic device, the rate at which the concentrations can be alternated can be as high as a few tens of Hertz. Additionally, the reduction of time and dead volume for exchanging reagents between different steps can also greatly reduce mismatch incorporation. Moreover, the read length can also be improved because there is less time for the polymerizing agent to incorporate a wrong nucleotide and it is less likely to fall off the template. All these advantages can result in high speed and high throughput sequence analysis regimes.

Alternating concentrations of nucleotides can also improve signal visualization and polymerization rate in the static approach of sequence analysis. In this approach, after adding a given type of labeled nucleotide to the immobilized target polynucleotide-primer complex and allowing sufficient time for incorporation, free nucleotides (as well as other reaction reagents in solution) can be flushed out using a microfluidic device. This will leave a much lower concentration of free nucleotides when detecting incorporated signals. Optionally, an additional washing step can be employed to further reduce the free nucleotide concentration before detecting the signals.

Further, in using a microfluidic device which allows fast fluid exchange, concentrations of nucleotides and/or other reaction reagents can be alternated at different time points of the analysis. This could lead to increased incorporation rates and sensitivity. For example, when all four types of nucleotides are simultaneously present in the reaction to monitor dynamic incorporation of nucleotides, concentrations of the nucleotides can be alternated between µM range and sub-nM range. This leads to both better visualization of the signals when low concentrations of nucleotides are present, and increased polymerization rate when higher concentrations of nucleotides are present.

Certain embodiments of the present invention avoid many of the problems observed with other sequencing methods. For example, the methods are highly parallel since many molecules can be analyzed simultaneously at high density (e.g., one template molecule per≈10 µm$^2$ of surface area, as well as about 1 or 2 million per cm$^2$). Thus, many different polynucleotides can be sequenced or analyzed on a single substrate surface simultaneously. The microfabricated apparatuses facilitate this parallelization in that many synthesis channels can be built on the same substrate, allowing analysis of a plurality of diverse polynucleotide sequences simultaneously.

II. Target Polynucleotide Preparation

The present invention provides methods and kits for analyzing the sequence of a target polypeptide by detecting incorporation of a nucleotide into its complementary strand. Preparation for this analysis may include obtaining the target from a source and hybridizing it to a primer.

A. Target Polynucleotide Sources

The target polynucleotide is not critical and can come from a variety of standard sources. For example, nucleic acids can be naturally occurring DNA or RNA isolated from any source, recombinant molecules, cDNA, or synthetic analogs, as known in the art. For example, the target polynucleotides may be genomic DNA, genes, gene fragments, exons, introns, regulatory elements (such as promoters, enhancers, initiation and termination regions, expression regulatory factors, expression controls, and other control regions), DNA comprising one or more single-nucleotide polymorphisms (SNPs), allelic variants, and other mutations. Also included are the full genome of one or more cells, for example cells from different stages of diseases such as cancer. The target polynucleotide may also be mRNA, tRNA, rRNA, ribozymes, splice variants, antisense RNA, and RNAi. Also included are RNA with a recognition site for binding a polymerizing agent, transcripts of a single cell, organelle or microorganism, and all or portions of RNA complements of one or more cells, for example, cells from different stages of development or differentiation, and cells from different species. Polynucleotide can be obtained from any cell of a person, animal, plant, bacteria, or virus, including pathogenic microbes or other cellular organisms.

Templates suitable for analysis according to the present invention can have various sizes. For example, the template can have a length of about 10 bases, about 20 bases, about 30 bases, about 40 bases, about 50 bases, about 60 bases, about 70 bases, about 80 bases, 90 bases, 100 bases, about 200 bases, about 500 bases, about 1 kb, about 3 kb, about 10 kb, or about 20 kb and so on.

When the target is from a biological source, a variety of known procedures may be used for extracting the polynucleotide and optionally amplifying to a concentration convenient for genotyping or sequence work. Recombinant or synthetic polynucleotides may also be amplified. Polynucleotide amplification methods are known in the art. Preferably, the amplification is carried out by polymerase chain reaction (PCR). See, U.S. Pat. Nos. 4,683,202. 4,683,195 and 4,889,818; Gyllenstein et al., 1988, Proc. Natl. Acad. Sci. USA 85: 7652-7656; Ochman et al., 1988, Genetics 120: 621-623; Loh et al., 1989, Science 243: 217-220; Innis et al., 1990, PCR Protocols, Academic Press, Inc., San Diego, Calif. Other amplification methods known in the art that can be used in the present invention include ligase chain reaction (see EP 320, 308), or methods disclosed in Kricka et al., 1995, Molecular Probing, Blotting, and Sequencing, Chap. 1 and Table IX, Academic Press, New York.

In some applications, the polynucleotides to be analyzed are first cloned in single-stranded M1 3 plasmid (see, e.g., Cur-rent Protocols In Molecular Biology, Ausubel, et al., eds., John Wiley & Sons, Inc. 1995; and Sambrook, et al., Molecular Cloning. A Laboratory Manual, Cold Spring Harbor Press, 1989). The single stranded plasmid can be primed by 5'-biotinylated primers (see, e.g., U.S. Pat. No. 5,484,701), and double stranded plasmid can then be synthesized. The double stranded circle can then be linearized, and the biotinylated strand purified.

B. Primer Hybridization

Analyzing a target polynucleotide by synthesizing its complementary strand may involve hybridizing an oligonucleotide primer to the target. The primer can be selected to be sufficiently long to prime the synthesis of extension products in the presence of a polymerizing agent. Primer length can be selected to facilitate hybridization to a sufficiently complementary region of the template polynucleotide downstream of the region to be analyzed. The exact lengths of the primers depend on many factors, including temperature, source of primer and the use of the method. For example, primers may be at least about 10 bases in length, at least about 15, or at least about 30 bases in length.

If part of the region downstream of the sequence to be analyzed is known, a specific primer can be constructed and hybridized to this region of the template. Alternatively, if sequences of the downstream region on the template polynucleotide are not known, universal or random primers may be used in random primer combinations. As another approach, oligonucleotide adaptors can be joined to the ends of target polynucleotide by a ligase and primers can be designed to bind to these adaptors. That is, an adaptor or linker can be ligated to target polynucleotides of unknown sequence to allow for primer hybridization. Alternatively, known sequences may be biotinylated and ligated to the targets. In yet another approach, nucleic acid may be digested with a restriction endonuclease, and primers designed to hybridize with the known restriction sites that define the ends of the fragments produced.

The primers can be synthetically made using conventional nucleic acid synthesis technology. For example, primers can be conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. as disclosed in Beaucage and Iyer, Tetrahedron, 48: 2223-2311 (1992), and the like. Alternative chemistries, e.g. resulting in non-natural backbone groups, such as phosphorothioate, phosphoramidate, and the like, may also be employed provided that, for example, the resulting oligonucleotides are compatible with the polymerizing agent. The primers can also be ordered commercially from a variety of companies which specialize in custom oligonucleotides such as Operon Inc (Alameda, Calif.).

In some embodiments, the primer bears a labeling moiety. When hybridized to an anchored polynucleotide molecule, the labeling moiety facilitates locating the bound molecule through imaging. As exemplified in the Examples below, the primer can be labeled with a fluorescent labeling moiety (e.g., Cy5), or any other means used to label nucleotides. The labeling moiety used to label the primer can be different from the labeling moieties used on the nucleotides in the subsequent polymerization reactions. Correlation of the signal of the different types of labeling moieties can also facilitate locating bound molecules as well as locating bound molecules capable of acting as useful templates for complementary strand synthesis.

If the target polynucleotide-primer complex is to be anchored on a surface of a substrate, the primer can be hybridized before or after such anchoring. Primer annealing can be performed under conditions which are stringent enough to require sufficient sequence specificity, yet permissive enough to allow formation of stable hybrids at an acceptable rate. The temperature and time required for primer annealing depend upon several factors including base composition, length, and concentration of the primer; the nature of the solvent used, e.g., the concentration of DMSO, formamide, or glycerol; as well as the concentrations of counter ions, such as magnesium. Typically, hybridization with synthetic polynucleotides is carried out at a temperature that is approximately 5 to approximately 10° C. below the melting temperature (Tm) of the target polynucleotide-primer complex in the annealing solvent. In some embodiments, the annealing temperature is in the range of about 55 to about 75° C. and the primer concentration is approximately 0.2 μM. Other conditions of primer annealing are provided in the Examples below. In certain embodiments, the annealing reaction can be complete within a few seconds.

III. Surface Treatment and Polynucleotide Anchoring

A. Treatment of Substrate Surface

The surface chemistry created by methods described herein provides various advantages to carrying out the present invention. In some applications, for example, the surface of the substrate (or synthesis channel) is pretreated to create surface chemistry that facilitates high density polynucleotide attachment with single molecule resolution, where the polynucleotide molecules are available for subsequent synthesis reactions. Coating the substrate (e.g., a microchannel) surface with the PEM and other techniques described herein can be significant for analyzing polynucleotide sequences according to the present invention.

For example, certain embodiments of the present invention feature a substrate coated with at least one layer of polyanions to which a polynucleotide molecule is anchored, where the polynucleotide molecule is hindered form lying down on the layer. The electrostatic repulsion between the negatively-charged polynucleotide backbone and the negatively-charged anionic layer helps keep the polynucleotide molecule in a substantially upright position relative to the layer. In some embodiments, the surface is thus exposed to a negative layer and a polynucleotide molecule anchored thereto.

In some embodiments, multiple layers of alternating positive and negative charges are used. In the case of incompletely-charged surfaces, multiple-layer deposition tends to increase surface charge to a well-defined and stable level.

In some embodiments, for example, the surface is coated with a polyelectrolyte multilayer (PEM). In some methods, PEM based surface chemistry can be created prior to template or primer attachment. Preferably, the substrate surface is coated with a polyelectrolyte multilayer (PEM). Attachment of templates and/or primers to PEM-coated surface can be accomplished by light-directed spatial attachment (see, e.g., U.S. Pat. Nos. 5,599,695, 5,831,070, and 5,959,837). Alternatively, the templates and/or primers can be attached to PEM-coated surface entirely chemically. In some embodiments, non-PEM based surface chemistry can be created prior to template and/or primer attachment.

PEM formation has been described in Decher et al. (Thin Solid Films, 210:831-835, 1992). PEM formation proceeds by the sequential addition of polycations and polyanions, which are polymers with many positive or negative charges, respectively. Upon addition of a polycation to a negatively-charged surface, the polycation deposits on the surface, forming a thin polymer layer and reversing the surface charge. Similarly, a polyanion deposited on a positively charged surface forms a thin layer of polymer and leaves a negatively charged surface. Alternating exposure to poly(+) and poly(−) generates a polyelectrolyte multilayer structure with a surface charge determined by the last polyelectrolyte added. This can produce a strongly-negatively-charged surface, repelling the negatively-charged nucleotides and preventing lying down.

In certain embodiments, for example, methods of preventing a substrate-anchored polynucleotide from lying down on the substrate involve exposing the substrate to a positive or negative polyelectrolyte, washing, exposing the substrate a polyelectrolyte of opposite charge from the one previously used, repeating the alternating layers any number of times, and terminating with a layer of negative polyelectrolyte. Each polyelectrolyte step can be, e.g. about 10 minutes, and a wash step can be carried out by thorough rinsing with high purity water. The negative polyelectrolyte may be a polystyrene sulphonate polymer, a polyglutamic acid polymer and/or a polyacrylic acid polymer. The positive polyelectrolyte may be a polylysine polymer, a polyethyleneimine polymer and/or a poly(allylamine) polymer. The number of alternating layers may be about two, about three, about four, about five, about six, and so on.

Further, an upright orientation helps the anchored polynucleotide remain available for polymerizing reactions, serving as a useful template for a polymerizing agent synthesizing the complementary strand. That is, the attached template can be read by polymerizing agents—most probably because the repulsion of like charges hinders the template in lying down on the surface. Without being bound to any particular theory, the negative electrostatic shielding at the surface probably repels the unanchored end of the polynucleotide molecule away from the surface, reducing surface-promoted denaturation of the polymerizing agent and/or reducing steric hindrances that might inhibit polymerizing activity.

Binding large quantities of polynucleotides may not be useful if the target polynucleotide-primer complex cannot be extended by a polymerizing agent. For example, this problem may arise from surface chemistry bearing amines, which are positively charged at normal pH. The negatively-charged polynucleotide backbone can non-specifically stick to such a surface, sterically impeding the polymerizing agent from adding nucleotides. Some embodiments avoid such problems by coating a substrate with a PEM and anchoring a polynucleotide molecule to it to allow nucleotide incorporation into its complementary strand in the presence of a polymerizing agent.

An upright orientation also facilitates detection, e.g. detection of a fluorescent moiety incorporated into the growing complementary strand. Detection is also facilitated by reduction of background signals. That is, in certain embodiments, surface chemistry reduces background by reducing non-specific attachment of free labeled nucleotides to the surface of the substrate. For example, it can render nonspecific binding of fluorescently-labeled nucleotides very low, because negative charges of the terminal surface layer can repel negatively-charged free nucleotides bearing fluorescent moieties. In certain embodiments, the substrate bears a layer of polyanions sufficient to reduce nonspecific attachment of negative moieties by a factor of at least about 5, at least about 6, at least about 7, at least about 8, at least about 9, at least about 10, at least about 11, at least about 12, at least about 13, at least about 14, and at least about 15 compared to an uncoated surface of the substrate. This can achieve low density of non-specifically attached nucleotide molecules. Further, the polymeric nature of the PEM can result in increased charge density for each depositing layer, facilitating fine tuning of the charge density and covering any inhomogeneities on the surface that may become sites for non-specific attachment.

If there is significant nonspecific binding of nucleotides bearing fluorescent moieties to the surface, it may become impossible to distinguish between signal due to incorporation and signal due to nonspecific binding. Fluorescently-labeled nucleotides generally exhibit relatively strong nonspecific binding to many surfaces, because they can possess both a strongly polar moiety (the nucleotide, and in particular any triphosphate) and a relatively-hydrophobic moiety (e.g., the fluorescent dye). A surface bearing positively-charged groups (e.g., amines) can promote very high nonspecific binding due to the attraction of the negatively charged nucleotides to the positively-charged surface groups, e.g., amines. Neutral surfaces generally also exhibit strong nonspecific binding due to the fluorescently-labelled nucleotide acting as a surfactant (i.e. assembling with its nonpolar moiety directed towards the uncharged (more hydrophobic) surface and its polar end directed towards the aqueous phase. Glass is a negatively-charged surface in water, but the surface silanols that create teh negative charge are a difficult target for directly attaching polynucleotides. Typical attachment protocols use silanization (often with aminosilanes); however, as discussed above, amino groups can lead to unacceptable levels of nonspecific binding. Using the surface chemistries described herein, however, can facilitate methods of detecting synthesis of a single polynucleotide molecule, for example, by coating a substrate with a PEM, anchoring the polynucleotide molecule to the PEM at single molecule resolution, and detecting incorporation of a nucleotide bearing a labeling moiety.

In certain embodiments, the polynucleotide molecule that serves as a template for polymerization is selected to be of a certain length and anchored to the surface of the substrate. Longer length templates further facilitate detection of incorporated fluorescently-labeled nucleotides, as the incorporated fluorescent moieties are held away from the surface. For example, using a polynucleotide template of a certain length attached to a surface bearing a negatively-charged layer, a single molecule of a fluorescently-labeled nucleotide can be detected when it becomes hybridized to the template or incorporated into its complementary strand. The single molecule can be detected over background fluorescence from unincorporated fluorescently-labeled nucleotide molecules. The polynucleotide template used may be at least about 30 nucleotide residues, at least about 40 nucleotide residues, at least about 50 nucleotide residues, at least about 60 nucleotide residues, at least about 70 nucleotide residues, at least about 80 nucleotide residues, and at least about 90 nucleotide residues. The polynucleotide template used may be covalently or non-covalently attached to the surface, e.g. by biotin-steptavidin coupling.

Figure 16:
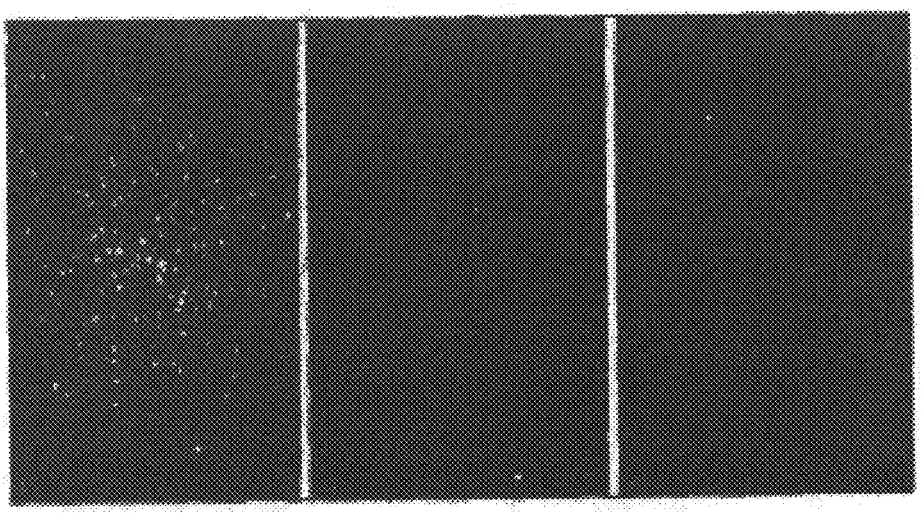
FIG. 16 illustrates on-surface incorporation into bound DNA being visualized at the single-DNA level.

FIG. 16 illustrates on-surface incorporation in anchored DNA being visualized at the single-DNA level. FIG. 16a illustrates points of incorporation of fluorescently-labeled nucleotide in the presence of a DNA polymerase. FIG. 16b illustrates the result where no polymerizing agent is present and FIG. 16c illustrates the result where both fluorescently-labeled nucleotides and polymerizing agent are withheld. Comparison of FIG. 16a with the controls 16b-c indicates that over 95% of the observed objects in FIG. 16a represent single molecules of DNA.

Where more than one nucleotide of the same base-type becomes incorporated into the growing complementary strand, the number of nucleotides incorporated may by determined by quantifying the intensity of signal from labeling moieties on the incorporated nucleotides. Reduction of background signal, e.g., from unincorporated fluorescently-labeled nucleotides, also facilitates this quantification. For example, a polynucleotide template of a certain length can be attached to a surface bearing a negatively-charged layer and fluorescence from a number of bound fluorescently-labeled nucleotides measured over background interference from unbound fluorescently-labeled nucleotides, so that the measurement quantifies the number of bound nucleotide residues. Such embodiments can allow quantification of a number of repeat bases, that is, consecutive nucleotide residues each bearing the same base-type, e.g. in a homopolymer stretch. The number of repeat bases may be about two, about three, about 4, about 5, about 6, about 7, and about 8. As mentioned before, the polynucleotide template used may be at least about 30 nucleotide residues, at least about 40 nucleotide residues, at least about 50 nucleotide residues, at least about 60 nucleotide residues, at least about 70 nucleotide residues, at least about 80 nucleotide residues, and at least about 90 nucleotide residues; and may be covalently or non-covalently attached to the surface, e.g. by biotin-steptavidin coupling.

Surface chemistries of the present invention can also facilitate anchoring reasonable quantities of polynucleotide at high surface density. The terminal negative layer may bear groups that facilitate attachment of polynucleotide molecules, for example by covalent linkage between the group and the polynucleotide molecule. Carboxylic acids, for example, are good targets for covalent bond formation. In some embodiments, a binding pair may be used, where the terminal layer bears one member of the pair, and the polynucleotides bear the other. For example, biotin may be coupled to the terminal layer of the substrate surface to facilitate anchoring using biotin-streptavidin binding pairs. Such treatment allows a high density of polynucleotide coverage with single molecule resolution as described in more detail below.

In certain embodiments, surface chemistries of the present invention can be used to create an array comprising a substrate, a PEM coating the substrate, and polynucleotide molecules anchored to the substrate at a density allowing visualization of the individual polynucleotide molecules. If insufficient numbers of template molecules were to be bound, the signal-to-noise ratio might become too low to allow useful sequencing. In some embodiments, the polynucleotide molecules are at a density of at least about 0.1, at least about 0.2, at least about 0.3, at least about 0.4, at least about 0.5, at least about 0.6, at least about 0.7, at least about 0.8, at least about 0.9, and at least about 1 polynucleotide molecule per $\mu m^2$.

Detailed procedures for coating a substrate with PEM for immobilizing polynucleotide are described in the Examples below. Briefly, the surface of the substrate (e.g., a glass cover slip) can be cleaned with a RCA solution. After cleaning, the substrate can be coated with a polyelectrolyte multilayer (PEM), terminating with carboxylic acid groups. Following biotinylation of the carboxylic acid groups, streptavidin can be applied to generate a surface capable of capturing biotinylated molecules. Biotinylated polynucleotide templates or primers can then be added to the coated substrate for anchoring. During the anchoring step, a high concentration of cations, e.g., $Mg^{2+}$, can be used to screen the electrostatic repulsion between the negatively-charged polynucleotides and the negatively-charged PEM surface. In subsequent steps, the cation concentration can be reduced to re-activate repulsive shielding. By titrating biotinylated polynucleotide molecules, it is possible to bind such a small number of molecules to the surface that they are separated by more than the diffraction limit of optical instruments and thus able to be visualized individually.

The attachment scheme described here can be readily generalized. Without modification, the PEM/biotin/streptavidin surface produced can be used to capture or immobilize any biotinylated molecule. A slight modification can be the use of another capture pair, for example, substituting digoxygenin (dig) for biotin and labeling the molecule to be anchored with anti-digoxygenin (anti-dig). Reagents for biotinylation or dig-labeling of amines are both commercially available.

The fact that the chemistry is nearly independent of the surface chemistry of the support permits further generalization. Glass, for instance, can support PEMs terminated with either positive or negative polymers, and a wide variety of chemistry is available for either. But other substrates such as silicone, polystyrene, polycarbonate, etc, or even membranes and/or gels, which are not as strongly charged as glass, can still support PEMs. The charge of the final layer of PEMs on weakly-charged surfaces becomes as high as that of PEMs on strongly-charged surfaces, as long as the PEM has sufficiently-many layers. For example, PEM formation on $O_2$-plasma treated silicone rubber has been demonstrated by the present inventors. Thus, advantages of the glass/PEM/biotin/Streptavidin/biotin-polynucleotide surface chemistry can readily be applied to other substrates.

In microfluidic embodiments, the attachment schemes can be either ex-situ or in-situ. With the ex-situ protocol, for example, the surface of the substrate is coated with PEM first, followed by template/primer attachment. An elastomeric microfluidic chip is then bonded to the substrate to form and seal the synthesis channel. With the in-situ protocol, on the other hand, the microfluidic chip is attached to the flat substrate first, and a PEM is then constructed within the channels. The templates/primers are then attached inside the channels. In still other embodiments, the microfluidic chip can be bonded to the substrate at any point in the template/primer attachment process, and the remaining steps can be completed inside the microfluidic channels.

Certain embodiment described herein lead to good seal of the microfluidic components and the synthesis channels. A good seal between the microfluidic components and the synthesis channels allows the use of higher pressures, which in turn increases flow rates and decreases exchange times.

Although the above discussion describes the immobilization of polynucleotide templates or primers by attachment to the surface of flow channels (or the surface of reaction chambers disposed along flow channels), other methods of template immobilization can also be employed in certain embodiments of the present invention. In some embodiments, for example, the templates or primers can be attached to microbeads, which can be arranged within the microfluidic system. For instance, commercially-available latex microspheres with pre-defined surface chemistry can be used. The polynucleotide templates or primers can be attached either before or after the microbeads are inducted into the microfluidic system. Attachment of template or primer before beads are added may allow a reduction in system complexity and setup time (as many templates or primers can be attached to different aliquots of beads simultaneously). Attachment of template or primer to beads in situ can allow easier manipulation of surface chemistry (as bead surface chemistry can be manipulated in bulk, externally to the microfluidic device). Beads can be held in place within the flow system, for example, by flowing the beads into orifices too small for them to flow through (where they become "wedged in"), creating "microscreens" (i.e. barriers in the channel with apertures too small for beads to pass through), and inserting the beads into hollows in the channels where they are affixed by simple Van der Waals forces.

B. Polynucleotide Anchoring

In some embodiments, the template or target polynucleotide molecules are provided as single molecule arrays anchored to the surface of a substrate. The substrate can be a solid support (e.g., glass, silica, or plastic), a semi-solid support (e.g., a gel or other matrix), and/or a porous support (e.g., a nylon membrane or other membrane) or any other conventionally non-reactive material. In some embodiments, the substrate is selected to not create significant noise or background for fluorescent detection methods. The substrate surface to which targe polynucleotides are to be anchored can also be the internal surface of a flow cell in a microfluidic apparatus, e.g., a microfabricated synthesis channel. By anchoring the templates, unincorporated nucleotides can be removed from the synthesis channels by a washing step. In some embodiments, the substrate is made from fused silica slide (e.g., a fused silica glass slide from Esco, Cat. R130110). Compared to some other substrate materials (e.g., a regular glass slide), fused silica has very low auto-fluorescence, that may be desirable in certain embodiments.

In some applications of the present invention, the polynucleotides are anchored or immobilized to the substrate surface with single molecule resolution. In such methods, as exemplified in the Examples below, single molecule resolution is achieved by using very low concentration of the polynucleotide in the immobilization reaction. For example, a 10 pM concentration for a 80-mer polynucleotide template allows attachment of the polynucleotide to the surface of a silica slide at single molecule resolution (see Example 1). Template immobilization with single molecule resolution can also be verified by measuring bleach pattern of fluorescently-labeled templates (see Example 5).

In some embodiments, the target polynucleotides are immobilized to the surface prior to hybridization to the primer. In certain embodiments, the target polynucleotides are hybridized to the primers first and then immobilized on the surface. In still some embodiments, the primers are immobilized to the surface, and the target polynucleotides are attached to the substrates through hybridization with the primers. In some embodiments, the primer is hybridized to target polynucleotide prior to providing nucleotides for the polymerization reaction. In some, the primer is hybridized to the target polynucleotide while the nucleotides are being provided. In still some embodiments, the polymerizing agent is immobilized to the surface.

Various methods can be used to anchor or immobilize the target polynucleotides or the primers to the surface of the substrate, such as, the surface of the synthesis channels or reaction chambers. The immobilization can be achieved through direct or indirect bonding to the surface. The bonding can be by covalent linkage. See, Joos et al., Analytical Biochemistry 247:96-101, 1997; Oroskar et al., Clin. Chem 42:1547-1555, 1996; and Khandjian, Mole. Bio. Rep. 11: 107-115, 1986. The bonding can also be through non-covalent linkage. For example, Biotin-streptavidin (Taylor et al., J. Phys. D. Appl. Phys. 24:1443, 1991) and digoxigenin with anti-digoxigenin (Smith et al., Science 253: 1122, 1992) are common tools for anchoring polynucleotides to surfaces and parallels. Alternatively, the attachment can be achieved by anchoring a hydrophobic chain into a lipidic monolayer or bilayer. Other methods for attaching nucleic acids to supports can also be used.

When biotin-streptavidin linkage is used to anchor the polynucleotides, the polynucleotides can be biotinylated, while one surface of the substrates (e.g., one surface of the synthesis channels) can be coated with streptavidin. Since streptavidin is a tetramer, it has four biotin binding sites per molecule. Thus, it can provide linkage between the surface and the polynucleotide. In order to coat a surface with streptavidin, the surface can be biotinylated first, and then one of the four binding sites of streptavidin can be used to anchor the protein to the surface, leaving the other sites free to bind the biotinylated polynucleotide (see, Taylor et al., J. Phys. D. Appl Phys. 24:1443, 1991). Such treatment leads to a high density of streptavidin on the surface of the substrate (e.g. the synthesis channel), allowing a correspondingly high density of template coverage. Surface density of the polynucleotide molecules can be controlled by adjusting the concentration of the polynucleotide applied to the surface. Reagents for biotinylating a surface can be obtained, for example, from Vector laboratories. Alternatively, biotinylation can be performed with BLCPA: EZ-Link Biotin LC-PEO-Amine (Pierce, Cat. 21347), or any other known or convenient method.

In some embodiment, labeled streptavidin (e.g., streptavidin bearing a labeling moiety such as a fluorescent label) of very low concentration (e.g., in the µM, nM or pM range) is used to coat the substrate surface prior to anchoring. This can facilitate immobilization of the polynucleotide with single molecule resolution. It also can allow detecting spots on the substrate to determine where the polynucleotide molecules are attached, and to monitor subsequent nucleotide incorporation events.

While diverse polynucleotide templates can be each immobilized to and sequenced in a separate substrate or in a separate synthesis channel, multiple templates can also be analyzed on a single substrate (e.g. in a single microfluidic synthesis channel). In the latter scenario, the templates can be bound to different locations on the substrate (e.g. at different locations along the flow path of the channel). This can be accomplished by a variety of different methods, including hybridization of primer capture sequences to oligonucleotides immobilized at different points on the substrate (e.g. the channel), and sequential activation of different points down the substrate (e.g. the channel) towards template immobilization.

Methods of creating surfaces with arrays of oligonucleotides have been described, e.g., in U.S. Pat. Nos. 5,744,305, 5,837,832, and 6,077,674. In certain embodiments, such surfaces can be used as a substrate to be bonded to a microfluidic chip to form a synthesis channel. Primers with two domains, a priming domain and a capture domain, can be used to anchor polynucleotide targets to the substrate. The priming domain is complementary to a region of the target polynucleotide. The capture domain is present on the non-extended side of the priming sequence. It is not complementary to the target template, but rather to a specific oligonucleotide sequence present on the substrate. The target polynucleotide can be separately hybridized with their primers, or (if the priming sequences are different) hybridized together in the same solution. Incubation of the target polynucleotide-primer complexes with the substrate (e.g., in the flow channel) under hybridization conditions allows attachment of each to a unique spot. Multiple substrates (e.g., multiple synthesis channels) can be charged with polynucleotides in this fashion simultaneously.

Another method for attaching multiple polynucleotides to the surface of a single substrate (e.g. in a single channel) is to sequentially activate portions of the substrate and attach template to them. Activation of the substrate can be achieved by either optical or electrical means. Optical illumination can be used to initiate a photochemical deprotection reaction that allows attachment of the polynucleotide molecule to the surface (see, e.g., U.S. Pat. Nos. 5,599,695, 5,831,070, and 5,959,837). For instance, the substrate surface can be derivitized with "caged biotin", a commercially available derivative of biotin that becomes capable of binding to avidin only after being exposed to light. Polynucleotides can then be attached by exposure of a site to light, filling the channel with avidin solution, washing, and then flowing biotinylated template into the channel. Another variation is to prepare avidinylated substrate and a target polynucleotide with a primer with a caged biotin moiety; the target polynucleotide can then be anchored by flowing into the channel, while illuminating the solution above a desired area. Activated target polynucleotide-primer complexes are then attached to the first wall they diffuse to, yielding a diffusion-limited spot.

Electrical means can also be used to direct polynucleotide molecules to specific locations on a substrate or in a channel. By positively charging one electrode in the channel and negatively charging the others, a field gradient can be created which drives the polynucleotide molecule to a single electrode, where it can attach (see, e.g., U.S. Pat. Nos. 5,632,957, 6,051,380, and 6,071,394). Alternatively, it can be achieved by electrochemically activating regions of the surface and changing the voltage applied to the electrodes. Patterning of particular chemicals, include proteins and polynucleotides is possible with a stamp method, in which a microfabricated plastic stamp is pressed on the surface (see, e.g., Lopez et al., J. Amer. Chem. Soc. 115:10774-81, 1993).

In certain embodiments, different polynucleotides can also be attached to the surface randomly as the reading of each individual molecule may be analyzed independently from the others. Any other known methods for attaching polynucleotides and/or proteins may be used.

IV. Complementary Strand Synthesis

After preparing the target polypeptide and possibly anchoring it on the surface of a substrate, primer extension reactions can be performed (e.g., as described in Sambrook, supra; Ausubel, supra; and Hyman, Anal. Biochem., 174, p. 423, 1988) to analyze the target polynucleotide sequence by synthesizing its complementary strand. In some embodiments, the primer is extended by a polymerizing agent in the presence of a single type of nucleotide bearing a labeling moiety. In other embodiments, all four types of nucleotides are present, each bearing a detectably distinguishable labeling moiety. In some applications of the present invention, a combination of labeled and non-labeled nucleotides are used in the analysis.

A labeling moiety can be incorporated into the target polynucleotide-primer complex when the specific nucleotide bearing the labeling moiety is complementary to the nucleotide on the template adjacent to the 3' end of the primer. Optionally, the target polynucleotide-primer complex is subsequently washed to remove unincorporated labeling moieties, and the presence of any incorporated labeling moiety is detected. Reaction conditions and incubation times may be chosen to reduce polymerization errors.

A. Polymerizing Agents

Various polymerizing agents can be selected for use in this invention. For example, depending on the template, a DNA polymerase, an RNA polymerase, or a reverse transcriptase can be used in the primer extension reactions. For analysis of DNA templates, many DNA polymerases are available. Examples include, but are not limited to, *E. coli* DNA polymerase, Sequenase 2.0®, T4 DNA polymerase or the Klenow fragment of DNA polymerase 1, T3, AMV, M-MLV, and/or Vent polymerase. In some embodiments, polymerases which lack 3'→5' exonuclease activity can be used (e.g., T7 DNA polymerase (Amersham) or Klenow—exo fragment of DNA polymerase I (New England Biolabs)). In other embodiments, when it is desired that the polymerase have proofreading activity, polymerases lacking 3'→5' exonuclease activity would not be used.

Rather than thermodegradable polymerizing agents, in some embodiments, thermostable polymerases are used, such as ThermoSequenase™ (Amersham) or Taquenase™ (ScienTech, St Louis, Mo.). Further examples include other thermostable polymerases isolated from *Thermus aquaticus, Thermus thermophilus, Pyrococcus woesei, Pyrococcus furiosus, Thermococcus litoralis*, and *Thermotoga maritima*.

The polymerizing agent can have a fidelity (incorporation accuracy) of at least about 99% and a processivity (number of nucleotides incorporated before the enzyme moiety dissociates from the template) of at least about 20 nucleotides. Examples include T7 DNA polymerase, T7 DNA polymerase complexed with T7 helicase/primase, T5 DNA polymerase, HIV reverse transcriptase, *E. coli* DNA pol I, T4 DNA polymerase, T7 RNA polymerase, Taq DNA polymerase, *E. coli* RNA polymerase, and Phi29 DNA polymerase.

Nucleotides can be selected to be compatible with the polymerizing agent to be used. Procedures for selecting suitable nucleotide and polymerase combinations can be adapted from Ruth et al. (1981) Molecular Pharmacology 20:415-422; Kutateladze, T., et al. (1984) Nuc. Acids Res., 12: 1671-1686; Chidgeavadze, Z., et al. (1985) FEBS Letters, 183:275-278. In certain embodiments, the polymerizing agent is able to tolerate labeling moieties, quenching moieties, and/or chain elongation inhibiting moieties on the nucleotide, including the base, sugar and/or phosphate groups. For example, some applications of the present invention employ polymerizing agents that have increased ability to incorporate modified, fluorophore-labeled nucleotides into a growing complementary strand. Examples of such polymerizing agents have been described in U.S. Pat. No. 5,945,312, e.g., mutant bacteriophage T4 DNA polymerases, as well as mutant T2, T4, or T6 DNA polymerase including, but not limited to, L412M-DNA polymerase, Q380K-DNA polymerase, E395K-DNA polymerase, E743K-DNA polymerase, M725I-DNA polymerase, M725V-DNA polymerase, S756P-DNA polymerase, L771F DNA polymerase, L771H-DNA polymerase, -DNA polymerase, -DNA polymerase, V355A-DNA polymerase, E395K+L412M-DNA polymerase, L412M+E473K-DNA polymerase, E395K+L412M+ E743K-DNA polymerase, and Q380K+L412M+E743K-DNA polymerase.

In embodiments using target polynucleotide-primer complex anchored on a surface of a substrate, the polymerizing agent can be stored in a separate reservoir and flowed onto the substrates (e.g., into a flow chamber/synthesis channel/cell which houses the substrate) prior to each extension reaction cycle. The polymerizing agent also can be stored together with the other reaction reagents (e.g., the nucleotide triphosphates). Alternatively, the polymerizing agent can be immobilized onto the surface of the substrate (e.g., the surface of the synthesis channel) along with the target polynucleotide-primer complex, or while the target polynucleotide is added in solution.

B. Labeling Moieties

In certain embodiments, to facilitate detection of nucleotide incorporation, at least one and up to all types of the nucleotides (e.g., dATP, dTTP, dGTP, dCTP, and/or ATP, UTP, GTP, and CTP) bear a labeling moiety. Various labeling moieties which are easily detected include radioactive labels, optically-detectable labels, spectroscopic labels and the like. In certain embodiments, fluorescent labeling moieties are used. When more than one type of nucleotide bears a labeling moiety, a different kind of labeling moiety can be used to label each different type of nucleotide. However, in some applications, the different types of nucleotides can be labeled with the same kind of labeling moieties.

Various fluorescent labeling moieties can be used to label the nucleotides in the present invention. The fluorescent labeling moiety can be selected from any of a number of different moieties. In some embodiments a fluorescent group for which detection is quite sensitive is selected. For example, fluorescein- or rhodamine-labeled nucleotides may be selected and are available commercially.

Fluorescent moieties having a high quantum yield and a large extinction coefficient may be also be chosen to facilitate detection. Fluorescent moieties with a large Stokes shift (i.e., the difference between the wavelength of maximum absorbance and the wavelength of maximum emission) may also be selected so that the fluorescent emission is readily distinguished from the excitation source used. Further, certain visible and near IR fluorescent moieties are sufficiently fluorescent and photostable to be detected as single molecules. For example, single molecules of BODIPY R6G (525/545), LI-COR's, and IRD-38 (780/810) can be detected can be use in the practice of certain embodiments of the present invention. Fluorescent labels exhibiting particularly high coefficients of destruction can also be useful in destroying nonspecific background signals.

The affinity for the surface can vary for different fluorescent dyes. For example, Cy3 and Cy5 are used to label the primer or nucleotides in some embodiments of the invention. However, Cy5 has higher affinity to the surface under certain experimental conditions than Cy3, making Cy3 (the lower affinity dye) more suitable in certain embodiments.

Another factor that may be considered is the stability of different fluorescent dyes. For example, Cy5 is less stable and tends to bleach faster than Cy3. This can be an advantage or disadvantage, depending on the circumstances. In addition, different sizes of the dyes can also affect efficiency of incorporation of the nucleotides bearing them. In some embodiments, inefficient incorporation due to choking, for example, is desirable. In some emditions, inefficient incorporation may also be desirable to lengthen the half life of incorporation reactions, facilitating short cycle sequencing approaches. Further, the length of the linker between the labeling moiety and the nucleotide can impact efficiency of the incorporation (see, Zhu and Waggoner, Cytometry 28: 206, 1997).

An exemplary list of fluorophores, with their corresponding absorption/emission wavelength indicated in parenthesis, which can be used in the present invention include Cy3 (550/565), Cy5 (650/664), Cy7 (750/770), Rho123 (507/529), R6G (528/551), BODIPY 576/589 (576/589), BODIPY TR (588/616), Nile Blue (627/660), BODIPY 650/665 (650/665), Sulfo-IRD700 (680/705), NN382 (778/806), Alexa488 (490/520), Tetramethylrhodamine (550/570). and Rodamine X (575/605). In instances where a multi-labeling scheme is utilized, a wavelength which approximates the mean of the absorption maxima various labeling moieties may be used. Alternatively, multiple excitations may be performed, each using a wavelength corresponding to the absorption maximum of a specific labeling moiety.

Certain fluorescently-labeled nucleotides can be obtained commercially (e.g., from Perkin Elmer, Amersham, or BDL). Alternatively, fluorescently-labeled nucleotides can also be produced by various fluorescence-labeling techniques, e.g., as described in Kambara et al. (1988) "Optimization of Parameters in a DNA Sequenator Using Fluorescence Detection," Bio/Technol. 6:816-821; Smith et al. (1985) Nucl. Acids Res, 13:2399-2412; and Smith et al. (1986) Nature 321:674-679. Acyl fluoride of Cy5 cyanine dye can also be synthesized and labeled as described in U.S. Pat. No. 6,342,326. Other examples of nucleotides bearing fluorescent labeling moieties that may be used in certain embodiments include dATP-lissamine; dCTP-Cy3, dATP-Tetramethylrhodamine, and dATP-Texas Red.

There is a great deal of practical guidance available in the literature providing an exhaustive list of fluorescent molecules and their relevant optical properties. See, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing fluorophore molecules for covalent attachment via common reactive groups that can be added to a nucleotide, as exemplified by the following references: Haugland (supra); Ullman et al., U.S. Pat. No. 3,996,345; Khanna et al., U.S. Pat. No. 4,351,760.

Further, there are many linking moieties and methodologies for attaching fluorophore moieties to nucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™. II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

β- or γ-Quenching Moieties

Some embodiments of the present invention use labeling moieties that become detectable upon incorporation of nucleotide into the complementary strand. In certain embodiments, for example, the nucleotides used comprise a fluorescent moiety on any position, as well as a quenching moiety on any or all of the phosphates of a nucleotide that are removed as the nucleotide incorporates into a polynucleotide molecule. For example, the quenching moiety may be on the β-phosphate of a nucleotide diphosphate and/or on the or γ-phosphates of a nucleotide triphosphate. Alternatively or as well as, it may be on the δ-phosphate of a nucleotide tetraphosphate and/or on the ε-phosphate of a nucleotide pentaphosphate.

The quenching moiety hinders fluorescence of free nucleotides, due to the proximity of the quenching and fluorescent moieties on a given nucleotide molecule. However, incorporation of a nucleotide di-, tri-, tetra-, or pentaphosphate released the non-α phosphates, whereupon the quenching moiety is also released, separating the fluorescent-quenching pair. For example, incorporation of a nucleotide triphosphate into a growing strand releases the β- and -phosphates (as pyrophosphate). Consequently, upon incorporation and/or removal of the released phosphates, e.g., pyrophophate, fluorescence from the labeling moiety increases, allowing detection of incorporated nucleotide.

Any fluorescent-quenching pair can be used, where the fluorescent moiety attaches at any position on the nucleotide base, sugar, and/or α-phosphate, the quenching moiety is sufficiently proximal to the fluorescent moiety to inhibit its fluorescence, and the nucleotide bearing the fluorescent and quenching moieties remains capable of base-complementary incorporation by a polymerizing agent into a growing complementary strand. Nucleotide triphosphates having a quenching moiety attached to the γ-phosphate are of interest, as substitutions at this position are known to still allow recognition by polymerizing agents. See, e.g. Felicia et al., *Arch. Biochem Bophys.*, 246: 564-571 (1986).

In certain embodiments, the fluorescent and/or quenching moiety are derivatized for attachment to the nucleotide either directly or via a linker. There are many linking moieties and methods for coupling fluorescent and quenching moieties to nucleotides, for example: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227

(1993) and Fung et al., U.S. Pat. No. 4,757,141 (5' phosphoamino group via Aminolink™. II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Fluorescent-quenching pairs that can achieve intramolecular fluorescence quenching on a nucleotide include, for example, 9,10-dioxa-syn-3,4,6,7,-tetramethylbimane (bimane) and a halogen. Quenching efficiencies of halogen substituents on bimane fluorescence have been shown to increase in the order F<Cl<Br<I, in certain compounds. Sato et al. 1994. Other quenching moieties that may be used include 4-(4'-dimethylaminophenylazo)-benzoic acid (DABCYL ), dinitrophenyl (DNP), and trinitrophenyl (TNP).

As mentioned above, there is a great deal of practical guidance available in the literature providing an exhaustive list of fluorescent molecules and their relevant optical properties. Further, there is extensive guidance in the literature for derivatizing fluorescent and quenching moieties for covalent attachment via common reactive groups to a nucleotide, as exemplified by the following references: Haugland (supra); Ullman et al., U.S. Pat. No.3,996,345; Khanna et al., U.S. Pat. No. 4,351,760. Many suitable forms of these compounds are also available commercially.

Using fluorescently-labeled nucleotides bearing a non-a-phosphate quencher helps reduce background signals when detecting incorporated nucleotides. In such embodiments, detection of incorporation depends on "turning on" a fluorescent signal by de-quenching a moiety as the nucleotide becomes incorporated and non-α-phosphates released. Unincorporated nucleotides, however, remain quenched, thereby reducing background signal.

Efficient quenching can further help reduce background fluorescence. That is, incomplete quenching would result in low level background from each unincorporated molecule. In single molecule detection, high quenching efficiency is advantageous as it helps reduce background, enhancing the signal-to-noise ratio to permit detection of a single incorporated fluorescent moiety into a single complementary strand.

In some embodiments, the fluorescent moiety on an unincorporated nucleotide exists quenched with at least about a 2 fold, at least about a 3 fold, at least about a 4 fold, or at least about a 5 fold quenching efficiency compared to when the β- and/or γ-phosphates are detached from the nucleotide. In some embodiments the quenching efficiency is at least about 10 fold, at least about 20 fold, at least about 30 fold, at least about 40 fold, at least about 50 fold, at least about 100 fold, at least about 150 fold, at least about 200 fold, at least about 250 fold, at least about 300 fold, at least about 350 fold, at least about 400 fold at least about 450 fold, at least about 500 fold, at least about 550 fold, at least about 600 fold, at least about 650 fold, at least about 700 fold, at least about 750 fold, at least about 800 fold, at least about 900 fold, at least about 950 fold, and at least about 1000 fold. DABCYL, for example, quenches fluorescence from a wide variety of fluorescent moieties emitting between about 475 nm and about 805 nm, and has shown efficiencies ranging from about 90 to about 99.9% (see, S. Tyagi et al., Nat. Biotechnol. 16, 49 (1998); and G. T. Wang et al., Tetrahedron Lett. 31, 6493 (1990)).

Reactive and Enzymatic Labeling Moieties

Certain embodiments use labeling moieties that only become detectable upon further reaction, for example reaction with another moiety. Nucleotides bearing such a labeling moiety can therefore remain undetectable by a given detection means until allowed to undergo reaction, for example, after incorporation. This can help reduce background interference from unincorporated nucleotides when detecting incorporated nucleotides, as the free nucleotides may be removed from the polymerization complex before the reaction is allowed to proceed.

Embodiments utilizing reactive and/or enzymatic labeling moieties may be used with bulk methods of sequencing, for example bulk single base extensions. In some embodiments, refinements in the techniques may also allow for application to single molecule detection using reactive and/or enzymatic labeling moieties.

For example, some embodiments use nucleotides comprising a reactive moiety that can undergo a reaction, for example, following incorporation, to create a detectable product. In such embodiments, detection of the product can identify incorporation of the nucleotide. Reactive moieties include, for example, biotin as in biotin-dUTP, which can bind to streptavidin. Steptavidin in turn may be conjugated to an enzymatic moiety. The enzymatic moiety-conjugated streptavidin can be added to the biotin-labeled nucleotides after incorporated into a growing complementary strand, whereupon the enzymatic moiety may become bound to sites of incorporation. Addition of a substrate for the enzymatic moiety followed by detection of the product produced can identify incorporation.

Enzyme moieties can be selected that act on a substrate to produce a colored or otherwise easily detectable product. Examples include horseradish peroxidase (HRP) that catalyzes an oxidation reaction, changing a clear substrate to a colored product, as well as alkaline phosphatase, galactosidase, luciferase, or acetylcholinesterase.

Various binding pairs also may be used, where one member of the pair attaches at any position to a nucleotide base, sugar, and/or a-phosphate and the nucleotide remains capable of base-complementary incorporation by a polymerizing agent into a growing complementary strand. As well as biotin with streptavidin, biotin with avidin, digoxin with anti-digoxin, fluorescein with anti-fluorescein antibody, and the like may be used. For example, biotin-dUTP, digixoin-dUTP and fluorescein-dUTP, are known in the art. As an illustration, these could be detected using horse peroxidase-conjugated streptavidin, horseradish peroxidase-conjugated antidigoxin; and alkaline phosphatase-conjugated anti-fluorescent antibody, respectively.

In certain embodiments, nucleotides comprising an enzymatic moiety can be used, where the enzymatic moiety catalyzes a reaction, for example, following incorporation, to create a detectable product. Detection of the product can identify incorporation of the nucleotide. Again the enzyme moiety can be selected for its ability to act on a substrate to produce a colored or otherwise easily detectable product. Examples include horseradish peroxidase (HRP), alkaline phosphatase, galactosidase, luciferase, or acetylcholinesterase. These and other enzymatic labeling moieties known in the art may also be used, where the moiety can attach to any position of the nucleotide base, sugar, or a-phosphate, and the nucleotide remains capable of base-complementary incorporation by a polymerizing agent into a growing complementary strand.

Labeling a Fraction of the Nucleotides

In certain embodiments where there are multiple copies in each template molecule immobilized on the surface (e.g. on the surface of a synthesis channel), only a small percentage of labeled nucleotides is sufficient for detection. For example, a radioactive label can be determined by counting or any other method known in the art, while fluorescent labels can be induces to fluoresce, e.g., by excitation. For fluorescently-labeled nucleotides, the percentage of labeled nucleotides can be less than about 20%, less than about 10%, less than about 5%, less than about 1%, less than about 0.1%, less than about 0.01%, or less than about 0.001% of the total labeled and unlabeled nucleotides for each type of the nucleotides.

In certain embodiments, a certain degree of stalling or slowing down of incorporation is desired, e.g., in methods for "choking" the polymerizing agent and/or in methods utilizing short cycle sequencing. In bulk embodiments of such methods, the percentage of labeled nucleotides may be varied to obtain a desired degree of choking and/or of slowing down to prevent or hinder incorporation accordingly.

C. Blocking Moieties

In some embodiments, it may be desirable to employ blocking moieties in the primer extension reaction (see, e.g., Dower et al., U.S. Pat. No. 5,902,723), to form chain elongation inhibitors. Chain elongation inhibitors are nucleotide analogues which carry either chain terminating moieties or chain elongation inhibiting moieties, which prevent or hinder further addition by the polymerizing agent of nucleotides to the 3' end of the chain by becoming incorporated into the chain themselves, or are choking moieties that inhibit further chain elongation by steric hindrance. In some embodiments, the chain elongation inhibitors are dideoxynucleotides. Where the chain elongation inhibitors are incorporated into the growing polynucleotide chain, they can be removed after incorporation of the nucleotide has been detected, in order to allow the polymerization reaction to proceed using further nucleotides. Some 3' to 5' exonucleases, e.g., exonuclease III, are able to remove dideoxynucleotides.

Other than dideoxynucleotides, a blocking moiety can be employed on the 3' moiety of the deoxyribose group of a nucleotide to prevent or inhibit further incorporation. In certain embodiments, the blocking moiety can be removable under mild conditions (e.g., using photosensitive, weak acid labile, or weak base labile groups), thereby allowing for further elongation of the primer strand in the next synthetic cycle. If the blocking moiety also contains a labeling moiety, the dual blocking and labeling functions can be achieved without the need for separate reactions for the separate moieties. For example, a nucleotide can be labeled by attachment of a fluorescent dye group to the 3' moiety of the deoxyribose group, and the label removed by cleaving the fluorescent dye from the nucleotide, simultaneously generating a 3' hydroxyl group. The fluorescent dye may be linked to the deoxyribose by a linker arm which is easily cleaved by photochemical, chemical and/or enzymatic means.

Examples of blocking moieties include, among others, light sensitive groups such as 6-nitoveratryloxycarbonyl (NVOC), 2-nitobenzyloxycarbonyl (NBOC), .α,.α-dimethyl-dimethoxybenzyloxycarbonyl (DDZ), 5-bromo-7-nitroindolinyl, o-hydroxy-2-methyl cinnamoyl, 2-oxymethylene anthraquinone, and t-butyl oxycarbonyl (TBOC). Other blocking reagents are discussed, e.g., in U.S. Ser. No. 07/492,462; Patchornik (1970) J. Amer. Chem. Soc. 92:6333; and Amit et al. (1974) J. Org. Chem. 39:192.

Nucleotides possessing various labeling and blocking moieties can be readily synthesized. Moieties can be attached at appropriate sites on the nucleotide using chemistry and conditions as described, e.g., in Gait (1984) Oligonucleotide Synthesis: A Practical Approach, IRL Press, Oxford.

Choking Moieties

Alternatively, a labeling moiety may be used that is sufficiently large to "choke" the polymerizing upon its incorporation, preventing further chain elongation, without necessarily being on the 3' base position. Examples of labeling moieties that may be useful for this purpose are described in Example 9, as well as in Zhu et al., "Directly Labeled DNA Probes Using Fluorescent Nucleotides with Different Length Linkers," Nucleic Acids Res. 22: 3418-3422 (1994).

Other fluorophore labels that may be use to cause "choking" in the present invention include Cy3, Cy5, (including, for example dCTP-Cy3, dUTP-Cy3, and dUTP-Cy5 from Amersham Biosciences, dCTP-Cy5, dATP-Cy3, dGTP-Cy3, dATP-Cy5, and dGTP-Cy5 from Perkin-Elmer, and dCTP-Alexa647 from Molecular Probes), Cy7, Rho123, R6G, BODIPY 576/589, BODIPY TR, Nile Blue, BODIPY 650/665, Sulfo-IRD700, NN382, Alexa488, Tetramethylrhodamine and Rodamine X. The fluorescently-labeled nucleotides can be obtained commercially (e.g., from Perkin Elmer, Amersham, or BDL). Alternatively, fluorescently-labeled nucleotides can also be produced by various fluorescence-labeling techniques. There is extensive guidance in the literature for derivatizing fluorophore molecules for covalent attachment via common reactive groups that can be added to a nucleotide, e.g., Haugland (supra); Kambara et al. (1988) "Optimization of Parameters in a DNA Sequenator Using Fluorescence Detection," Bio/Technol. 6:816-821; Smith et al. (1985) Nucl. Acids Res, 13:2399-2412; and Smith et al. (1986) Nature 321:674-679. Acyl fluorides of Cy5 cyanine dye can also be synthesized and used as choking/labeling moieties.

There are also many linking moieties and methodologies for attaching fluorophore moieties to nucleotides, as exemplified by the following references: Eckstein, editor, Oligonucleotides and Analogues: A Practical Approach (IRL Press, Oxford, 1991); Giusti et al., PCR Methods and Applications, 2: 223-227 (1993) Agrawal et al., Tetrahedron Letters, 31: 1543-1546 (1990) (attachment via phosphoramidate linkages); Sproat et al., Nucleic Acids Research, 15: 4837 (1987) (5' mercapto group); and the like.

Choking moieties may attach to any position on the nucleotide base, sugar, or phosphate, where the nucleotide remains capable of base-complementary incorporation by a polymerizing agent into a growing polynucleotide strand. In certain embodiments, the label is attached to the base, where it better distorts the double helix of the synthesized molecule, thereby inhibiting further polymerizing activity. For example, Krider et al., "2' modified nucleosides for site-specific labeling of oligonucleotides" Bioconjug. Chem. January-February 13(1):155-62 (2002), describes the synthesis of 2' modified nucleosides designed specifically for incorporating labels into oligonucleotides These methods can be used to attach sufficiently large labeling moieties to the 2' site to cause choking. Similar methods can be used to attach labeling moieties to the 1' base position, the 2' base position, the 4' base position, the 5' base position, the sugar moiety, the alpha phosphate, the beta phosphate, or the gamma phosphate.

Crystal structures of several DNA polymerases have been described. See e.g. Doublie et al., "Crystal Structure of a Bacteriophage T7 DNA Replication Complex at 2.2 Angstrom Resolution," Nature 391:251-258 (1998); Ollis, D. L., Brick, P., Hamlin, R. Xuong, N. G. & Steitz, T. A., "Structure of large fragments of *Eschericia coli* DNA polymerase I complexed with dTMP", Nature 313, 762-766 (1985) (crystal structure of the Klenow fragment of *E. coli* Pol I); Beese, L. S., Derbyshire, V. & Steitz, T. A., "Structure of DNA Polymerase I Klenow fragment bound to duplex DNA," Science 260, 352-355 (1993) (crystal structure of the Klenow fragment of *E. coli* Pol I); Korolev, S., Nayal, M., Barnes, W. M., Di Cera, E. & Waksman, G. "Crystal structure of the large fragment of *Thermus aquaticus* DNA polymerase I at 2.5-Å resolution: structural basis for thermostability," Proc. Natl. Acad. Sci. USA 92, 9264-9268 (1995) (crystal structure of the analogous fragments of *Thermus aquaticus* DNA polymerase); Kiefer, J. R. et al., "Crystal structure of a thermostable *Bacillus* DNA polymerase I large fragment at 2.1 Å resolution," Structure 5, 95-108 (1997); and Kim, Y. et al., "Crystal structure of *Thermus aquaticus* DNA polymerase," Nature 376, 612-616 (1995). The dimensions of these structures can indicate what size labeling moieties cause a given polymerizing agent to choke. Preferably, the labels are as bulky as Cy5, with molecular weights at least about 1.5 kDa. More preferably, the labels are bulkier than Cy5, having molecular weights of at least about 1.6 kDa, at least about 1.7 kDa, at least about 1.8 kDa, at least about 1.9 kDa, at least about 2.0 kDa, at least about 2.5 kDa, or even at least about 3.0 Kda.

Further examples of such larger dyes include the following, with corresponding formula weights (in g/mol) in parentheses: Cy5 (534.6); Pyrene (535.6); 6-Carboxyfluorescein (FAM) (537.5); 6-Carboxyfluorescein-DMT (FAM-X) (537.5); 5(6)-Carboxyfluorescein (FAM) (537.5); 5-Fluorescein (FITC) (537.6); Cy3B (543.0); WellRED D4-PA (544.8); BODIPY 630/650 (545.5); 3' 6-Carboxyfluorescein (FAM) (569.5); Cy3.5 (576.7); Cascade Blue (580.0); Alexa Fluor 430 (586.8); Lucifer Yellow (605.5); Alexa Fluor 532 (608.8); WellRED D2-PA (611.0); Cy5.5 (634.8); DY-630 (634.8); DY-555 (636.2); WellRED D3-PA (645.0); Rhodamine Red-X (654.0); DY-730 (660.9); DY-782 (660.9); DY-550 (667.8); DY-610 (667.8); DY-700 (668.9); 6-Tetrachlorofluorescein (TET) (675.2) Alexa Fluor 568 (676.8); DY-650 (686.9); 5(6)-Carboxyeosin (689.0); Texas Red-X (702.0); Alexa Fluor 594 (704.9); DY-675 (706.9); DY-750 (713.0); DY-681 (736.9); Hexachlorofluorescein (HEX) (744.1); DY-633 (751.9); LightCycler Red 705 (753.0); LightCycler Red 640 (758.0); DY-636 (760.9); DY-701 (770.9); FAR-Fuchsia (5'-Amidite) (776.0); FAR-Fuchsia (SE) (776.0); DY-676 (808.0); Erythrosin (814); FAR-Blue (5'-Amidite) (824.0); FAR-Blue (SE) (824.0); Oyster 556 (850.0); Oyster 656 (900.0); FAR-Green Two (SE) (960.0); Alexa Fluor 546 (964.4); FAR-Green One (SE), (976.0); Alexa Fluor 660 (985.0); Oyster 645 (1000.0); Alexa Fluor 680 (1035.0); Alexa Fluor 633 (1085.0); Alexa Fluor 555 (1135.0); Alexa Fluor 647 (1185.0); Alexa Fluor 750 (1185.0); Alexa Fluor 700 (1285.0). These reagents are commercially available from SYNTHEGEN, LLC (10590 Westoffice Drive, Suite 200, Houston, Tex. 77042), for example, or can be synthesized by appropriate methods.

Sander-like Sequencing Using Choking Moieties

While many of the innovations of the present invention relate to single molecule sequencing, certain advances herein described also facilitate alternate or improved methods of carrying out classical bulk sequencing.

For example, another aspect of the present invention relates to an alternate method of doing classic Sanger sequencing (a method of bulk sequencing). This aspect involves a method for sequencing a target polynucleotide without using ddNTP's, by providing four reaction mixtures, each comprising a primed target polynucleotide; a polymerizing agent; and four nucleotides, wherein a proportion of one of the four nucleotides in each mixture comprises a moiety that inhibits further chain elongation by steric hindrance; allowing incorporation of the nucleotides into a complementary strand until a nucleotide preventing further chain elongation becomes incorporated; allowing repetition of the above step to obtain a plurality of complementary strands of varying lengths; and size-sorting the plurality of strands to analyze the sequence of the target polynucleotide.

The proportion of nucleotide types bearing a chain elongation inhibiting moiety can be selected to allow limited chain termination. Thus in a plurality of growing complementary strands, a nucleotide comprising an inhibiting moiety will become incorporated at different positions along the sequence where that particular nucleotide type appears. This results in a plurality complementary strands of varying lengths, terminating at the positions where an inhibiting moiety became incorporated. Preferably, this produces a ladder of strands, each one nucleotide longer than the other. Sanger et al. PNAS 74: 5463 (1977).

In some embodiments, a nucleotide bears a labeling moiety, which becomes incorporated into the growing complementary strands. In other embodiments, a primer bearing a labeling moiety is used to prime the target polynucleotide. The labeling moiety may involve any of the detection approaches described herein, or any other suitable labeling technique known in the art. The labeling moiety facilitates detection of the complementary strands, for example during size-sorting.

The complementary strands of varying lengths can be size-sorted by any known methods known in the art to resolve different length strands, including various electrophoresis techniques, including polyacrylamide gel electrophoresis (PAGE), ultra-thin slab gel electrophoresis, capillary array electrophoresis, and automatic gel readers. To facilitate determination of the nucleotide type terminating each strand, a detectably distinguishable labeling moiety may be used in each of the four reaction mixtures, or the strands from the different reaction mixtures may be sorted in different gels or gel lanes, or in different capillaries. In certain embodiments, the strands of varying lengths are resolved using mass spectroscopy. For a review of some of these methods, see Chen "High-Speed DNA-Sequence Analysis," Prog. Biochem. Biophys. 22: 223-227 (1995).

D. Removal of Labeling and Blocking Moieties

By carrying out the incorporation and detection steps, one or more nucleotides on the target polynucleotide adjacent to the 3' end of the primer can be identified. Once this has been achieved, labeling moiety may be removed before repeating the cycle to discover the identity of the next nucleotide or nucleotides. Removal of the labeling moiety can be effected by removal of the labeled nucleotide itself, using a 3'-5' exonuclease, for example, and subsequent replacement with an unlabeled nucleotide.

Alternatively, the labeling moiety can be removed from the nucleotide. Release of a fluorescent dye, for example, can be achieved if a detachable connection between the nucleotide and the fluorescent molecule is used. For example, the use of disulfide bonds enables one to disconnect the dye by applying a reducing agent like dithiothreitol (DTT). The connection may also be detached by other chemical means, as well as by enzymatic and/or photochemical means.

In a further alternative, where the labeling moiety is a fluorescent moiety, it is possible to neutralize the fluorescence by bleaching it with radiation. Photobleaching can be performed according to methods, e.g., as described in Jacobson et al., "International Workshop on the Application of Fluorescence Photobleaching Techniques to Problems in Cell Biology," Federation Proceedings, 42:72-79, 1973; Okabe et al., J Cell Biol 120:1177-86, 1993; Wedekind et al., J Microsc. 176 (Pt 1): 23-33, 1994; and Close et al., Radiat Res 53:349-57, 1973.

If choking and/or other blocking moieties have been used, these can be removed before the next cycle take place. 3' blocking moieties can be removed by photochemical, chemical or enzymatic cleavage of the blocking group from the nucleotide. For example, chain terminating moieties are removed with a 3'-5' exonuclease, e.g., exonuclease III. Once the labeling and blocking moieties have been removed, the cycle can be repeated to discover the identity of the next nucleotide or nucleotides.

Similarly, if a labeling moiety sufficiently large to cause choking is used, the moiety, or steric hindering portion of the moiety, can be removed to allow chain elongation to resume. If the labeling moiety only causes choking after a small number of labeled nucleotides are incorporated, the moiety or a portion thereof may be removed only after every few incorporations. Choking labeling moieties, or portions thereof, may be removed similarly as described above, i.e. by enzymatic, chemical, or photochemical means.

Removal of the blocking moieties may be unnecessary if only a percentage of the nucleotides carry blocking moieties, e.g., in certain bulk applications. In this approach, the chains incorporating the blocked nucleotides are permanently terminated and no longer participate in the elongation processes. In such embodiments, a small percentage of permanent loss in each cycle can be tolerated.

In some embodiments, nucleotide incorporation is monitored by detection of pyrophosphate release (see, e.g., W098/13523, W098/28440, and Ronaghi et al., Science 281:363, 1998). Pyrophosphate is released upon incorporation of a deoxynucleotide or dideoxynucleotide, which can be detected enzymatically. For example, a pyrophosphate-detection enzyme cascade can be included in the reaction mixture in order to produce a chernoluminescent signal. In some embodiments, this method employs no wash steps, instead relying on continual addition of reagents. Also, instead of or as well as deoxynucleotides or dideoxynucleotides, one or more nucleotide analogues can be used which are capable of acting as substrates for the polymerizing agent but incapable of acting as substrates for the pyrophosphate-detection enzyme.

Removal of Non-cleavable Labeling Moieties

Certain embodiments of the invention provide a plurality (two or more) of nucleotide types, where a nucleotide bears both a non-cleavable labeling moiety and a blocking moiety. While most other groups have focused on cleavable labels, this approach uses bleaching instead. That is, signal from incorporated labeling moiety may be neutralized or reduced after one or more incorporations into the complementary strand by bleaching, such as photo-bleaching or chemical bleaching, rather than by cleavage. As mentioned above, photobleaching can be performed according to methods, e.g., as described in Jacobson et al., "International Workshop on the Application of Fluorescence Photobleaching Techniques to Problems in Cell Biology," Federation Proceedings, 42:72-79, 1973; Okabe et al., J Cell Biol 120:1177-86, 1993; Wedekind et al., J Microsc. 176 (Pt 1): 23-33, 1994; and Close et al., Radiat Res 53:349-57, 1973.

"Non-cleavable" is used herein to indicate a chemical linkage that is particularly resistant to cleavage under the conditions used in the polymerization reactions and detection procedures, as well as any other reactions short of very harsh or unique conditions. That is, the connection between the labeling moiety and the nucleotide remains intact under the physical, chemical, and/or enzymatic conditions of the incorporation and detection steps, as well as any bleaching step used to reduce its signal.

The labeling moiety may attach directly or indirectly to one or more positions on the nucleotide base, sugar, or α-phosphate, so long as it is stable and allows substrate recognition by the polymerizing agent. Three-D structures of the polymerization site reveal sufficient space surrounding the area of the 5'-position of a pyrimidine to allow for modification. For example, energy transfer dyes at the 5-position of the pyrimidines (T and C) allow recognition and incorporation, as well as dyes at the 7-position of purines (G and A) (Rosenblum et al. 1997, Zhu et al. 1994).

Non-cleavable linkages may include covalent or other types of bonds that require particular conditions for cleavage. Methoxy linkages, for example, require stringent anhydrous conditions, making it difficult to chemically cleave these linkages. Similarly, —O-ethoxy-nucleotides have been reported as good substrates for several polymerizing agents (Axelrod et al. 1978), thus providing another non-cleavable linkage for use in certain embodiments of the invention.

Other examples of non-cleavable labeling moieties include fluorescein phophoramidites (FAM), digoxigenin-nucleotides, and mercurated nucleotide analogs. FAM dyes may be coupled to nucleotides, e.g., at a hydroxyl group. Theisen et al. 1992. Such dyes have been used in automated DNA synthesizers, where the dye and its linkage to an oligonucleotide have proven stable under polymerization and cleavage/deprotection conditions. Similarly, digoxigenin-11-dUTP can be incorporated in a growing polynucleotide strand and remains intact even under conditions of the polymerase chain reaction. Taveira et al. 1992. Further, mercury atom-bearing pyrimidine nucleotides, have been shown to be heat- and thiol-stable and can be specifically incorporated into a growing complementary strand by polymerizing agents. Bridgman et al. 1996.

Single Step Bleaching & Cleaving

Certain embodiments of the present invention can reduce the number of steps needed for analyzing sequences by synthesis. For example, certain embodiments achieve reduction of incorporated signals along with reversal of chain termination in a single step, even where the labeling moiety and the blocking moiety are separate moieties. Such embodiments utilize nucleotides where a nucleotide bears a labeling moiety and a blocking moiety on different positions on the nucleotide. By using a blocking moiety having a chemically-cleavable group, however, it is possible to chemically cleave the blocking moiety, thus reversing chain termination, while chemically bleaching incorporated signal in a single step. Similarly, by using a blocking moiety having a photo-cleavable group, it is possible to photo-cleave the blocking moiety, thus reversing chain termination, while photo-bleaching incorporated signal in a single step.

The bleaching plus cleaving step may be performed after incorporation of about one, about two, about three, about four, about five, about six, about seven, about eight, about nine, or about ten incorporations. Using such an approach, bleaching and resumption of chain elongation may occur in a single step, even where the labeling moiety is a separate moiety from the blocking moiety and even where the labeling moiety attaches to the nucleotide via a non-cleavable linkage.

In certain embodiments using chemical cleaving and bleaching, the blocking moiety is coupled to any position of the nucleotide by any linkage susceptible to cleavage by chemical means that also serves to chemically bleach incorporated labeling moiety. Attachment of the blocking moiety can be made to the base, sugar, or α-phosphate positions of the nucleotide, for example, with or without a linker, where the nucleotide remains capable of base-complementary incorporation by a polymerizing agent into a growing complementary strand.

As noted above, disulfide linkage between a moiety and a nucleotide, for example, permits chemical cleavage using dithiothreitol (DTT). Thiol-modified nucleotides have also proved useful for cleavably-attaching a variety of moieties to nucleotides. Hanna et al., "Synthesis and Characterization of a New Phito-Cross-Linking CTP Analog and Its Use in Photoaffinity-Labeling *Escherichia-coli* and T7-RNA Polymerases," Nucleic Acids Res. 21: 2073-2079 (1993). Any other suitable means of chemical cleavage may be used that does not damage the polymerization complex nor the linkages of the polynucleotides.

In certain embodiments using photo cleaving and bleaching, the blocking moiety is coupled to any position of the nucleotide by any linkage susceptible to photo-cleavage, where the photo-radiation used also serves to photo-bleach the incorporated labeling moiety and the nucleotide remains capable of base-complementary incorporation by a polymerizing agent into a growing complementary strand. Typically, a wavelength equal to the wavelength of light absorbed by the fluorescent moiety can be used to photobleach it.

Attachment of the blocking moiety can be made to the base, sugar, or a-phosphate positions of the nucleotide, with or without a linker. Photocleavable linkers, such as linkers comprising a 2-nitrbenzyl moiety have been demonstrated. Hasan, et al 1997; Li et al. 2003. Such linkers are stable under polymerization conditions, but are cleaved when subjected to UV irradiation at about 340 nn. Similarly, 9-phenylthioxanthyl, 9-(2-naphthyl)-thioxanthenol, and 9-(2-(6-methoxy) naphthyl)-thioxanthenol have been developed as photocleavable protecting groups for hydroxyl functionality of nucleosides.

Radiation used to photocleave the blocking moiety can also bleach signals from fluorescent moieties, for example, using light, ultraviolet light and/or laser radiation of a wavelength absorbed by a fluorescent moiety. In some embodiments, UV irradiation of 340 nm, which cleaves 2-nitrobenzyl linkers, may also bleach fluorescent labels with similar absorption maxima (e.g. 4-(4-methoxybenzyl amino)-7-nitrobenzofurazan, 5-dimethylamino naphthalene-1-sulfonyl chloride, dansyl cadaverine, and N-(lodoacetaminoethyl)-1-naphthylamine-5-sulfonic acid. See http:www.sigmaaldrich.com/suite7/Brands/Fluka_Riedel_Home/Analytical/Fluoresent_Probes/Labels.html.

Furthermore, for FRET embodiments, bleaching radiation may be selected to extinguish signal from the acceptor fluorophore but not the donor fluorophore, facilitating repeated used of the same donor moiety with different acceptor labeling moieties as they become incorporated into a growing complementary strand during sequencing analysis. For example, where Cy3 is used as the donor moiety and Cy5 is used as the acceptor moiety, a red laser of about 635 nm can be used to bleach the Cy5 acceptor, leaving the Cy3 donor unharmed. Quake et al., *Sequencing information can be obtained from single DNA molecules*, PNAS 100(7):3960-3964 (2003).

The photobleaching radiation can be applied as a light pulse for a certain period of time to destroy or reduce incorporated signal. The light pulse is typically applied for about 50 seconds or less, about 30 seconds or less, about 20 seconds or less, about 15 seconds or less, about 10 seconds or less, about 5 seconds or less, about 3 seconds or less, about 1 second or less, about 0.5 seconds or less, about 0.2 seconds or less, and about 0.1 second or less.

E. Reaction Conditions

The reaction mixture for the polymerizing reactions may comprise an aqueous buffer medium, which may be optimized for the particular polymerizing agent. In general, the buffer can include a source of monovalent ions, a source of divalent cations and a buffering agent. Any convenient source of monovalent ions, such as KCl, K-acetate, NH4-acetate, K-glutamate, NH4Cl, ammonium sulfate, and the like may be employed, where the amount of monovalent ion source present in the buffer will typically be present in an amount sufficient to provide a conductivity in a range from about 500 to about 20,000, usually from about 1000 to about 10,000, and more usually from about 3,000 to about 6,000 micromhs.

The divalent cation may be magnesium, manganese, zinc and the like. Any convenient source of magnesium cation may be employed, including $MgCl_2$, Mg-acetate, and the like. The amount of Mg ion present in the buffer may range from about 0.5 to about 20 mM, from about 1 to about 12 mM, from about 2 to about 10 mM, or about 5 mM.

Representative buffering agents or salts that may be present in the buffer include Tris, Tricine, HEPES, MOPS and the like, where the amount of buffering agent will typically range from about 5 to about 150 mM, from about 10 to about 100 mM, or from about 20 to about 50 mM. In certain embodiments, the buffering agent will be present in an amount sufficient to provide a pH ranging from about 6.0 to about 9.5, including a pH about 7.6 at about 25° C. Other agents which may be present in the buffer medium include chelating agents, such as EDTA, EGTA and the like.

G. Sample Housing

The substrate can be housed in a flow chamber having an inlet and outlet to allow for renewal of reactants which flow past the immobilized moieties. The flow chamber can be made of plastic, glass, membrane material or gel, and can either be open or transparent in the plane viewed by the microscope or optical reader. Electro-osmotic flow can be achieved by a fixed charge on the substrate and a voltage gradient (current) passing between two electrodes placed at opposing ends of the support. Pressure driven flow can be facilitated by microfluidic device with an external pressure source or by microfluidic peristaltic pump (see, e.g., Unger et al., Science 288: 113-116, 2000).

The flow chamber can be divided into multiple channels for separate polymerization reactions. Examples of micro flow chambers are described in Fu et al. Nat. Biotechnol. (1999) 17:1109, which describes a micro-fabricated fluorescence-activated cell sorter with 3 μm×4 μm channels that utilizes electro-osmotic flow for sorting. In certain embodiments, the flow chamber can contain micro-fabricated synthesis channels as described in WO01/32930. The polynucleotide templates or primers can be immobilized to the surface of the synthesis channels. These synthesis channels can be in fluid communication with a microfluidic device, which controls flow of reaction reagents. As an example, microfluidic devices that can be employed to control flow of reaction reagents in the present invention have been described in WO01/32930.

The present invention also provides apparatuses for carrying out the methods of the invention. Other than the substrate to which the target polynucleotides or primers are attached, the apparatuses usually comprise a flow chamber in which the substrate is housed. In addition, the apparatuses can optionally contain plumbing devices (e.g., an inlet and an outlet port), a light source, and a detection system described herein. For example, a microfabricated apparatus as described in WO01/32930 can be adapted to house the substrate of the present invention, as described below:

1. Preferred Embodiments of the Apparatuses a. Basic Features of the Apparatuses Certain embodiments of the flow chambers of the present invention can comprise micro-fabricated channels to which polynucleotide templates or primers are attached. Optionally, the apparatuses comprise plumbing components (e.g., pumps, valves, and connecting channels) for flowing reaction reagents. The apparatuses can also comprise an array of reservoirs for storing reaction reagents (e.g., the polymerizing agent, each type of nucleotide, and other reagents can each be stored in a different reservoir).

The micro-fabricated components of the apparatuses can all have a basic "flow channel" structure. The term "flow channel" or "micro-fabricated flow channel" refers to a recess in a structure, which can contain a flow of fluid or gas. The polynucleotides can be attached to the interior surface of micro-fabricated channels in which synthesis occurs. For consistency and clarity, the flow channels are termed "synthesis channels" when referring to such specific use. The micro-fabricated flow channels can also be actuated to function as plumbing components (e.g., micro-pumps, micro-valves, or connecting channels) of the apparatuses.

In some applications, micro-fabricated flow channels are cast on a chip (e.g., a elastomeric chip). Synthesis channels are formed by bonding the chip to a flat substrate (e.g., a glass cover slip), which seals the channel. Thus, one side of the synthesis channel is provided by the flat substrate. Typically, the polynucleotide templates or primers are attached to the interior surface of the substrate within the synthesis channel.

The plumbing components can be micro-fabricated as described in the present invention. For example, the apparatuses can contain, in an integrated system, a flow cell in which a plurality of synthesis channels and fluidic components (such as micro-pumps, micro-valves, and connecting channels) for controlling the flow of the reagents into and out of the flow cell are present. Alternatively, the sequencing apparatuses of the present invention utilize plumbing devices described in, e.g., Zdeblick et al., A Microminiature Electric-to-Fluidic Valve, Proceedings of the 4th International Conference on Solid State Transducers and Actuators, 1987; Shoji et al., "Smallest Dead Volume Microvalves for Integrated Chemical Analyzing Systems," Proceedings of Transducers '91, San Francisco, 1991; Vieider et al., "A Pneumatically Actuated Micro Valve with a Silicon Rubber Membrane for Integration with Fluid Handling Systems," Proceedings of Transducers '95, Stockhohn, 1995.

As noted above, at least some of the components of the apparatuses are micro-fabricated. Micro-fabrication refers to feature dimensions on the micron level, with at least one dimension of the micro-fabricated structure being less than about 1000 μm. In some apparatuses, only the synthesis channels are micro-fabricated. In some apparatuses, in addition to the synthesis channels, the valves, pumps, and connecting channels are also micro-fabricated. Unless otherwise specified, the discussion below of micro-fabrication is applicable to production of all micro-fabricated components of the apparatuses (e.g., the synthesis channels in which polymerization reactions occur, and the valves, pumps, and connecting channels for controlling reagent flow to the synthesis channels). Employment of micro-fabricated synthesis channels and/or micro-fabricated plumbing components significantly reduce the dead volume and decrease the amount of time needed to exchange reagents, which in turn increase throughput.

In general, the micro-fabricated structures (e.g., synthesis channels, pumps, valves, and connecting channels) have widths of about 0.01 to about 1000 microns, and a width-to depth ratio of between about 0.1:1 to about 100:1. Preferably, the width is in the range of about 10 to about 200 microns, with a width-to-depth ratio of about 3:1 to about 15:1.

b. Non-elastomer Based Apparatuses

As discussed above, while elastomers are preferred materials for fabricating the apparatuses of the present invention, non-elastomer based microfluidic devices can also be used in the apparatuses of the present invention. In some applications, the apparatuses utilize microfluidics based on conventional micro-electromechanical system (MEMS) technology. Methods of producing conventional MEMS microfluidic systems such as bulk micro-machining and surface micro-machining have been described, e.g., in Terry et al., A Gas Chromatographic Air Analyzer Fabricated on a Silicon Wafer, IEEE Trans. on Electron Devices, v. ED-26, pp. 1880-1886, 1979; and Berg et al., Micro Total Analysis Systems, New York, Kluwer, 1994.

Bulk micro-machining is a subtractive fabrication method whereby single crystal silicon is lithographically patterned and then etched to form three-dimensional structures. For example, bulk micromachining technology, which includes the use of glass wafer processing, or silicon-to-glass wafer bonding, has been commonly used to fabricate individual microfluidic components. This glass-bonding technology has also been used to fabricate microfluidic systems.

Surface micro-machining is an additive method where layers of semiconductor-type materials such as polysilicon, silicon nitride, silicon dioxide, and various metals are sequentially added and patterned to make three-dimensional structures. Surface micromachining technology can be used to fabricate individual fluidic components as well as microfluidic systems with on-chip electronics. In addition, unlike bonded-type devices, hermetic channels can be built in a relatively simple manner using channel walls made of polysificon (see, e.g., Webster et al., Monolithic Capillary Gel Electrophoresis Stage with On-Chip Detector, in International Conference on Micro Electromechanical Systems, MEMS 96, pp. 491-496, 1996), silicon nitride (see, e.g., Mastrangelo et al., Vacuum-Sealed Silicon Micromachined Incandescent Light Source, in Intl. Electron Devices Meeting, IDEM 89, pp. 503.506, 1989), silicon dioxide and the like.

In some applications, electrokinetic flow based microfluidics can be employed in the apparatuses of the present invention. Briefly, these systems direct reagents flow within an interconnected channel and/or chamber containing structure through the application of electrical fields to the reagents. The electrokinetic systems concomitantly regulate voltage gradients applied across at least two intersecting channels. Such systems are described, e.g., in WO 96/04547 and U.S. Pat. No. 6,107,044.

An exemplary electrokinetic flow based microfluidic device can have a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection.

In some electrokinetic flow based apparatuses, at least three intersecting channels having at least four unintersected termini are present. In a basic cross channel structure, where a single horizontal channel is intersected and crossed by a single vertical channel, controlled electrokinetic transport operates to direct reagent flow through the intersection, by providing constraining flows from the other channels at the intersection. Simple electrokinetic flow of this reagent across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage).

In some other applications, the apparatus comprises a micro-fabricated flow cell with external mini-fluidics. The glass cover slip can be anodically bonded to the surface of the flow cell. The interrogation region is 100 μm×100 μm×100 μm, while the input and output channels are 100 μm×100 μm×100 μm. Holes for the attachment of plumbing are etched at the ends of the channels. For such apparatuses, the fluidics can be external. Plumbing can be performed with standard HPLC components, e.g., from Upchurch and Hamilton. In the interrogation region, the polynucleotide template or primer can be attached to the surface with standard avidin-biotin chemistry, for example.

Multiple copies of templates can be attached to the apparatus. For example, for a 7 kb template, the radius of gyration is approximately 0.2 μm. Therefore, about 105 molecules can be attached while preventing the molecules from touching. Reagent switching can be accomplished with, e.g., an Upchurch six-port injection valve and driven by, e.g., a Thar Designs motor. Fluid can be pumped with a syringe pump. The detection system can be an external optical microscope, with the objective being in close proximity to the glass cover slip.

V. Detection of Incorporated Signals

A. Detection System in General

Certain embodiments of the present invention provide for detection of a single nucleotide into a single target polynucleotide. A number of methods are available for this purpose (see, e.g., Nie et al., Science 266: 1013, 1994; Funatsu et al., Nature 374: 555, 1995; Mertz et al., Optics Letters 20: 2532, 1995; and Unger et al., Biotechniques 27: 1008, 1999). Methods for visualizing single molecules of polynucleotides labeled with an intercalating dye include, e.g., fluorescence microscopy as described in Houseal et al., Biophysical Journal 56: 507, 1989. Even the fluorescent spectrum and lifetime of a single molecule excited-state can be measured (Macklin et al., Science 272: 255, 1996). Standard detectors such as a photomultiplier tube or avalanche photodiode can be used. Full field imaging with a two-stage image intensified CCD camera can also used (Funatsu et al., supra). Additionally, low noise cooled CCD can also be used to detect single fluorescent molecules (see, e.g., Unger et al., Biotechniques 27: 1008-1013, 1999; and SenSys spec: http://www.photomet-.com/pdfs/datasheets/sensys/ss1401e.pdf).

The detection system for the signal may depend upon the labeling moiety used, which can be defined by the chemistry available. For optical signals, a combination of an optical fiber or charged couple device (CCD) can be used in the detection step. In those circumstances where the substrate is itself transparent to the radiation used, it is possible to have an incident light beam pass through the substrate with the detector located opposite the substrate from the polynucleotides. For electromagnetic labeling moieties, various forms of spectroscopy systems can be used. Various physical orientations for the detection system are available and discussion of important design parameters is provided in the art (e.g., Arndt-Jovin et al., J Cell Biol 101: 1422-33, 1985; and Marriott et al., Biophys J 60: 1374-87, 1991).

A number of approaches can be used to detect incorporation of fluorescently-labeled nucleotides into a single polynucleotide molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. General reviews are available describing these technologies, including, e.g., Basche et. al., eds., 1996, Single molecule optical detection, imaging, and spectroscopy, Weinheim: VCM; and Plakhotnik, et. al., Single-molecule spectroscopy, Ann. Rev. Phys, Chem. 48: 181-212. In general, the methods involve detection of laser-activated fluorescence using a microscope equipped with a camera. It is sometimes referred to as a high-efficiency photon detection system (see, e.g., Nie, et. al., 1994, Probing individual molecules with confocal fluorescence microscopy, Science 266: 1018-1019). Other suitable detection systems are discussed in the Examples below.

Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

B. Total Internal Reflection Fluorescence (TIRF) Microscopy

Some embodiments of the present invention use total internal reflection fluorescence (TIRF) microscopy for two-dimensional imaging. TIRF microscopy uses totally internally reflected excitation light and is well known in the art. See, e.g., Watkins et al., J Biomed Mater Res 11:915-38, 1977; and Axelrod et al., J Microsc, 129:19-28, 1983. In certain embodiments, detection is carried out using evanescent wave illumination and total internal reflection fluorescence microscopy. An evanescent light field can be set up at the surface, for example, to image fluorescently-labeled polynucleotide molecules. When a laser beam is totally reflected at the interface between a liquid and a solid substrate (e.g., a glass), the excitation light beam penetrates only a short distance into the liquid. In other words, the optical field does not end abruptly at the reflective interface, but its intensity falls off exponentially with distance. This surface electromagnetic field, called the 'evanescent wave', can selectively excite fluorescent molecules in the liquid near the interface. The thin evanescent optical field at the interface provides low background and facilitates the detection of single molecules with high signal-to-noise ratio at visible wavelengths (see, M. Tokunaga et al., Biochem. and Biophys. Res. Comm. 235, 47 (1997) and P. Ambrose, Cytometry, 36, 244 (1999)).

The evanescent field can also image fluorescently-labeled nucleotides upon their incorporation into the immobilized target polynucleotide-primer complex in the presence of a polymerizing agent. Total internal reflection (TIR) fluorescence microscopy can then be used to visualize the immobilized target polynucleotide-primer complex and/or the incorporated nucleotides with single molecule resolution. With TIR technology, the excitation light (e.g., a laser beam) illuminates only a small volume of solution close to the substrate, called the excitation zone. Signals from free (unincorporated) nucleotides in solution outside the excitation zone would not be detected. Signals from free nucleotides that diffuse into the excitation zone would appear as a broad band background because the free nucleotides move quickly across the excitation zone.

TIRF microscopy has been used to examine various molecular or cellular activities, e.g., cell/substrate contact regions of primary cultured rat myotubes with acetylcholine receptors labeled by fluorescent alpha-bungarotoxin, and human skin fibroblasts labeled with a membrane-incorporated fluorescent lipid (see, e.g., Thompson et al., Biophys J. 33: 435-54, 1981; Axelrod, J. Cell. Biol. 89: 141-5, 1981; and Burghardt et al., Biochemistry 22: 979-85, 1983). TIRF examination of cell/surface contacts dramatically reduces background from surface autofluorescence and debris. TIRF has also been combined with fluorescence photobleaching recovery and correlation spectroscopy to measure the chemical kinetic binding rates and surface diffusion constant of fluorescent labeled serum protein binding to a surface at equilibrium (see, e.g., Burghardt et al., Biophys J. 33: 455-67, 1981); and Thompson et al., Biophys J, 43: 103-14, 1983). Additional examples of TIRF detection of single molecules have been described in Vale et. al., 1996, Direct observation of single kinesin molecules moving along microtubules, Nature 380: 451; and Xu et al., 1997, Direct Measurement of Single-Molecule Diffusion and Photodecomposition in Free Solution, Science 275: 1106-1109.

The penetration of the field beyond the substrate depends on the wavelength and the laser beam angle of incidence. Deeper penetrance is obtained for longer wavelengths and for smaller angles to the surface normal within the limit of the critical angle. In typical assays, fluorophores are detected within about 200 nm from the surface, which corresponds to the contour length of about 600 base pairs of a polynucleotide. In some embodiments, when longer polynucleotide templates are analyzed, the polymerizing agent rather than the template or primer can be immobilized to the surface so that reaction occurs near the surface at all times. In some embodiments, a prism-type TIRF geometry for single-molecule imaging, as described by Xu and Yeung, is used (see, X-H. N. Xu et al., Science, 281, 1650 (1998)). In some embodiments, an objective type TIRF is used to provide space above the objective so that a microfluidic device can be used (see, e.g., Tokunaga et al., Biochem Biophy Res Commu 235: 47-53, 1997; Ambrose et al., Cytometry 36: 224; 1999; and Braslavsky et al, Applied Optics 40:5650, 2001).

Total internal reflection can be utilized with high numerical aperture objectives (ranging between about 1.4 and about 1.65 in aperture), for example, using an inverted microscope. The numerical aperture of an objective is a function of the max angle that can be collected (or illuminated) with the objective in a given refractive index of the media (i.e., $NA=n*\sin(\theta max)$). If $\theta max$ is larger than $\theta critic$ for reflection, some of the illuminated rays will be totally internal reflected. Using the peripheral of a large NA objective, one can illuminate the sample with TIR through the objective and use the same objective to collect the fluorescence light. That is, in certain embodiments the objective can play double roles as a condenser and an imaging objective.

In certain embodiments, single molecule detection can be achieved using flow cytometry where flowing samples are passed through a focused laser with a spatial filter used to define a small volume. U.S. Pat. No. 4,979,824 describes a device for this purpose. U.S. Pat. No. 4,793,705 describes a detection system for identifying individual molecules in a flow train of the particles in a flow cell. It further describes methods of arranging a plurality of lasers, fluorescence filters and detectors for detecting different fluorescent nucleic acid base-specific labels. U.S. Pat. No. 4,962,037 also describes a method for obtaining an ordered train of labeled nucleotides for obtaining DNA and RNA sequences using an exonuclease to cleave the bases. Single molecule detection on solid supports is also described in Ishikawa, et al. (1994). Single-molecule detection by laser-induced fluorescence technique with a position-sensitive photon-counting apparatus is also described, Jan. J Apple. Phys. 33: 1571-1576. Ishikawa describes a typical apparatus involving a photon-counting camera system attached to a fluorescence microscope. Lee et al. (Anal. Chem., 66: 4142-4149, 1994) describes an apparatus for detecting single molecules in a quartz capillary tube. The selection of lasers is dependent on the labeling moiety and the quality of light required. For example, diode, helium neon, argon ion, argon-krypton mixed ion, and double Nd:YAG lasers are useful in this invention.

C. Excitation and Scanning

In some embodiments, fluorescent excitation is exerted with a Q-switched frequency doubled Nd YAG laser, which has a KHz repetition rate allowing many samples to be taken per second. For example, a wavelength of about 532 nm is ideal for the excitation of rhodamine. It is a standard device that has been used in the single molecule detection scheme (Smith et al., Science 253:1122, 1992). Further, a pulsed laser allows time resolved experiments, which are useful for rejecting extraneous noise. In some embodiments, excitation can be performed with a mercury lamp and signals from the incorporated nucleotides can be detected with a CCD camera (see, e.g., Unger et al., Biotechniques 27:1008, 1999).

In some embodiments, the scanning system may be able to reproducibly scan the substrate (e.g., synthesis channels in the apparatuses). Where appropriate, e.g., for a two dimensional substrate, the scanning system may positionally define the templates or primers attached thereon to a reproducible coordinate system. Positional identification may be repeatable in successive scan steps, allowing correlation of the positions of identified signals.

Incorporated signals can be detected by scanning the substrates or the synthesis channels. The substrates or synthesis channels can be scanned simultaneously or serially, depending on the scanning method used. The signals can be scanned using a CCD camera (TE/CCD512SF, Princeton Instruments, Trenton, N.J.) with suitable optics (Ploem, J. S., in Fluorescent and Luminescent Probes for Biological Activity, Mason, T. W., Ed., Academic Press, London, pp. 1-11, 1993), such as described in Yershov et al. (Proc. Natl. Acad. Sci. 93:4913, 1996), or can be imaged by TV monitoring (Khrapko et al., DNA Sequencing 1:375, 1991). For radioactive signals (e.g., $^{32}P$), a phosphorimager device can be used (Johnston et al., Johnston R. F., et al., Electrophoresis 11:355, 1990; and Drmanac et al., Drmanac, R., et al., Electrophoresis 13:566, 1992). These methods are particularly useful to achieve simultaneous scanning of multiple probe-regions.

Various scanning systems can be employed in the methods and apparatus of the present invention. For example, electro-optical scanning devices described in, e.g., U.S. Pat. No. 5,143,854, are suitable for use with the present invention. The system could exhibit many of the features of photographic scanners, digitizers or even compact disk reading devices. For example, a model no. PM500-A1 x-y translation table manufactured by Newport Corporation can be attached to a detector unit. The x-y translation table is connected to and controlled by an appropriately programmed digital computer such as an IBM PC/AT or AT compatible computer. The detection system can be a model no. R943-02 photomultiplier tube manufactured by Hamamatsu, attached to a preamplifier, e.g., a model no. SR440 manufactured by Stanford Research Systems, and to a photon counter, e.g., an SR430 manufactured by Stanford Research System, or a multichannel detection device. Either digital or analog signals may be advantageous in different embodiments or aspects of the invention.

The stability and reproducibility of positional localization in scanning of the invention may determine the resolution for detecting closely positioned polynucleotide clusters on a two-dimensional substrate. High resolution scanning, for example, allows successive monitoring at a given position, mapping the results of repeated reaction cycles to one or more positionally-mapped polynucleotides or polynucleotide complexes. As the resolution increases, the number of possible polynucleotides that can be sequenced on a single substrate also increases. Crude scanning systems can resolve only on the order of about 1000 µm, refined scanning systems can resolve on the order of about 100 µm, more refined systems can resolve on the order of about 10 µm, and with optical magnification systems a resolution on the order of about 1.0 µm is available. The resolution limit can depend on diffraction limits and advantages can arise from using shorter wavelength radiation for fluorescent scanning steps. However, with increased resolution, the time required to fully scan a substrate can increase and a compromise between speed and resolution may be selected. Parallel detection devices, which provide high resolution with shorter scan-times, are applicable, for example, where multiple detectors are moved in parallel.

In some applications, sensitivity may be more important than resolution. However, the reliability of a signal can be pre-selected by continuing to count photons for longer periods of time at positions where intensity of signal is lower. Although this may decrease scan speed, it can increase reliability of the signal determined. Various signal detection and processing algorithms can be incorporated into the detection system. In some embodiments, the distribution of signal intensities of pixels across the region is evaluated to determine whether the distribution of intensities corresponds to a time positive signal.

In some embodiments, detecting correlates intensity with the number of incorporated nucleotides. For example, by measuring increase of fluorescence as nucleotides are incorporated and quantifying the increase, the number of nucleotides bearing a given fluorescent moiety may be calculated.

D. Sample Detection of Fluorescent Labeling Moieties

Briefly, the polynucleotide templates can be prepared as described above (e.g., cloned in single-stranded M1 3 plasmid, biotinylated, and attached to the surface of a substrate, e.g., the surface of a synthesis channel, which has been pretreated using the PEM technique). After the primed, single stranded DNA is anchored to the substrate, e.g. to the synthesis channel in the flow cell, a polymerizing agent and a nucleotide, e.g. dATP, may be flowed into the flow cell. A high fidelity polymerizing agent with no exonuclease proofreading ability can be used. If the first base of the DNA sequence following the primer is T, then the polymerizing incorporates the dATP's bearing fluorescent moieties as labels. If the first base is anything else, no fluorescent molecules become incorporated. The reagents can then be flowed out of the flow cell, and the fluorescence of the polynucleotide measured. If no fluorescence is detected, the procedure can be repeated with one of the other nucleotides. If fluorescence is detected, the identity of the first base in the sequence has been determined. The fluorescence can be excited with, e.g., a Q-switched frequency doubled Nd YAG laser (Smith et al., Science 253: 1122, 1992).

In certain embodiments, each of the nucleotides employed has a detectably-distinguishable fluorophore associated with it. In such embodiments, a four-color instrument can be used having four cameras and four excitation lasers or the image could be split to four quarters and imaged by a single camera. For example, the micro-imager of Optical Insights LTD can split the image to four different images in four different spectra in front of the port of the camera. Illumination with only one laser excitation for four colors is possible if suitable dyes are used (see, e.g., Rosenblum et al, Nucleic Acids Research 25: 4500, 1997). For example, the BigDyes, available from Applied Biosciences, have single excitation wavelength spectrum and four different emission wavelength spectrums. (http://www.appliedbiosystems.com/products/productdetail.cfin?ID=82). Nanocrystals also have a variety of emission wavelengths for a given excitation (see, e.g., U.S. Pat. No. 6,309,701; and Lacoste et al., Proc. Natl. Acad. Sci. USA 97: 9461-6, 2000). Thus, it is possible to use such optical setups to analyze a sequence of a polynucleotide. Moreover, many different polynucleotide molecules immobilized on a substrate (e.g., a microscope slide) can be imaged and sequenced simultaneously.

In certain embodiments, the substrates (or, e.g., the synthesis channels) can be serially scanned one by one, or row by row using a fluorescence microscope apparatus, such as described in U.S. Pat. Nos. 6,094,274, 5,902,723, 5,424,186, and 5,091,652. In some embodiments, standard lowlight level cameras, such as a SIT and image intensified CCD camera, are employed (see, Funatsu et al., Nature 374, 555, 1995). An ICCD can be preferable to a cooled CCD camera because of its better time resolution. These devices are commercially available (e.g., from Hammamatsu).

Alternatively, only the intensifier unit from Hammarnatsu or DEP may be used and incorporated into other less expensive or home built cameras. If necessary, the intensifier can be cooled. A customarily-built camera can allow greater flexibility in component-choice in a higher performance device. Using a camera instead of an avalanche photodiode can provide the advantage of imaging the whole field of view. This extra spatial information allows the development of new noise reduction techniques. For example, one can use the fact that signals are expected from certain spatial locations (i.e. where the polynucleotide template is attached) in order to reject noise.

In some embodiments, polynucleotide sequences are analyzed with a fluorescent photobleaching method. Fluorescently labeled nucleotides can be used in the primer extension, and signals from the incorporated nucleotides can be removed by photobleaching before the next extension cycle. That is, the fluorescence signal can be photobleached and in some cases extinguished before the procedure is repeated for the next base in the template sequence.

In certain embodiments, only a fraction of each type of nucleoside triphosphate is fluorescently labeled. That is, only a fraction (e.g., less than about 10%, about 5%, about 1%, about 0.1%, about 0.01%, or about 0.001%) of each type of nucleotide triphosphate may be fluorescently labeled (e.g., rhodamine-labeled nucleotide triphosphates from NEN DuPont can be used).

E. Detection Using Fluorescence Resonance Energy Transfer (FRET)

In some embodiments of the present invention, incorporation of different types of nucleotides into a primer is detected using different fluorescent labeling moieties on the different types of nucleotides. One class of fluorescent dyes which has been developed is the fluorescence resonance energy transfer (FRET) dyes, including donor and acceptor energy fluorescent dyes and linkers useful for DNA sequencing. When two different labels are incorporated into the primer in close vicinity, signals due to fluorescence resonance energy transfer (FRET) can be detected. FRET is a phenomenon that has been well documented in the literature, e.g., in T. Foster, Modem Quantum Chemistry, Istanbul Lectures, Part III, 93-137, 1965, Academic Press, New York; and Selvin, "Fluorescence Resonance Energy Transfer," Methods in Enzymology 246: 300-335, 1995.

In FRET, one of the fluorophores (donor) has an emission spectrum that overlaps the excitation spectrum of the other fluorophore (acceptor) and transfer of energy takes place from the donor to the acceptor through fluorescence resonance energy transfer. The energy transfer is mediated by dipole-dipole interaction. Spectroscopically, the acceptor moiety is a fluorophore which is excited at the wavelength of light emitted by the excited donor moiety. When excited, the donor moiety transmits its energy to the acceptor moiety. Therefore, emission from the donor is not observed. Rather, emission from the donor excites the acceptor, causing the acceptor to emit at its characteristic wavelength (i.e., a wavelength different from that of the donor and observed as a different color from that of the donor).

In FRET, when the donor is excited, its specific emission intensity decreases while the acceptor's specific emission intensity increases, resulting in fluorescence enhancement. Also, attachment of acceptor moieties with differing emission spectra allow differentiation among different nucleotide base-types by fluorescence using a single excitation wavelength.

Moreover, the donor excites acceptors only within the Foster radius of a given FRET pair, thus creating a highly localized excitation source and reducing background noise from moieties outside this Foster radius. For example, FRET signals can be detected from individual polynucleotides when a donor-acceptor pair are incorporated into the same target polynucleotide-primer complex.

FRET pairs can be chosen to have a given Foster radius, for example, about 1 nm, about 2 nm, about 3 nm, about 4 nm, about 5 nm, about 6 nm, about 7 nm, about 8 nm, about 9 nm, or about 10 nm. Noise from any non-specific attachment of fluorescently-labeled nucleotides to the surface of the substrate can become small, as the effective region of fluorescent illumination will only be a few nanometers. Furthermore, for photo bleaching, bleaching radiation may be selected to extinguish signal from the acceptor but not the donor, facilitating repeated used of the same donor moiety with different acceptor moieties, as described above.

Detection of single molecule FRET signal reveals sequence information and facilitates interpretation of the sequencing data. Detection of FRET signal in the present invention can be performed accordingly to various methods described in the art (e.g., U.S. Pat. No. 5,776,782). FRET has been used to study various biological activities of biomacromolecules including polynucleotides. For example, Cooper et al. disclosed fluorescence energy transfer in duplex and branched DNA molecules (Biochemistry 29: 9261-9268, 1990). Lazowski et al. reported highly sensitive detection of hybridization of oligonucleotides to specific sequences of nucleic acids by FRET (Antisense Nucleic Acid Drug Dev. 10: 97-103, 2000). Methods for nucleic acid analysis using FRET were also described in U.S. Pat. Nos. 6,177,249 and 5,945,283. Efficacy of using FRET to detect multiple nucleotides incorporation into a single polynucleotide molecule is exemplified in Example 8 of the present application.

Any of a number of fluorophore combinations can be selected as donor-acceptor pair for labeling the nucleotides in the present invention for detection using FRET signals (see for example, Pesce et al,. eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; which are incorporated by reference). In general, a donor fluorophore is selected that has a substantial spectrum overlap with that of the acceptor fluorophore. That is, the acceptor fluorophore's excitation spectrum can substantially overlap the emission spectrum of the donor fluorophore. Furthermore, it may also be desirable in certain applications that the donor have an excitation maximum near a laser frequency such as Helium-Cadmium 442 nm or Argon 488 nm. In such applications, the use of intense laser light can serve as an effective means to excite the donor fluorophore. Moreover, the wavelength maximum of the emission spectrum of the acceptor moiety can be at least about 10 nm greater than the wavelength maximum of the excitation spectrum of the donor moiety. That is, the emission spectrum of the acceptor fluorophore can overlap with and be shifted compared to the donor spectrum.

Suitable donors and acceptors operating on the principle of fluorescence energy transfer include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy5; Cy5.5; Cy7; IRD 700; IRD 800; La Jolla Blue; phthalo cyanine; and naphthalo cyanine.

In certain embodiments, the donor fluorescent moiety is coupled to the primer, and energy is detected from acceptors on nucleotides as they are incorporated into the extending primer. Other detecting techniques identifying interaction or correlation between a labeling moiety on a primer and a labeling moiety on a nucleotide may also be used.

In certain embodiments, the donor fluorescent moiety is coupled to the polymerizing agent, and energy is detected from acceptors on incorporated nucleotides. Other detecting techniques identifying interaction or correlation between a labeling moiety on a polymerizing agent and a labeling moiety on a nucleotide may also be used.

Another approach to reducing background involves "turning on" a labeling moiety as it becomes incorporation into the complementary strand. For example, some embodiments use nucleotides comprising a fluorescent labeling moiety and a quenching moiety. Locating the quenching moiety on the β- or γ-phosphate of a nucleotide triphosphate quenches fluorescence from unincorporated nucleotides, while allowing fluorescence from incorporated nucleotides. This makes use of the chemistry of nucleotide incorporation, in which the β- and γ-phosphates of a nucleotide triphosphate are released during the incorporation reaction as pyrophosphate, to "turn on" the labeling moiety on incorporated nucleotides.

Additional techniques may be used to suppress background interference and/or improve detection of fluorescent labels. These include, for example, spectral wavelength discrimination and fluorophore identification. Further, increases or decreases in fluorescent intensity may be measured and quantified, to correlate signal intensity with the number of incorporated nucleotides. Certain embodiments can utilize additional visualization techniques, including for example single and/or multiphoton excitation, light scattering, dark field microscopy, and/or photoconversion. In yet other embodiments, detection can be carried out by non-optical and/or electronic procedures, as outlined below.

F. Quantum Dots

Another means of detection involves using quantum dots as the labeling moiety. A quantum dot is a nanoscale metal or semi-conductor particle. A quantum dot can be made to fluoresce in various colors for days, months, and perhaps years. http://www.sciencenews.org/20030215/bob10.asp. In some embodiments, the semiconductor particles are made of a cadmium selenide core surrounded by a shell of, for example, zinc sulfide, silicon, or polymer. Upon excitation with a light source, a quantum dot emits a particular color based on its size, where smaller dots fluoresce at shorter wavelengths (e.g., blue wavelengths) and bigger dots emit longer wavelengths (e.g. red wavelengths).

Quantum dot diameters can be about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, and about 15 nm. Different dot sizes may be used to create detectably distinguishable labeling moieties for attaching, for example, to different nucleotide base-types. Further, intensity can increase proportionally with the number of dots, permitting correlation of the signal intensity with the number of incorporated nucleotides.

The quantum dot may be attached to any position on the nucleotide base, sugar, and/or α-phosphate, with or without a linker, where the nucleotide bearing the dot remains capable of base-complementary incorporation by a polymerizing agent into a growing complementary strand.

G. Non-Optical Detection

Other than fluorescently-labeled nucleotides and optical detection devices, other methods of detecting nucleotide incorporation are also contemplated in the present invention, e.g., in bulk sequencing applications, including the use of mass spectrometry to analyze the reaction products, the use of radiolabeled nucleotides, as well as electronic means, the detection of reaction products using "wired enzymes", and reactive labeling moieties and/or enzymatic labeling moieties.

In some embodiments, mass spectrometry is employed to detect nucleotide incorporation in the primer extension reaction. A primer extension reaction generally consumes a nucleotide triphosphate, adds a single base to the primer/template complex, and produces pyrophosphate as a by-product. Mass spectrometry can be used to detect released pyrophosphate, after providing one or more nucleotides in the presence of the template and a polymerizing agent. The absence of pyrophosphate indicates that the nucleotide was not incorporated, whereas the presence of pyrophosphate indicates incorporation. Detections based on pyrophosphate release have been described in the art, e.g., in WO98/13523, WO98/28440, and Ronaghi et al., Science 281:363, 1998.

Certain embodiments use radiolabeled nucleotides. Nucleotides can be radiolabeled either at the sugar, the base, and/or the phosphate groups. To detect radioactivity, a small radioactivity sensor can be incorporated in the substrate. A CCD pixel, for instance, serves as a good detector for some radioactive decay processes. Radiolabeling of the sugar and/or base produces an additive signal: each incorporation increases the amount of radiolabel in the primer-template complex. If the nucleotide is labeled in the portion that is released as pyrophosphate (e.g. dNTP labeled with β- or γ-$^{32}$P), the radioactive pyrophosphate can be detected, for example in the wash stream. This radioactivity level need not be additive, but rather can be binary for each attempted nucleotide addition. Consequently, subsequent additions may pose no limit on the read length. Due to the small reagent consumption and the contained nature of microfluidics, the total radioactivity used in such a system may be relatively minimal, and containment relatively simple.

Certain embodiments detect incorporation electronically. Electronic procedures, include, for example, the use of sensitive electronic DNA detectors, such as ones developed by NASA Ames Research Center, which employ a forest of carbon nanotubes to sense small amounts of polynucleotides. See, e.g., http://www.trnmag.corn/Stories/2003/073003/Chip$_{13}$senses_trace_DNA_073003.html. The sensitivity of such a device is based on its small size and the electronic properties of carbon nanotubes. For example, the device uses arrays of about 2- to about 200-square-micron chromium electrodes on a silicon wafer. Multi-walled nanotubes ranging from about 30 to about 50 nanometers are packed onto the electrodes at densities of anywhere from about 100 million to about 3 billion nanotubes per square centimeter. One end the nanotube contacts the electrode and the other is exposed at the surface where target polynucleotides can be attached. Addition of complementary bases can increase the flow of electrons through the nanotubes to the electrode. In some embodiments, the device may be sensitive enough to detect a few million to a few thousand polynucleotide molecules and can be used in the practice of certain embodiments of the present invention to detect single base extension.

Other electronic means of detecting polynucleotides have also been described. For example, Firtz et at, *Electronic detection of DNA by its intrinsic molecular charge*, PNAS 2002, have reported selective and real-time detection of DNA using an electronic readout. In such embodiments, microfabricated silicon field-effect sensors are used to directly monitor the increase in surface charge when polynucleotide strands hybridizes on the sensor surface. Nanomolar polynucleotide concentrations can be detected, for example, in bulk sequencing by synthesis applications.

Some embodiments using non-optical detection of pyrophosphate release make use of "wired redox enzymes" as described, e.g., in Heller et al., Analytical Chemistry 66: 245 1 2457, 1994; and Ohara et al., Analytical Chemistry 65:3512-3517, 1993. Briefly, enzymes can be covalently linked to a hydrogel matrix containing redox active groups capable of transporting charge. The analyte to be detected is either acted on directly by a redox enzyme (either releasing or consuming electrons) or consumed as a reagent in an enzymatic cascade that produces a substrate that is reduced or oxidized by a redox enzyme. The production or consumption of electrons is detected at a metal electrode in contact with the hydrogel. For the detection of pyrophosphate, an enzymatic cascade using pyrophosphatase, maltose phosphorylase, and glucose oxidase can be employed. Pyrophosphatase converts pyrophosphate into phosphate; maltose phosphorylase converts maltose (in the presence of phosphate) to glucose 1-phosphate and glucose. Then, glucose oxidase converts the glucose to gluconolactone and $H_2O_2$; this final reaction is the redox step which gives rise to a detectable current at the electrode. Glucose sensors based on this principle are well known in the art, and enzymatic cascades as described here have been demonstrated previously. Other enzymatic cascades besides the specific example given here are also contemplated in the present invention. This type of detection scheme allows direct electrical readout of nucleotide incorporation at each reaction chamber or location, allowing easy parallelization.

As outlined above, some embodiments use nucleotides comprising a reactive moiety that can undergo a reaction, for example, following incorporation, to create a detectable product. In such embodiments, detection of the product can identify incorporation of the nucleotide. Reactive moieties include, for example, biotin as in biotin-dUTP; digioxin, as in digioxin-dUTP; fluorescein, as in fluorescein-dUTP; and the like. Such reactive moieties bind to a corresponding member of a binding pair, which is itself conjugated to an enzymatic moiety that produces a detectable reaction product. For example, biotin-dUTP can bind horse peroxidase-conjugated streptavidin; digioxin-dUTP can bind horseradish peroxidase-conjugated antidigoxin; and fluorescein-dUTP can bind alkaline phosphatase-conjugated anti-fluorescent antibody. Additional enzymatic moieties include galactosidase, luciferase, or acetylcholinesterase. Standard methods are known in the art for detecting reaction products of these enzymatic moieties. Moreover, in certain other embodiments, the enzymatic moiety can be attached to the nucleotide itself, and similarly detected by production of a reaction product.

VII. Modes of Analysis

A. Movie Mode

Certain embodiments of the present invention involve visualizing incorporation of labeled nucleotides into immobilized polynucleotide molecules in a time resolved manner, with single molecule resolution. This involves a dynamic rather than a static approach to sequence analysis, where the dynamic approach is termed "movie mode."

The present invention allows both static and dynamic approaches. The static approach involves adding just one type of nucleotide bearing a labeling moiety to the polymerization reaction at any given time. The signal is incorporated into the primer if the next template residue in the target polynucleotide is the complementary type. This may be repeated with each of the other three types of nucleotides until the correct residue is incorporated.

In the dynamic approach, all four types of nucleotides (with at least one type bearing a labeling moiety) are simultaneously present, and incorporation of the signals into the complementary strand is monitored temporally. For example, incorporated signals are imaged continuously, preferably at a rate faster than the rate at which the nucleotides are incorporated into the primer. As the polymerizing agent continues along the target polynucleotide, the polynucleotide sequence can be determined from the temporal order of the incorporated labeling moieties into the growing complementary strand.

In some embodiments, multiple types of labeled nucleotides (e.g., 2 to 4 types each labeled with a different labeling moiety) can be added at the same time for the extension reactions. For example, polynucleotide sequence analysis can be accomplished by using four different labeling moieties on each of the four types of nucleotides. Incorporated signals are imaged and then optionally neutralized before further incorporation cycles. Runs of identical bases (e.g., AAAAA) can be identified by, for example, monitoring the intensity of the signal so that the number of labels at an emitting spot can be quantitatively determined.

Certain embodiments use fewer than four types of labeling moieties and less than all four of the nucleotides are labeled. In some embodiments, for example, only one type of labeled nucleotide is added at a step, and each extension cycle may comprise four such steps in order to observe the incorporation at the next complementary nucleotide. Alternatively, two types of nucleotides can be labeled with the same or detectably distinguishable labeling moieties. By repeating the experiment with different pairs (e.g., AT, AG, AC, TG, TC, GC), the original nucleotide sequence can be delineated. Similarly, three types of nucleotides can be labeled with the same or detectably distinguishable labels.

Certain embodiments use fewer than four types of labeling moieties, but all four of the nucleotides are labeled. For example, using three different labeling moieties, each of three types of nucleotides can bear a detectably distinguishable labeling moiety, and the fourth type can bear the same labeling moiety as one of the other three types. In such embodiments, the analysis would need to be repeated at least twice to determine the sequence of the target polynucleotide, while repeating three times would increase accuracy. Alternatively, using two different labeling moieties, one of the four types of nucleotides can bear one labeling moiety detectably distinguishable from the second labeling moiety used on the other three types of nucleotides. In such embodiments, the analysis would need to be repeated at least three times to determine the sequence of the target polynucleotide, while repeating four times would increase accuracy.

Certain embodiments of the present invention are also useful in obtaining partial sequence information of a target polynucleotide, e.g., by using only two or three labeled nucleotide species. The relative positions of two or three nucleotide species in the sequence in conjunction with known sequence databases can facilitate determination of the identity of the target sequence, i.e., whether it is identical or related to a known sequence. For example, only two detectably distinguishable labeling moieties can be used to identify already-sequenced regions. As an illustration, out of a known universe of RNA transcripts, two colors would provide color patterns allowing identification. Such approaches are useful, for example, in determining gene expressions by re-sequencing RNA transcripts and cDNA libraries. Such approaches are also useful in detecting mutations, such as SNPs or cancer mutations, in known genomic sequences.

B. Bulk Analysis

Certain embodiments of the present invention are directed to bulk analysis of a plurality of target polynucleotides in parallel, where the incorporation/extension reaction is performed with multiple copies of the template polynucleotide. For example, the experiment may involve simultaneously analyzing the sequences of a plurality of copies of the same or different target polynucleotides at a plurality of different locations on an array.

C. Asynchronous and Short-Cycle Sequencing

Figure 17:
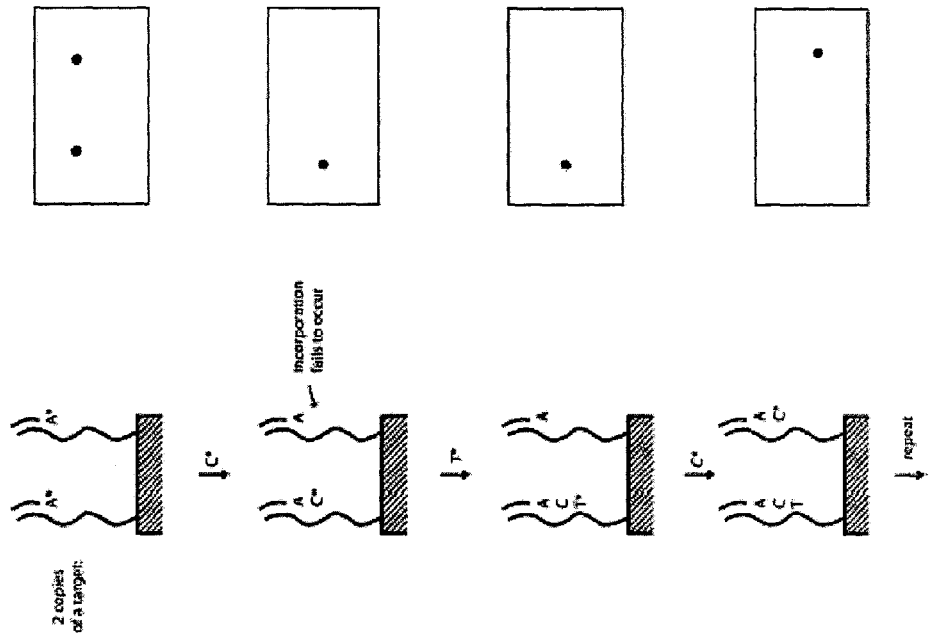
FIG. 17 is a schematic illustration and top field view of the asynchronous nature of single molecule sequencing, where it does not matter if a base incorporates at some but not all copies of a given target polynucleotide.

Another aspect of the present invention features the advantages of asynchronous sequencing. As the invention involves sequencing at the single molecule level, there is no need to average information from many different targets. Thus, in some embodiments as illustrated in FIG. 17, if an incorporation reaction fails to occur on a particular target polynucleotide, it can be completed in a later cycle without producing erroneous information, or interfering with data from other target molecules being analyzed in parallel. Some embodiments feature a method of analyzing a sequence of target polynucleotides by allowing incorporation of nucleotides into complementary strands, where different numbers of nucleotides may be incorporated into different complementary strands in a given period of time. Later, a nucleotide that was not incorporated into at least one of the strands previously, but that subsequently becomes incorporated, can be identified. That is, a nucleotide that failed to be incorporated on a particular target at a given time can "catch up" later without adversely affecting sequencing information.

The example illustrated in FIG. 17 indicates asynchronous incorporation into two copies of a given target polynucleotide. A cytosine ("C") incorporates into the extension product of one copy of a target polynucleotide, but fails to incorporate into the other copy. During subsequent cycles of incorporation, however, a C can become incorporated, without adversely affecting sequencing information. Hence, it does not matter if an incorporation is missed now and then.

Figure 18:
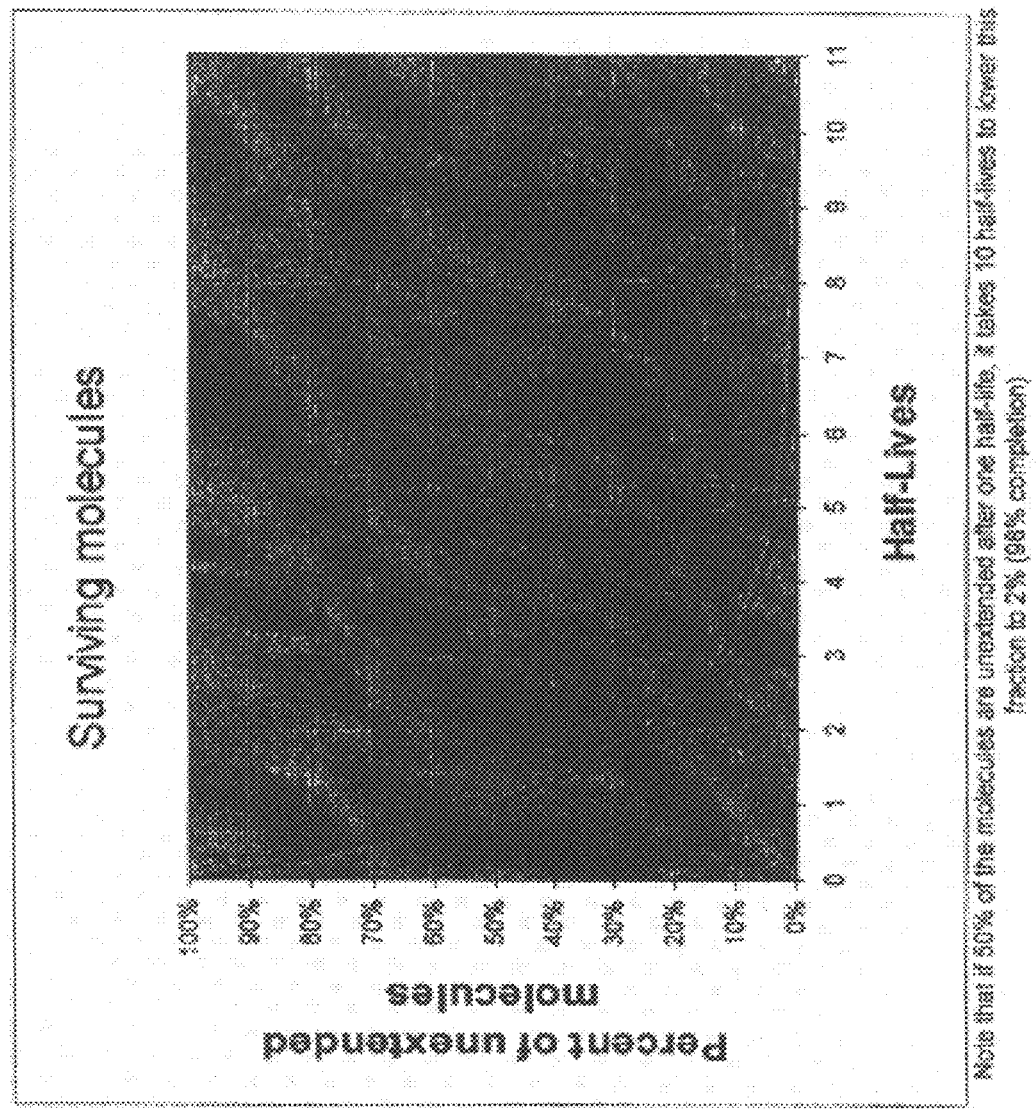
FIG. 18 illustrates a principle behind asynchronous short-cycle sequencing, that is, obtaining incorporation in 99% of complementary strands requires a period of several half-lives of the incorporation reaction, where one half-life is the time taken for at least one incorporation to occur in 50% of the complementary strands. On the other hand, shorter cycles leave a greater percentage of complementary strands un-extended.

Asynchronous incorporation also overcomes the need to run a cycle of incorporation to completion or even to near completion, facilitating the use of short-cycles. In attempting to obtain a complementary strand of a given number of bases, conventional chemistry teaches one to run each incorporation reaction to as close to completion as possible to improve yield. For example, nucleotides may be allowed to react in the presence of a polymerizing agent until at least one becomes incorporated into at least 99% of the complementary strands. This would produce a yield of $(0.99)^n \times 100\%$ for a complementary strand extended by n nucleotides. FIG. 18 illustrates that obtaining incorporation in 99% of the complementary strands, however, requires a period of several half-lives of the incorporation reaction, where one half-life is the time taken for at least one incorporation to occur in 50% of the complementary strands. Classically, the more strands that complete an incorporation during each cycle, the more n-mers obtained after n cycles. Nonetheless, in asynchronous incorporation, an incorporation that failed to occur on a particular target in one cycle can "catch up" in later cycles, permitting the use of shorter, even if more numerous, cycles.

Accordingly, another aspect of the present invention features a short-cycle sequencing method for analyzing a sequence of a target polynucleotide. Certain embodiments involve allowing a cycle of incorporation reactions of a number of nucleotides into a complementary strand, halting the cycle after a relatively short period of time, and detecting incorporation. In such embodiments, halting occurs when only a small proportion of the stands have been extended, or when a large proportion of the strands have only been extended by a few nucleotides. For example, the cycle period may permit some chance of incorporation of two or less nucleotides into a given complementary strand. The cycle period may be conveniently measured in half lives of the incorporation reaction, for example, a period of less than one to a few half lives. Halting may be carried out by washing or flushing out the nucleotides that remain unincorporated and/or washing or flushing out polymerization agent. The method can be repeated for a number of short cycles to sequence additional nucleotides of the target polynucleotide by short-cycle sequencing. Further, many aspects of the repeated cycles may be automated, for example, using microfluidics for washing nucleotides to sites of anchored target polynucleotides, and washing out unincorporated nucleotides to halt each cycle.

In certain embodiments, the target polynucleotide comprises a homopolymer stretch of consecutive repeats of a given nucleotide base (e.g. AAAAAAAAAA) (SEQ ID NO: 10). In certain embodiments, nucleotides of the same type bear the same labeling moiety (e.g. all A's carry a red fluorescent dye). A long repeat of the same incorporated signal can be read in short-cycle sequencing as only a few nucleotides will be incorporated during each cycle. Signal from the few incorporated nucleotides can be detected and neutralized and/or reduced before subsequent cycles are carried out. Signals can be removed after each cycle or after a number of cycles, for example, after a number of cycles that would result in too many incorporated nucleotides for quantification.

In some embodiments, signal is reduced by bleaching, including chemical bleaching and photobleaching. In some embodiments, signal is reduced by removing all or a portion of the labeling moiety from incorporated nucleotides. The portion removed may be the signal generating portion. Removal may involve cleaving by chemical, enzymatic or photo-chemical means. Removing can be carried out after about one, about two, about three, about four, or about five cycles, depending, for example, on the number of nucleotides allowed to be incorporated per cycle and the ability of the detection means used to distinguish between increasing numbers of incorporated labeling moieties.

It will be appreciated that short-cycle sequencing can overcome problems of reading homopolymer stretches in sequencing by synthesis methods, without using chain termination nor blocking moieties, such as chain elongation inhibitors. While detection techniques may be able to quantify signal intensity from a smaller number of incorporated nucleotides of the same base-type, for example two or three incorporated nucleotides, longer runs of identical bases may not permit quantification due to increasing signal intensity. That is, it may become difficult to distinguish n bases from n+1 bases, where the fractional increase in signal intensity from the $(n+1)^{th}$ base is small relative to the signal intensity from the already-incorporated n bases.

In embodiments using short-cycles, however, it is possible to limit the number of nucleotides that become incorporated in a given cycle. For example, it can be determined by simulation that using a cycle period of about 0.8 half-lives can result in two or less incorporations in nine out of ten homopolymer complementary strands. (See Example 11b). In another simulation, a 0.8 half-life period was shown to allow no more than two incorporations in about 96.0% of 200 homopolymer complementary strands. As detection means can more readily quantify signal intensity from the smaller number of incorporated nucleotides rather than from larger numbers, the use of short-cycles addresses this issue. For example, imaging systems known in the art can reliably distinguish the difference in signal intensity between one versus two fluorescent labeling moieties on consecutively-incorporated nucleotides. Other imaging systems can reliably distinguish the difference in signal intensity between two versus three fluorescent labeling moieties on consecutively-incorporated nucleotides.

Based on the methods disclosed herein, those of skill in the art will be able to determine the period of half-lives required to limit the number incorporations per cycle for a given number of target polynucleotides. (See Examples 11 and 12, FIGS. 19 and 20). Statistical simulations can also provide the number of repeated cycles needed to obtain a given number of incorporations, for example, to sequence a 25 base pair sequence. (See Examples 11 and 12, FIGS. 19 and 20). Referring to the simulations above, for example, it can be determined that 60 cycles, each 0.8 half-lives long, would be required for at least 25 incorporations in each of ten complementary strands (Example 11b, FIG. 19b). With 200 complementary strands, 60 cycles each 0.8 half-lives long produce at least 20 incorporations in each strand (Example 12, FIG. 20). Following the methodologies outlined herein, such as the simulated working examples detailed below, those of skill in the art will be able to make similar determinations for other numbers of targets of varying lengths, and use appropriate cycle periods and numbers of cycles to analyze homopolymer without using blocking moieties or reversible chain termination.

In some embodiments, the half life for the incorporation reaction is affected by the fact that polymerizing agent may incorporate labeled nucleotides less readily than unlabeled nucleotides. FIG. 21 illustrates the statistics of incorporation for a certain embodiment using a Klenow exo-minus polymerizing agent and Cy3- or Cy5- labeled nucleotides. The statistics show that polymerizing agent may incorporate repeated labeled nucleotides less readily than the first labeled nucleotide. That is, the first incorporation may take place more quickly than subsequent incorporations, which require a labeled base to be incorporated into a polynucleotide strand already containing an incorporated labeled base. Without being limited to any hypothesis, this may be due to the polymerizing agent having difficulty incorporating labeled nucleotides "on top of" an already incorporated labeled nucleotide. The graph of FIG. 21 indicates, for example, that it may take five to ten times longer, resulting in a "slowing down" of the incorporation reaction. In other embodiments, the slowing down may vary with the use of other labeled nucleotides, other polymerizing agents and various reaction conditions.

For example, the rate at which a polymerizing agent incorporates labeled nucleotides into a complementary strand may be slowed down by a factor of about 2, about 3, about 4, about 5, about 6, about 7, about 8, about 9, about 10, about 11, about 12, or about 15 times compared to that observed with unlabeled nucleotides or compared to that observed for the first incorporated labeled nucleotide. This "slowdown" can result in a longer half life for an incorporation reaction with a given homopolymer error rate.

Figure 22:
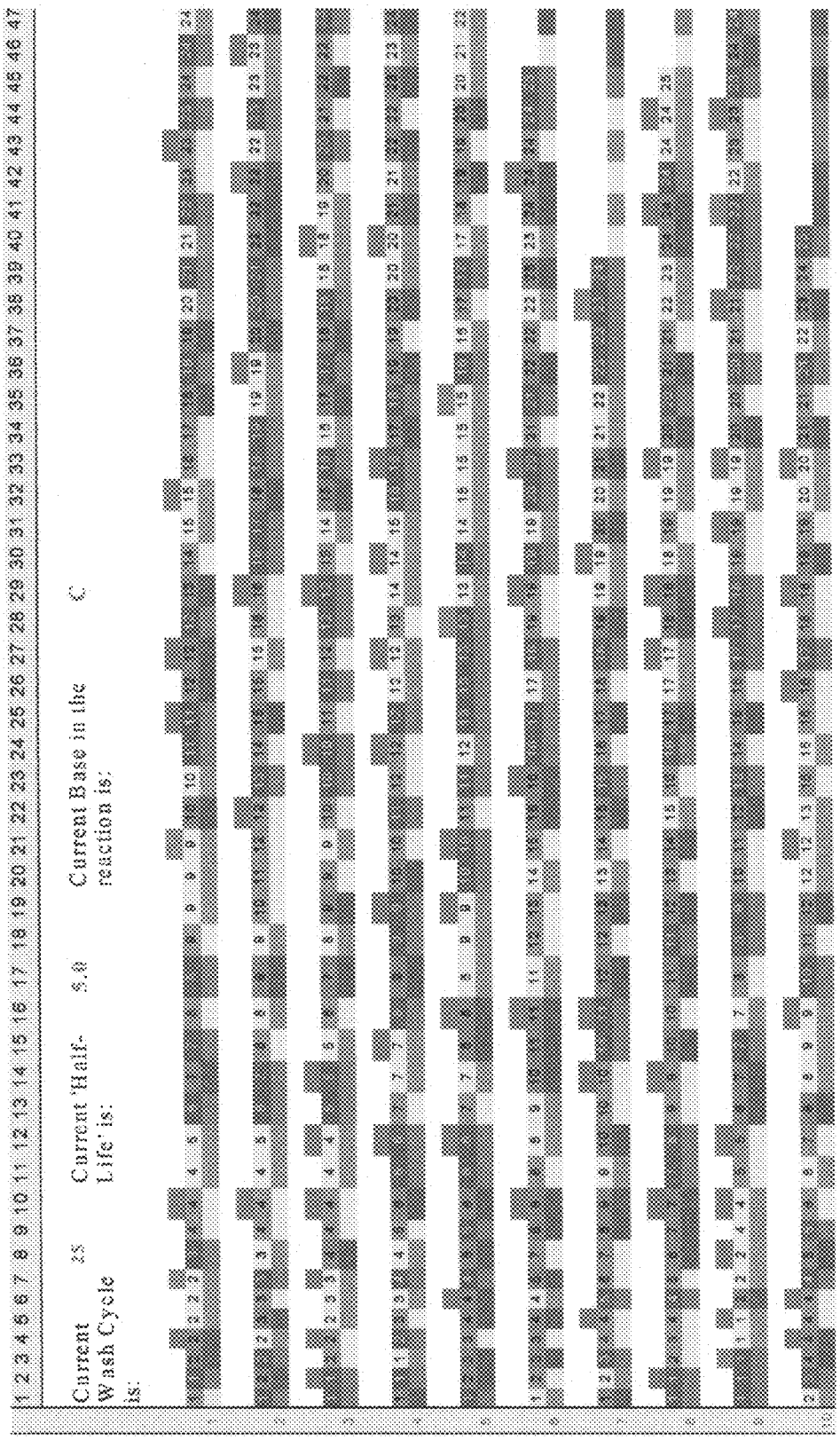
FIG. 22 illustrates a Monte Carlos simulation showing the effect of slowing down polymerizing agent and the lengthening of half lives on the cycle period for short cycle sequencing embodiments.
Figure 23:
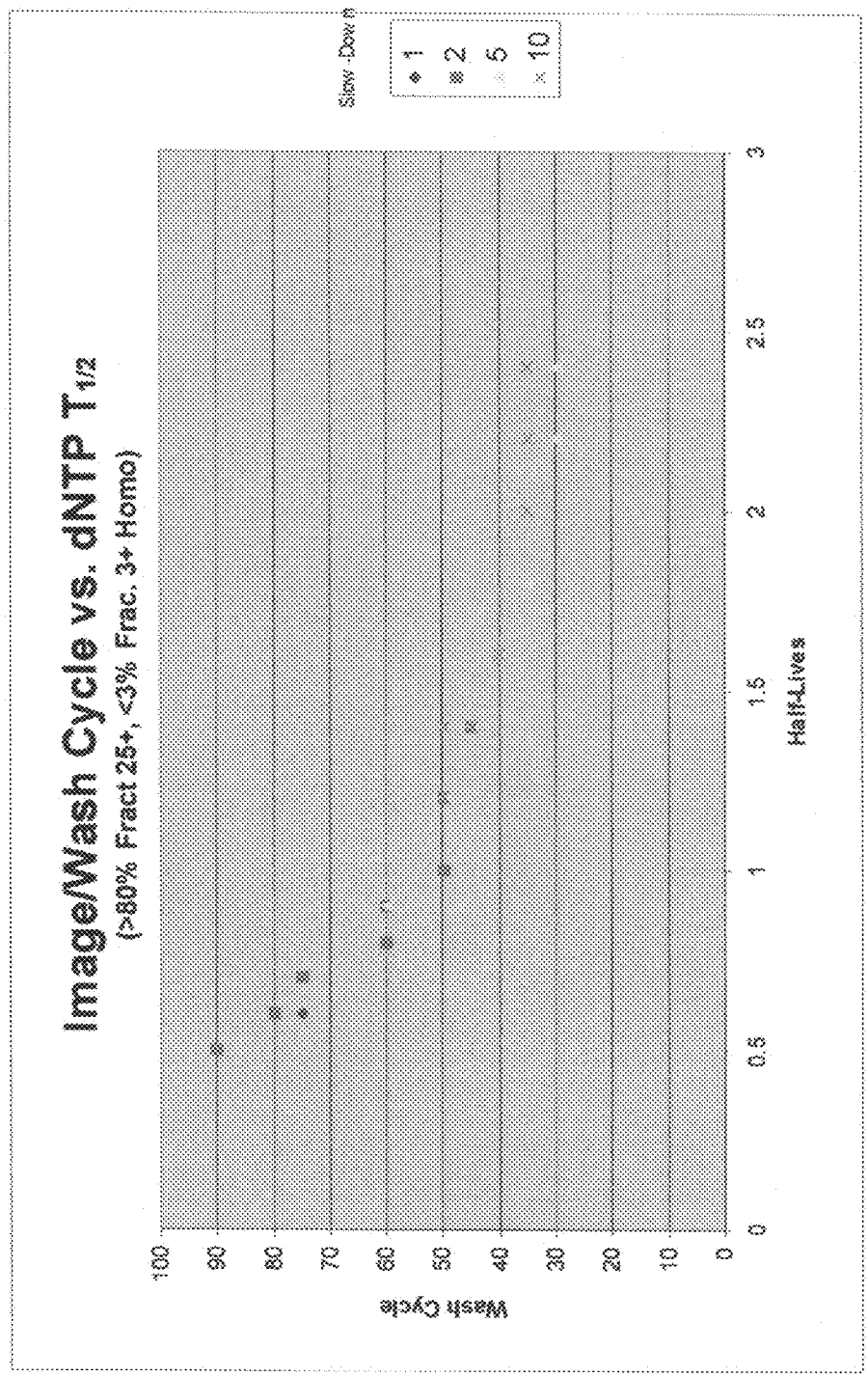
FIG. 23 illustrates the number of cycles needed with cycle periods of various half lives, taking into account slowdown factors of two (squares), five (triangles), and 10 (crosses), in order to obtain over 25 incorporations in over 80% of target hompolymers, with at least a 97% chance of incorporating two or less nucleotides per cycle (or a smaller than 3% chance of incorporating three or more nucleotides per cycle).

Moreover, this slowing down and longer half life can be taken into account when determining appropriate cycle periods and numbers of cycles to analyze homopolymer targets of a given length. FIGS. 22 and 23, for example, illustrate the results of Monte Carlos simulations accounting for these factors. The graph of FIG. 23, for example, shows the number of cycles needed with cycle periods of various half lives, taking into account slowdown factors of two (squares), five (triangles), and 10 (crosses), in order to obtain over 25 incorporations in over 80% of target hompolymers, with at least a 97% chance of incorporating two or less nucleotides per cycle (or a smaller than 3% chance of incorporating three or more nucleotides per cycle). As the graph shows, longer half lives permit fewer cycles to obtain the desired result while keeping the error rate low. That is, the longer half lives for a given homopolymer error rate permit the use of longer cycle periods, allowing more nucleotides to be incorporated per cycle, and hence requiring fewer numbers of repeated cycles to analyze a target sequence of given length at a given error rate. For example, as FIG. 23 illustrates, if the use of labeled nucleotides slows down polymerizing agent by a factor of 5, a cycle period of 2.4 half lives may be used to analyze over 80% of 25-mers in 30 cycles, where no more than two nucleotides incorporate over 97% of the time in any give cycle.

Based on the instant disclosures, those of skill in the art can determine the cycle period required to limit the number incorporations per cycle for a given number of target polynucleotides for a given half life, and the number of cycles required to analyze a sequence of a given length. That is, following the methodologies, simulations, and graphs provided herein, those of skill in the art will be able to make similar determinations for numbers of target polynucleotides of varying lengths, and use appropriate cycle periods and numbers of cycles for various half lives to analyze homopolymer sequences without using blocking moieties or reversible chain termination.

For example, applying methods disclosed herein, the cycle period may be selected to permit about a 70%, about a 75%, about an 80%, about an 85%, about a 90%, about a 95%, about a 96%, about a 97%, about a 98%, and about a 99% chance of incorporation of two or less nucleotides into the complementary strand. Other cycle periods that may be used in embodiments of the invention include, for example, no more than about 5 half lives, no more than about 4 half lives, no more than about 3 half lives, no more than about 2 half lives, no more than about 1 half life, no more than about 0.9 half lives, no more than about 0.8 half lives, no more than about 0.7 half lives, no more than about 0.6 half lives, no more than about 0.5 half lives, no more than about 0.4 half lives, no more than about 0.3 half lives, and no more than about 0.2 half lives of said incorporation reactions.

The number of times the cycles are repeated can also be determined based on the methods described herein, to permit analysis of different numbers of target polynucleotides of varying lengths. The greater the length of sequence to be analyzed, and the shorter the cycle period used, the greater the number of times cycles will be repeated. Conversely, the greater the slowing down effect of incorporating labeled nucleotides, the longer the half life and the fewer the number of times cycles will be repeated. For example, the number of times may be at least about one, at least about two, at least about three, at least about four, at least about five, at least about six, at least about seven, at least about eight, at least about nine, at least about 10, at least about 30, at least about 50, at least about 100, at least about 500, at least about 1,000, at least about 5,000, at least about 10,000, at least about 50,000, at least about 100,000, and at least about 500,000.

Further examples of combinations of cycle periods and the number of times the cycles are repeated that may be used in certain embodiments of the present invention include a cycle period of no more than about 1 half life, repeated at least about 40 times; a cycle period of no more than about 1 half life, repeated at least about 50 times; a cycle period of no more than about 1 half life, repeated at least about 60 times; a cycle period of no more than about 1 half life, repeated at least about 70 times; a cycle period of no more than about 1 half life, repeated at least about 80 times; a cycle period of no more than about 0.9 half life, repeated at least about 40 times; a cycle period of no more than about 0.9 half lives, repeated at least about 50 times; a cycle period of no more than about 0.9 half lives, repeated at least about 60 times; a cycle period of no more than about 0.9 half lives, repeated at least about 70 times; a cycle period of no more than about 0.9 half lives, repeated at least about 80 times; a cycle period of no more than about 0.8 half lives, repeated at least about 40 times; a cycle period of no more than about 0.8 half lives, repeated at least about 50 times; a cycle period of no more than about 0.8 half lives, repeated at least about 60 times; a cycle period of no more than about 0.8 half lives, repeated at least about 70 times; a cycle period of no more than about 0.8 half lives, repeated at least about 80 times; a cycle period of no more than about 0.7 half lives, repeated at least about 40 times; a cycle period of no more than about 0.7 half lives, repeated at least about 50 times; a cycle period of no more than about 0.7 half lives, repeated at least about 60 times; a cycle period of no more than about 0.7 half lives, repeated at least about 70 times; a cycle period of no more than about 0.7 half lives, repeated at least about 80 times; a cycle period of no more than about 0.6 half lives, repeated at least about 40 times; a cycle period of no more than about 0.6 half lives, repeated at least about 50 times; a cycle period of no more than about 0.6 half lives, repeated at least about 60 times; a cycle period of no more than about 0.6 half lives, repeated at least about 70 times; a cycle period of no more than about 0.6 half lives, repeated at least about 80 times; a cycle period of no more than about 0.5 half lives, repeated at least about 40 times; a cycle period of no more than about 0.5 half lives, repeated at least about 50 times; a cycle period of no more than about 0.5 half lives, repeated at least about 60 times; a cycle period of no more than about 0.5 half lives, repeated at least about 70 times; and a cycle period of no more than about 0.5 half lives, repeated at least about 80 times.

Taking into account various slowing down factors, examples of cycle periods and number repeat cycles that may be used in certain embodiments further include a cycle period of no more than about 0.5 half lives with a slowing down factor of about 2, repeated at least about 90 times; a cycle period of no more than about 0.75 half lives, with a slowing down factor of about 2, repeated at least about 75 times; a cycle period of no more than about 1 half life, with a slowing down factor of about 2, repeated at least about 50 times; a cycle period of no more than about 1.5 half lives with a slowing down factor of about 2 or about 5, repeated at least about 45 times; a cycle period of no more than about 1.75 half lives, with a slowing down factor of about 5, repeated at least about 35 times; a cycle period of no more than about 2 half lives, with a slowing down factor of about 5 or about 10, repeated at least about 35 times; a cycle period of no more than about 2.25 half lives, with a slowing down factor of about 5 or about 10, repeated at least about 30 or at least about 35 times, and a cycle period of about 2.4 half lives, with a slowing down factor of about 5, repeated at least about 30 times.

The cycle period may also be chosen to permit a certain chance of incorporation of a given number of nucleotides in a complementary strand, and the cycle may be repeated a number of times to analyze the sequence of various numbers of target polynucleotides of varying lengths. For example, the cycle period may permit about a 85% chance of incorporation of about two or less nucleotides and may be repeated at least about 40 times; the cycle period may permit about a 85% chance of incorporation of about two or less nucleotides and may be repeated at least about 50 times; the cycle period may permit about a 85% chance of incorporation of about two or less nucleotides and may be repeated at least about 60 times; the cycle period may permit about a 85% chance of incorporation of about two or less nucleotides and may be repeated at least about 70 times; the cycle period may permit about a 85% chance of incorporation of about two or less nucleotides and may be repeated at least about 80 times; the cycle period may permit about a 90% chance of incorporation of about two or less nucleotides and may be repeated at least about 40 times; the cycle period may permit about a 90% chance of incorporation of about two or less nucleotides and may be repeated at least about 50 times; the cycle period may permit about a 90% chance of incorporation of about two or less nucleotides and be repeated at least about 60 times; the cycle period may permit about a 90% chance of incorporation of about two or less nucleotides and be repeated at least about 70 times; the cycle period may permit about a 90% chance of incorporation of about two or less nucleotides and be repeated at least about 80 times; the cycle period may permit about a 95% chance of incorporation of about two or less nucleotides and be repeated at least about 40 times; the cycle period may permit about a 95% chance of incorporation of about two or less nucleotides and be repeated at least about 50 times; the cycle period may permit about a 95% chance of incorporation of about two or less nucleotides and be repeated at least about 60 times; the cycle period may permit about a 95% chance of incorporation of about two or less nucleotides and be repeated at least about 70 times; the cycle period may permit about a 95% chance of incorporation of about two or less nucleotides and be repeated at least about 80 times; the cycle period may permit about a 96% chance of incorporation of about two or less nucleotides and be repeated at least about 40 times; the cycle period may permit about a 96% chance of incorporation of about two or less nucleotides and be repeated at least about 50 times; the cycle period may permit about a 96% chance of incorporation of about two or less nucleotides and be repeated at least about 60 times; the cycle period may permit about a 96% chance of incorporation of about two or less nucleotides and be repeated at least about 70 times; the cycle period may permit about a 96% chance of incorporation of about two or less nucleotides and be repeated at least about 80 times; the cycle period may permit about a 97% chance of incorporation of about two or less nucleotides and be repeated at least about 40 times; the cycle period may permit about a 97% chance of incorporation of about two or less nucleotides and be repeated at least about 50 times; the cycle period may permit about a 97% chance of incorporation of about two or less nucleotides and be repeated at least about 60 times; the cycle period may permit about a 97% chance of incorporation of about two or less nucleotides and be repeated at least about 70 times; the cycle period may permit about a 970% chance of incorporation of about two or less nucleotides and be repeated at least about 80 times; the cycle period may permit about a 98% chance of incorporation of about two or less nucleotides and be repeated at least about 40 times; the cycle period may permit about a 98% chance of incorporation of about two or less nucleotides and be repeated at least about 50 times; the cycle period may permit about a 98% chance of incorporation of about two or less nucleotides and be repeated at least about 60 times; the cycle period may permit about a 98% chance of incorporation of about two or less nucleotides and be repeated at least about 70 times; and the cycle period may permit about a 98% chance of incorporation of about two or less nucleotides and be repeated at least about 80 times.

In addition to the Examples provided below, various cycle periods and number of times the cycles are repeated may be used with various numbers of targets in certain embodiments of the invention. These include, for example, using about 200 target polynucleotides, a period of no more than about 0.6 half lives and repeating at least about 50 times; using about 200 target polynucleotides, a period of no more than about 0.6 half lives and repeating at least about 60 times; using about 200 target polynucleotides, a period of no more than about 0.6 half lives and repeating at least about 70 times; using about 200 target polynucleotides, a period of no more than about 0.8 half lives and repeating at least about 50 times; using about 200 target polynucleotides, a period of no more than about 0.8 half lives and repeating at least about 60 times; using about 200 target polynucleotides, a period of no more than about 0.8 half lives and repeating at least about 70 times; using about 200 target polynucleotides, a period of no more than about 1 half life and repeating at least about 50 times; using about 200 target polynucleotides, a period of no more than about 1 half life and repeating at least about 60 times; and using about 200 target polynucleotides, a period of no more than about 1 half life and repeating at least about 70 times. In any of these embodiments, signal from incorporated nucleotides may be reduced after each or a number of cycles.

D. Address Identification of Randomly Attached Molecules

Another aspect of the present invention features a method of identifying the address of a polynucleotide molecule randomly-bound to a substrate. In such embodiments, the polynucleotide molecule is allowed to attach to any random position on the surface of the substrate, and thereafter its position is detected by allowing an oligonucleotide primer to hybridize to a sufficiently complementary region of the polynucleotide molecule, and/or by allowing extension of the primer by nucleotides complementary to the polynucleotide molecule. In either case, detecting the location of a hybridized and/or incorporated nucleotide permits identification of the address of the randomly-bound polynucleotide molecule. Furthermore, detecting an incorporated nucleotide permits address identification of a polynucleotide molecule that bound as a useful template for the polymerization reaction. That is, it identifies the location of a randomly-bound polynucleotide molecule that attached to the surface in such as way as to be available to the polymerizing agent and capable of directing synthesis of its complementary strand.

In some embodiments, both the primer and the incorporated nucleotide bear labeling moieties, where each labeling moiety produces a distinguishably detectable signal. In these embodiments, cross-correlation of the position of primer signal and the position of the nucleotide signal allows additional accuracy in locating the address, as discussed in more detail below.

E. Single Base Extension of Randomly Attached Molecules

Another aspect of the present invention features a method of analyzing a sequence a polynucleotide molecule randomly-bound to a substrate by single base extension. In such embodiments, the polynucleotide molecule is allowed to attach to any random position on the surface of the substrate, and thereafter synthesis of its complementary strand is allowed in the presence of a polymerizing agent. Detecting incorporation of single nucleotides into the growing complementary strand analyzes the sequence of the randomly-bound polynucleotide molecule.

Some embodiments use a primer bearing a labeling moiety distinguishably detectable from the labeling moiety used on the nucleotides being incorporated into the complementary strand. This can allow detecting spots on the substrate to determine where the polynucleotide molecules are attached, and then monitoring for subsequent nucleotide incorporation events at these locations. In these embodiments, cross-correlation of the primer signal and the nucleotide signal allows additional information about an address of a primer-polynucleotide complex.

For example, the primer may bear a labeling moiety that produces fluorescence of a particular color (e.g. green). One type of nucleotide may bear the same labeling moiety, while one or more other nucleotide types may bear a detectably distinguishable labeling moiety (e.g. red fluorescence). If incorporation of the first type of nucleotide indicates, for example, a wild type sequence, and incorporation of any other nucleotide indicates a variant, detecting different cross-correlated signals from the same primer-polynucleotide complex would indicate the variant (e.g., both green and red). Conversely, detecting only one color after cross-correlating signals would indicate wild type (e.g. green and green). It will be appreciated that other combinations of colors can be used to indicate different sequences. For example, the wild type nucleotides may bear a different labeling moiety, and other nucleotide types may bear the same labeling moiety as the primer or no labeling moiety. In this scenario, cross-correlation of different signals indicates wild type, whereas a variant would be recognized by there being only one color from a primer-polynucleotide complex.

Figure 11:
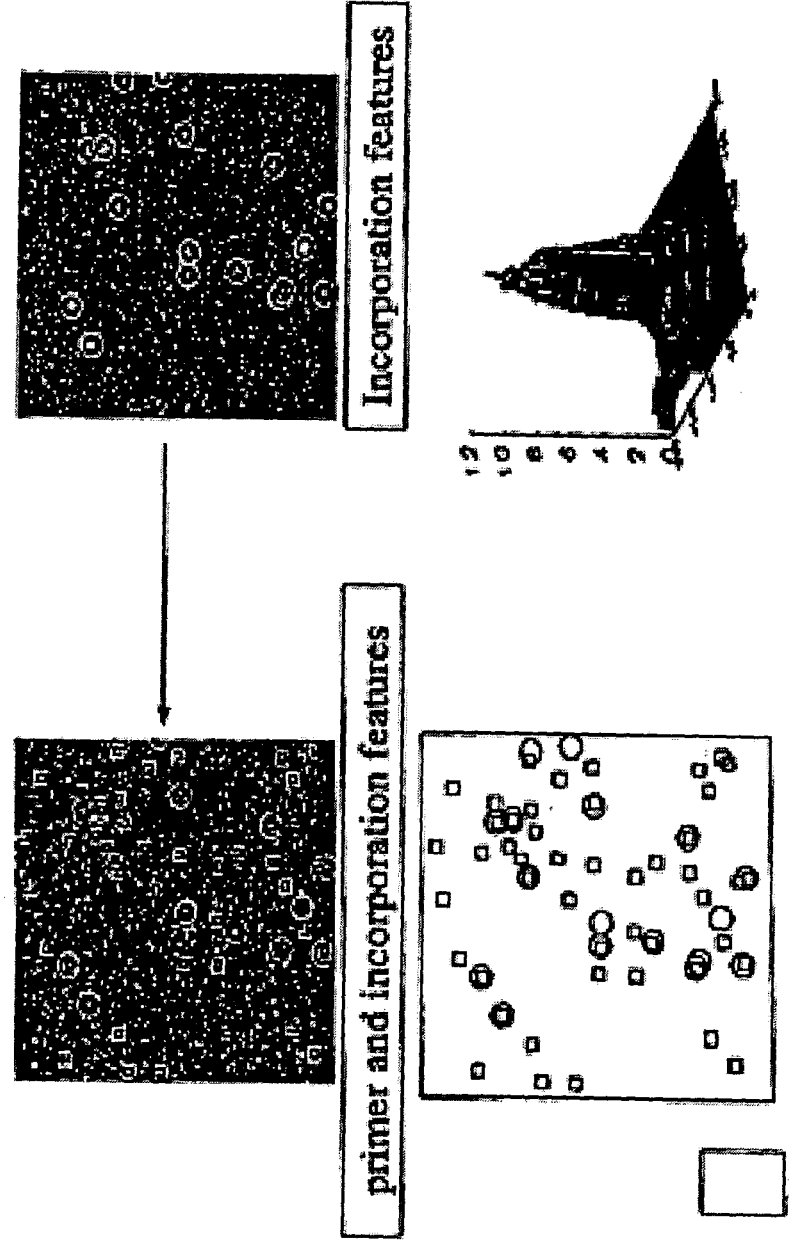
FIG. 11 shows correlation between location of labeled primer and location of incorporation of labeled nucleotides.

FIG. 11, for example, shows correlation between location of labeled primer and location of incorporation of labeled nucleotides. In this embodiment polynucleotide molecules were hybridized to a fluorescently labeled primer and allowed to randomly attach to a surface via steptavidin and biotin with a surface density low enough to resolve single molecules. The primed molecules were detected through their fluorescent tags, and their locations recorded. The identified locations were then monitored for the appearance of fluorescence in subsequent steps. This is, the surface was imaged after allowing incorporation of a single fluorescently-labeled nucleotide. The positions of fluorescence that appeared were compared with the positions detected beforehand. FIG. 11 also shows a correlogram summarizing the pair-wise relationships of the positions of detected molecules in the two fields of view, and will be detailed further in the Examples below.

F. High Density Single Base Extension

Another aspect of the present invention involves analyzing a plurality of polynucleotide molecules bound to a surface of a substrate at high density. In some embodiments, the polynucleotide molecules are randomly localized on the surface. Some embodiments involve allowing polynucleotide molecules to become coupled to the substrate at a certain density, allowing a nucleotide bearing a labeling moiety to become incorporated into its complementary strand, and detecting the incorporation. Various surface chemistries may be used to facilitate forming a dense, random array of primer-polynucleotide complexes, and various detection methods may be used to achieve single molecule resolution of the randomly-bound molecules, as described herein.

In some embodiments, the array features primer-polynucleotide complexes at a density of at least about 1,000 per $cm^2$ at random positions. In some embodiments, the density of complexes on the array can be at least about 2,000 per $cm^2$, at least about 3,000 per $cm^2$, at least about 4,000 per $cm^2$, at least about 5,000 per $cm^2$, at least about 6,000 per $cm^2$, at least about 7,000 per $cm^2$, at least about 8,000 per $cm^2$, at least about 9,000 per $cm^2$, at least about 10,000 per $cm^2$, at least about 20,000 per $cm^2$, at least about 30,000 per $cm^2$, at least about 40,000 per $cm^2$, at least about 50,000 per $cm^2$, at least about 60,000 per $cm^2$, at least about 70,000 per $cm^2$, at least about 80,000 per $cm^2$, at least about 90,000 per $cm^2$, at least about 100,000 per $cm^2$, at least about 200,000 per $cm^2$, at least about 300,000 per $cm^2$, at least about 400,000 per $cm^2$, at least about 500,000 per $cm^2$, at least about 600,000 per $cm^2$, at least about 700,000 per $cm^2$, at least about 800,000 per $cm^2$, at least about 900,000 per $cm^2$, at least about 1 million per $cm^2$, at least about 1.5 million per $cm^2$, at least about 2 million per $cm^2$, at least about 2.5 million per $cm^2$, at least about 3 million per $cm^2$, and at least about 3.5 million per $cm^2$.

G. Sequencing a Given Number of Bases on a Support

In some embodiments, the analysis achieves incorporation of at least a given number of bases on a support. Such embodiments involve permitting localization of a target polynucleotide on a surface of a substrate, providing up to four types of labeled nucleotides, where each of the types comprises a labeling moiety, and allowing incorporation of a given number of the nucleotides into the complementary strand in the presence of a polymerizing agent, detecting the incorporation after incorporation of one or more of the nucleotides. As in other embodiments, the nucleotides may be provided sequentially or simultaneously, and the target may be analyzed in bulk or as a single copy.

H. De Novo Sequencing

In some embodiments, the analysis is used to analyze the sequence of a substantially unknown sequence, i.e., in de novo sequencing. Any of the aspects, embodiments and/or variations of the present invention may be used. Certain embodiments can facilitate de novo sequencing of about 5 bases, about 6 bases, about 7 bases, about 8 bases, about 9 bases, about 10 bases, about 20 bases, about 50 bases, about 100 bases, about 150 bases, about 200 bases, about 250 bases, about 300 bases, about 350 bases, about 400 bases, about 450 bases, about 500 bases, about 550 bases, about 600 bases, about 650 bases, about 700 bases, about 750 bases, about 800 bases, about 850 bases, about 900 bases, about 950 bases, about 1000 bases, about 1100 bases, about 1200 bases, about 1300 bases, about 1400 bases, about 1500 bases, about 1600 bases, about 1700 bases, about 1800 bases, about 1900 bases, about 2000 bases, about 2500 bases, about 3000 bases, about 3500 bases, about 4000 bases, about 4500 bases, about 5000 bases, about 5500 bases, about 6000 bases, about 6500 bases, about 7000 bases, about 7500 bases, about 8000 bases, about 8500 bases, about 9000 bases, about 9500 bases, about 10,000 bases, including at least about 10,000 bases.

I. Re-Sequencing

In some embodiments, the analysis is used to analyze the sequence of a substantially known sequence, i.e., in re-sequencing. Any of the aspects, embodiments and/or variations of the present invention may be used. Certain embodiments can facilitate re-sequencing of about 5 bases, about 6 bases, about 7 bases, about 8 bases, about 9 bases, about 10 bases, about 20 bases, about 50 bases, about 100 bases, about 150 bases, about 200 bases, about 250 bases, about 300 bases, about 350 bases, about 400 bases, about 450 bases, about 500 bases, about 550 bases, about 600 bases, about 650 bases, about 700 bases, about 750 bases, about 800 bases, about 850 bases, about 900 bases, about 950 bases, about 1000 bases, about 1100 bases, about 1200 bases, about 1300 bases, about 1400 bases, about 1500 bases, about 1600 bases, about 1700 bases, about 1800 bases, about 1900 bases, about 2000 bases, about 2500 bases, about 3000 bases, about 3500 bases, about 4000 bases, about 4500 bases, about 5000 bases, about 5500 bases, about 6000 bases, about 6500 bases, about 7000 bases, about 7500 bases, about 8000 bases, about 8500 bases, about 9000 bases, about 9500 bases, about 10,000 bases, about 20,000 bases, about 30,000 bases, about 40,000 bases, about 50,000 bases, about 60,000 bases, about 70,000 bases, about 80,000 bases, about 90,000 bases, about 100,000 bases, about 150,000 bases, about 200,000 bases, about 250,000 bases, about 300,000 bases, about 350,000 bases, about 400,000 bases, about 450,000 bases, and at least about 500,000 bases.

In some embodiments, immobilized template molecule can be used repeatedly, by denaturing the extended molecule, removing the newly-synthesized complementary strand, annealing a new primer, and then repeating the experiment with fresh reagents to sequentially analyze the sequence of the same target polynucleotide. This approach is very sensitive because only a single copy of the template molecule is needed to obtain sequence information. Further, releasing the extension product from the polynucleotide template, e.g., by denaturing, and annealing the template with a different primer, provides the opportunity to re read the same template molecule with different sets of nucleotides (e.g., different combinations of two types of labeled nucleotides and two types of unlabeled nucleotides).

In some embodiments, nucleotides lacking any labeling moiety are provided for a period of time to allow unlabeled nucleotides to "fill in" regions, for example regions that are an already known, until the complementary strand extends to reach unknown regions further downstream. At this point, nucleotides bearing a labeling moiety can be added and analysis begun or continued.

VIII. Applications

The methods and kits of the present invention find numerous applications, as featured below.

A. Polynucleotide Counting and Identification

Another aspect of the present invention involves counting or enumerating a number of copies of a target polynucleotide by synthesizing complementary strands. Such embodiments involve allowing the target polynucleotide to become coupled to a random position on a substrate, detecting incorporation of a sufficient number of nucleotides into the complementary stand to identify the target, and counting the synthesized complementary strands for the identified target. The number of incorporations needed to identify the target polynucleotide may be at least about 15, at least about 16, at least about 17, at least about 18, at least about 19, at least about 20, at least about 21, or at least about 22.

B. DNA Applications

In some embodiments, the target polynucleotide is DNA, for example DNA composing at least 50% of a genome of an organism. Some embodiments further comprise identifying and/or counting a gene sequence of more than one cell, and correlating sequence information from the various cells. Such embodiments find application in medical genetics. Other embodiments compare DNA sequences of normal cells to those of non-normal cells to detect genetic variants. Identification of such variants finds use in diagnostic and/or prognostic applications.

i. Genetic Cancer Research

In some embodiments, the present invention features a method of doing genetic cancer research, where sequence information from a cancer cell is correlated with information from a non-cancer cell or with another cancer cell in a different stage of cancer. In certain embodiments, sequence information may be obtained, for example, for at least about 10 cells, for at least about 20 cells, for at least about 50 cells, for at least about 70 cells, and for at least about 100 cells. Cells in different stages of cancer, for example, include a colon polyp cell vs. a colon cancer cell vs. a colon metastasizing cell from a given patient at various times over the disease course. Cancer cells of other types of cancer may also be used, including, for example a bone cancer, a brain tumor, a breast cancer, an endocrine system cancer, a gastrointestinal cancer, a gynecological cancer, a head and neck cancer, a leukemia, a lung cancer, a lymphoma, a metastases, a myeloma, a pediatric cancer, a penile cancer, a prostate cancer, a sarcoma, a skin cancer, a testicular cancer, a thyroid cancer, and a urinary tract cancer.

In such embodiments, enumeration may determine changes in gene number, indicating, for example that a gene appears three times instead of two times (as in a trisomy) or a gene fails to appear (such as a homozygous deletion). Other types of allelic loss and changes change in diploidy may also be determined, including changes related to, for example, a somatic recombination, a translocation, and/or a rearrangement, as well as a sporadic mutation.

Such embodiments find use in diagnostic and prognostic applications, also featured in the present invention. For example, a homozygous deletion may indicate certain forms of cancer. It will be appreciated by those of skill in the art that other diseases, disorders, and/or conditions may also be identified based on recognized changes in dipoidy. For example, three copies of chromosome 21 genes can indicate trisomy 21, associated with Down syndrome.

ii. Detection of Genetic Variants

Methods of the present invention allow rapid analysis of DNA sequences at the single molecule level, lending themselves to applications relying on detailed analysis of individual sequences. Additional aspects of the present invention include such applications.

For example, certain embodiments provide for SNP detection, by identifying incorporation of a single nucleotide into a complementary strand of a target polynucleotide sequence at the site of a known SNP. Any of the variations, embodiments, and/or aspects of the present invention may be used for such SNP detection. Such methods can also be used to identify other variants due to point mutations, including a substitution, frameshift mutation, an insertion, a deletion, and inversion, a missense mutation, a nonsense mutation, a promoter mutation, a splice site mutation, a sporadic mutation and the like.

Moreover, the invention also features methods of diagnosing a metabolic condition, a pathological condition, a cancer and other disease, disorder or condition (including a response to a drug) by identifying such genetic variants. For example, a known wild type versus a known variant can be distinguished using two detectably distinguishable labeling moieties. Suppose a G at a particular position indicates wild type, while a C at that position indicates a variant of interest. By using G's bearing one detectable labeling moiety, and C's bearing a detectably distinguishable labeling moiety, whether a target polynucleotide exhibits the wild type or variant sequence can readily be determined by the methods of the present invention.

Certain embodiments provide for detection of additional genetic variants, by identifying incorporation of more than one nucleotide into a complementary strand of a target polynucleotide sequence, either at substantially known regions of variation or at substantially unknown regions. Any of the variations, embodiments, and aspects of the present invention may be used for such detection. Comparison of sequences from more than one individual allows identification of genetic variants, including substitutions, frameshift mutations, insertions, deletions, inversions, missense mutations, nonsense mutations, promoter mutations, splice site mutations, sporadic mutations, a duplication, variable number tandem repeats, short tandem repeat polymorphisms, and the like.

Moreover, the invention also provides methods of diagnosing a metabolic condition, a pathological condition, a cancer, and/or other disease, disorder or condition (including a response to a drug) by identifying such genetic variants. For example, in some embodiments, the identified nucleotide variant indicates adenomatous polyposis *coli*, adult polycystic kidney disease, α1-antitrypsin deficiency, cystic fibrosis, duchenne muscular dystrophy, familial hypercholesterolemia, fragile X syndrome, hemochromatosis, hemophilia A, hereditary nonpolyposis colorectal cancer, Huntington disease, Marfan syndrome, myotonic dystrophy, neurofibromatosis type 1, osteogenesis imperfecta, phenylketonuria, retinoblastoma, sickle cell disease, Tay-Sachs disease, or thalassemia, as well as cleft lip, club foot, congenital heart defects, neural tube defects, pyloric stenosis, alcoholism, Alzheimer disease, bipolar affective disorder, cancer, diabetes type I, diabetes type II, heart disease, stroke, or schizophrenia.

C. RNA Applications

In some embodiments, the target polynucleotide is RNA, and/or cDNA copies corresponding to RNA. In some embodiments, the RNA includes one or more types of RNA, including, for example, mRNA, tRNA, rRNA, and snRNA. In some embodiments, the RNA comprises RNA transcripts.

Some embodiments use a primer that hybridizes to the target polynucleotide whose complementary strand is to be synthesized. In some of those embodiments, the primer used comprises a polyT region and a region of at least two degenerate nucleotides. This facilitates identification and/or counting of random mRNA sequences in eukaryotic cells, as the polyT can hybridize to the polyA region of the mRNA and the degenerate nucleotides can hybridize to corresponding random sequences. Such primers also avoid sequencing the polyA tail itself.

In some embodiments, the RNA comprises RNA molecules from a cell, from an organelle, and/or from a microorganism. The number of RNA molecules may be about 100, about 200, about 300, about 400, about 500, about 600, about 700, about 800, about 900, about 1,000, about 2,000, about 3,000, about 4,000, about 5000, about 6,000, about 7,000, about 8,000, about 9,000, about 10,000, up to an including all of the RNA molecules in the cell, organelle, and/or microorganism. Some embodiments comprise identifying and counting RNA molecules from more than one cell, organelle, and/or microorganism. A histogram of the copy numbers of various types of RNA molecules identified can be constructed for different cells, organelles and/or microorganisms, and used to compile transcriptional patterns of RNA complements for each analyzed cell. The different cells, organelles, and/or microorganisms may be in different states, e.g. a diseased cell vs. a normal cell; or at different stages of development, e.g. a totipotent cell vs. a pluripotent cell vs. a differentiated cell; or subjected to different stimuli, e.g. a bacterial cell vs. a bacterial cell exposed to an antibiotic. In some embodiments, the methods can detect any statistically significant difference in copy numbers between cells, organelles, and/or microorganisms.

i. Identifying Unknown RNA Molecules

Such sequence information finds use in a number of applications featured by the present invention. For example, an aspect of the present invention involves identifying unknown RNA molecules. In some embodiments, the methods facilitate detection of RNA molecules in a cell limited only by Poisson statistics. In such embodiments, for example, determining copy number of RNA molecules can identify untranslated sequences and/or hitherto unknown RNA molecules that are ordinarily present in low or very low copy numbers, such as about one, about two, about three, about four, about five, about 6, about 7, about 8, about 9, about 10, about 11, about 12, about 15, about 20, and about 25.

ii. Annotating Genomes

The invention also features an approach to annotating genomes based on counting and identifying RNA transcripts. The identified transcripts indicate, for example, how sequenced genes are actually transcribed and/or expressed. By comparing the analyzed sequence of an identified transcript to one or more predicted expressed sequences, the prediction can be confirmed, modified, or refuted, providing a means to annotate genomes.

iii. Tissue Engineering

Another application featured in the present invention involves methods of tissue engineering. Such embodiment provide for analyzing a plurality of RNA molecules of a cell at different stages of differentiation towards a particular tissue type, compiling information about transcriptional patterns of the RNA molecules (e.g. copy number and identity), and causing a target cell to feature a similar transcription pattern, thereby engineering a cell-type of the tissue.

The differentiated state may be that of a heart cell, a pancreatic cell, a muscle cell, a bone cell, an epidermal cell, a skin cell, a blood cell, a nerve cell, a mammary gland cell, a cell of the olfactory epithelium, a cell of the auditory epithelium, a cell of the optic epithelium, an endodermal cell, a lung cell, an alveoli cell, a cell of the respiratory epithelium, an intestinal cell, an absorptive cell, a goblet cell, a Paneth cell, an enteroendocrine cell, a liver cell, a mesodermal cell, a blood vessel cell, and an endothelial cell.

iv. Determining Phylogenic Relationships

Still another feature of the present invention involves methods of determining phylogenic relationships of various species. Such embodiments provide for compiling transcriptional patterns of cells from different species and analyzing the relationships amongst homologous transcripts. Such information finds use in determining evolutionary relationships amongst species.

v. Determining Cellular Responses to Stimuli

Another feature of the present invention involves a method of determining a microorganism's response to various stimuli, for example, response when exposed to a drug or subjected to other treatment, such as being deprived of certain metabolites. In such embodiments, transcriptional patterns of a cell of the microorganism, for example a bacteria cell, can be compared before and after administration of the drug or other treatment.

vi. Identifying Alternative Splice Sites

Certain embodiments provide for detection of alternative splice sites, by identifying incorporation of a nucleotide into a complementary strand of a target polynucleotide sequence, either at known regions of a splice site or at unknown regions. Any of the variations, embodiments, and/or aspects of the present invention may be used for such detection. Comparison of sequences from more than one RNA molecule allows identification of alternative splice sites. In some embodiments, a primer can be allowed to hybridize to a region on the target RNA molecule within one or more nucleotides downstream of the region of interest, i.e, the expected slice site. Incorporation of nucleotides can then be allowed to proceed, extending the primer towards the region of interest, at least far enough to identify the concatenated exon.

Moreover, the invention also provides methods of diagnosing cancer and other diseases, disorders and/or conditions, including, for example, sickle cell anemia, by identifying such alterations in splicing. For example, in some embodiments, the identified nucleotide variant indicates adenomatous polyposis *coli*, adult polycystic kidney disease, α1-antitrypsin deficiency, cystic fibrosis, duchenne muscular dystrophy, familial hypercholesterolemia, fragile X syndrome, hemochromatosis, hemophilia A, hereditary nonpolyposis colorectal cancer, Huntington disease, Marfan syndrome, myotonic dystrophy, neurofibromatosis type 1, osteogenesis imperfecta, phenylketonuria, retinoblastoma, sickle cell disease, Tay-Sachs disease, or thalassemia, as well as cleft lip, club foot, congenital heart defects, neural tube defects, pyloric stenosis, alcoholism, Alzheimer disease, bipolar affective disorder, cancer, diabetes type I, diabetes type II, heart disease, stroke, or schizophrenia.

Many modifications and variations of this invention can be made without departing from its spirit and scope. The specific embodiments described below are for illustration only and are not intended to limit the invention in any way. All publications, figures, patents and patent applications cited herein are hereby expressly incorporated by reference for all purposes to the same extent as if each was so individually denoted.

EXAMPLES

Example 1

Basic Materials and Methods
1. Materials and Reaction Reagents
   (1) Solutions and Buffers
   RCA: H2O:NH4OH:H2O2 (6:4:1) boiling for an hour.
   PEI: PolyEthylenImine (Sigma P-3143) (positive charged)
   PALL: Poly(allylamine hydrochloride) (Sigma 283223)
   PACr: Poly(acrylic acid, sodium salt) (Sigma 416045) (negative charged)
   EDC: 9.6 mg/ml; 50 mM (×10) 1-{3-(Dimethylamino) propyl]-3-ethylcarbodiimide,
   hydrochloride), Activator for the BLCPA (Sigma-161462)
   BLCPA: EZ-Link Biotin LC-PEO-Amine (Pierce 21347) Stock solution 50 mM in MES 10 mM (21 mg/ml) (×10)
   Streptavidin plus-1 mg/ml in Tris. PROzyme, Code: SA20 (×10)
   Buffers:
   MES (N-morpholinoethanesulfonic acid) PH 5.5 1M (100×)
   TRIS 10 mM
   TRIS-MgCl2 10 mM Tris, 100 mM MgCl2 (×1)
   TKMC (10 mM Tris.HCl, 10 mM KCl, 10 mM MgCl2, 5 mM Ca Cl2, pH 7.0)
   EcoPol: 10 mM Tris.HCl, 5 mM MgCl2, 7.5 mM DTT pH@25° C.; buffer come with the polymerase at (×10)
   (2) Other Materials and Reagents
   Nucleotides: dTTP, dGTP, dATP, and dCTP-Cy3 at 10 μM concentration
   Polymerase:a) Klenow Polymerase I (5 units/μl), New England BioLabs Cat. 210S
   b) Klenow-exo, New England BioLabs Cat. 212S
   c) TAQ
   d) Sequenase
   Hybridization Chamber: Sigma H-1409
   Polynucleotide templates and primers:

```
                                              (SEQ ID NO: 1)
7.: Biotin-5'-tcagtcatca gtcatcagtc
atcagtcatc agtcatcagt catcagtcat cagtcatcag
tcatcagtca tcagtcatca gtcatcACAC GGAGGTTCTA-3'

(SEQ ID NO:2)
Primer p7G: 5'-TAGAACCTCCGTGT-3'; the
primer can be labeled with Cy5 or Cy3.

(SEQ ID NO:3)
Mu50: Biotin 5'-ctccagcgtgttttatctctgcgagca
taatgcctgcgtcatccgccagc 3'

(SEQ ID NO:4)
Cy5 labeled primer (PMu50Gy5):
Cy5 5'-gctggcggatgac-3'

(SEQ ID NO:5)
7.7A-Biotin-5'-
tttGcttcttAttctttGcttcttAttctttGcttcttAttctttGcttc
ttAttctttGcttcttAttctttGcttcttAttcttACAGGGA GGTTCT
A-3'

(SEQ ID NO:6)
6.A6CG: Biotin-5'-ccAtttttttGccccccAtttttttGc
ccccAtttttttGccccccAtttttttGccccccAtttttttACACGGAGGTT
CTA-3',
```

2. Substrate Treatment and Template Attachment

A fused silica microscope slide (1 mm thick, 25×75 mm size, Esco Cat. R130110) was used to attach DNA templates. The slides was first cleaned with the RCA method as described above and in WO 01/32930. Multilayer of polyallylamine/polyAcrylic were absorbed to the slide. An EZ link connector was then attached to the slides as follows: the slide was dried, scratched with diamond pencil, and then covered with a hybridization chamber. 120 μl of a mixture of 1:1:8 EDC: BLCPA: MES (50 mM EDC, 50 mM BLCPA, 10 mM MES) was applied to each slide. Following incubation for 20 minutes, 120 μl of Streptavidin Plus diluted to 0.1 mg/ml was added to the slide. After 20 min of incubation, the slide was washed with 200 μl of Tris 10 mM.

Preparation of 10 pM Oligo: the 7G oligonucleotide template (SEQ ID NO:1) was pre-hybridized with Cy5-labeled primer (SEQ ID NO:2) (in stock at 7 µM) in TRIS-MgCl2 buffer. The treated slide was examined for contamination with the TIR microscope. 200 µl of the oligonucleotide/primer mixture was applied to each slide. Following incubation for 10 min, the slide was washed with 200 µl ml of Tris 10 mM.

Addition of nucleotides and polymerase: nucleotides dTTP, dATP, dGTP, and Cy3-dCTP each of 20-100 nM were mixed in the ECOPOL buffer. 1 µl Klenow 210S from stock solution (kept in −20° C.) was added to 200 microliters of the nucleotide mixture. 120 µl of the mixture was then added on each slide. After incubation for 0 to 30 min (for different experiments), the slide was examined with the TIR microscope. Unless otherwise noted, all reactions were performed at room temperature, while the reaction reagents were kept at 4° C. or −20° C. The primer/oligonucleotide hybridization reaction was carried out with a thermocycler machine.

Single molecule resolution was achieve by using very low concentration of the polynucleotide template which ensured that only one template molecule is attached to a distinct spot on the slide. Single molecule attachment to a distinct is also confirmed by the observation of single bleaching pattern of the attached fluorophores. In the reaction described above, a concentration of about 10 pM of a 80-mer oligonucleotide template was used for immobilizing to the slide. The space between different DNA molecules attached to the surface slide was measured at a few micrometers.

Imaging with Single Molecule Resolution

As illustrated in FIG. 1a, incorporation of a single nucleotide molecule into the complementary strand of a single target polynucleotide molecule can be detected and imaged according to the present invention. FIG. 1a illustrates two different target polynucleotides analyzed in parallel on the surface of a substrate. Incorporation of, for example, an labeled adenine nucleotide (A*) into a complementary stand of one of the target polynucleotides is visualized on the surface, as indicated by the spot shown in the top view. Later, incorporation of, for example, a labeled thymine nucleotide (T*) into the complementary strand of a different target polynucleotide can be seen as a spot on a different position in the field of view, corresponding to a different location on the surface of the substrate. If nucleotides incorporate into both stands, for example two A*'s, two spots at corresponding positions can be detected, indicating incorporation into the complementary strands of the two individual target polynucleotides.

Figure 1B:
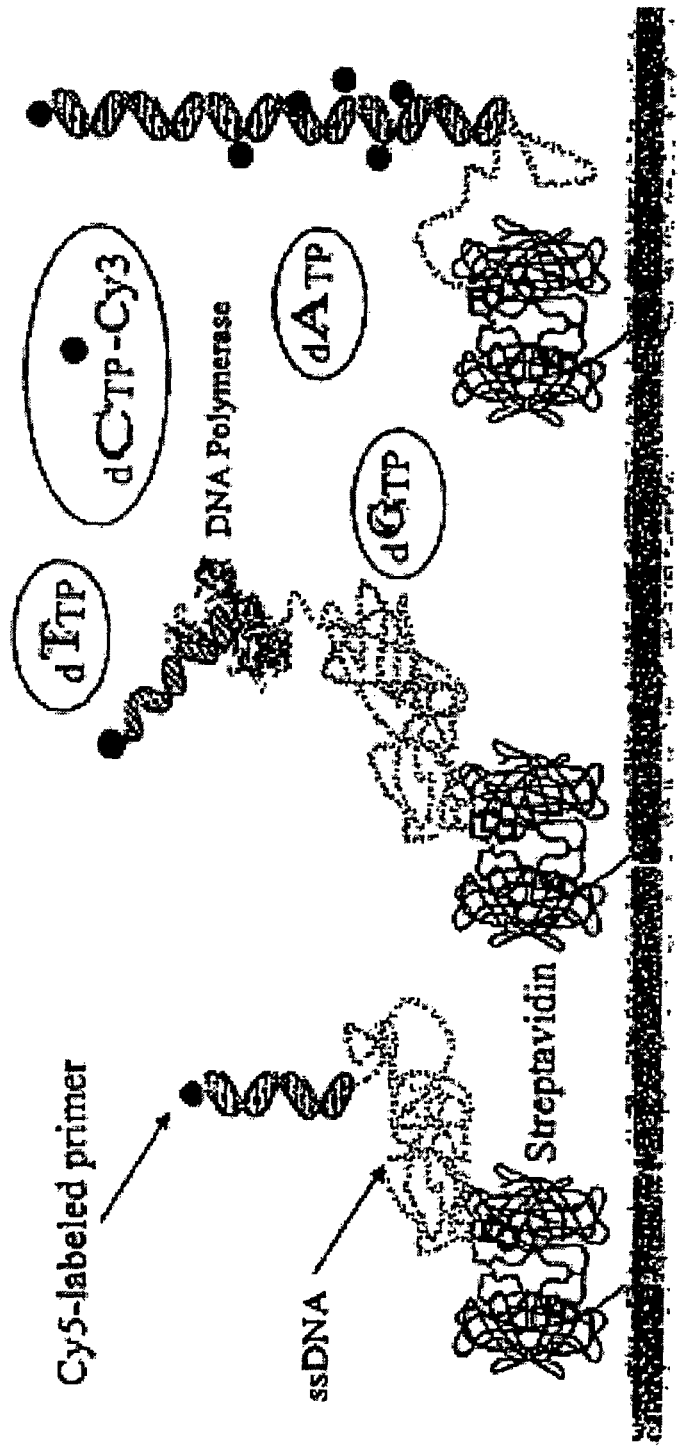
FIG. 1b shows a more detailed cartoon of the primed target polynucleotide.

As illustrated in FIG. 1b, the single stranded oligonucleotide template (SEQ ID NO:1) primed with a Cy5 labeled primer sequence (SEQ ID NO:2) was immobilized at a single molecule resolution to the surface of a silica slide using a biotin-streptavidin bond. The surface is coated with polymers on which biotin (EZ link) is tethered. The oligonucleotide template, with a biotin molecule attached to one of its ends, was able to attach to the streptavidin-linked surface. The slide surface was negatively charged which helps to repeal unbound nucleotides The DNA is specifically attached to the surface by its 5' side, meaning that the primer—which the polymerase extends—is away from the surface.

The template and incorporation of labeled nucleotides were visualized by fluorescence imaging. Location of the oligonucleotide was monitored by fluorescence from the Cy5 labeled primer (SEQ ID NO:2). Incorporation of nucleotides was detected because the nucleotides were labeled with Cy3. After incorporation, the incorporated labels were illuminated. Illumination of Cy3 was at a wavelength of 532 nm. Following a typical time of a few seconds of continued illumination, the signals were bleached, typically in a single step.

Figure 2:
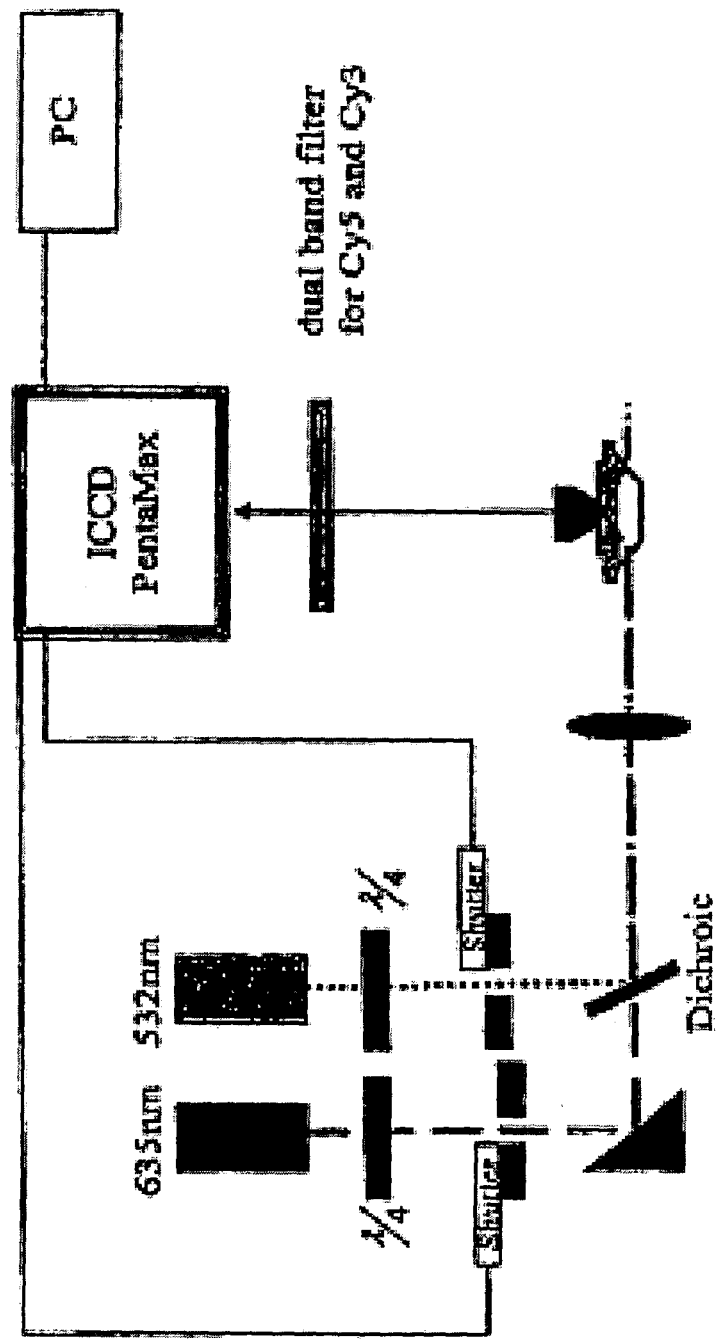
FIG. 2 shows schematically the optical setup of a detection system for total internal reflection microscopy.

As shown in FIG. 2, imaging of fluorescent signals with single molecule resolution was enabled with surface illumination by total internal reflection (TIR). Ishijima et al. (Cell 92:161-71, 1998) showed that it is possible to observe the fluorescence of single molecules immobilized to a surface in a wet environment even when there are free molecules in the solution. Here, the TIR was facilitated by a dove prism coupling of the laser beam to the silica slide surface. An upright microscope with an immersion oil objective was used to image the surface with an intensified CCD (PentaMax). A filter set (Chroma) was used to reject the illumination frequency and let the fluorescence frequency to reach the ICCD.

Example 2

Test for Specific Attachment of Template Molecules to Substrate Surface

Figure 3:
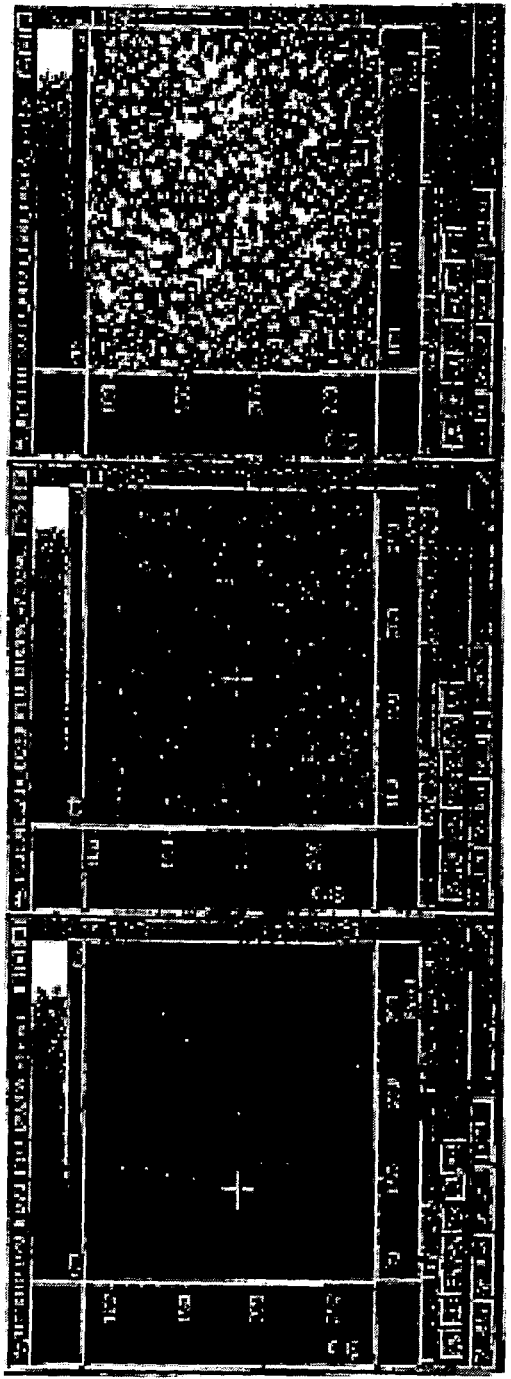
FIG. 3 shows results which indicate streptavidin can be used to immobilize a polynucleotide template in an exemplified embodiment.

This experiment was performed to determine whether the polynucleotide templates are attached to the surface as desired. FIG. 3 shows that streptavidin is required for binding the template to the surface and hence detection of incorporated fluorescence signal. The left panel shows that there is no fluorescence signal when only streptavidin-attached surface but no fluorescent labels were present. The middle panel shows that there is no incorporated fluorescent signals when no streptavidin was present on the surface to attach biotin-labeled oligonucleotide template, even though Cy5-labeled primer was present. The right panel shows that detection of incorporated fluorescent signal when the streptavidin-attached surface, labeled primers, and biotin-labeled oligonucleotide template were present.

Example 3

Figure 5:
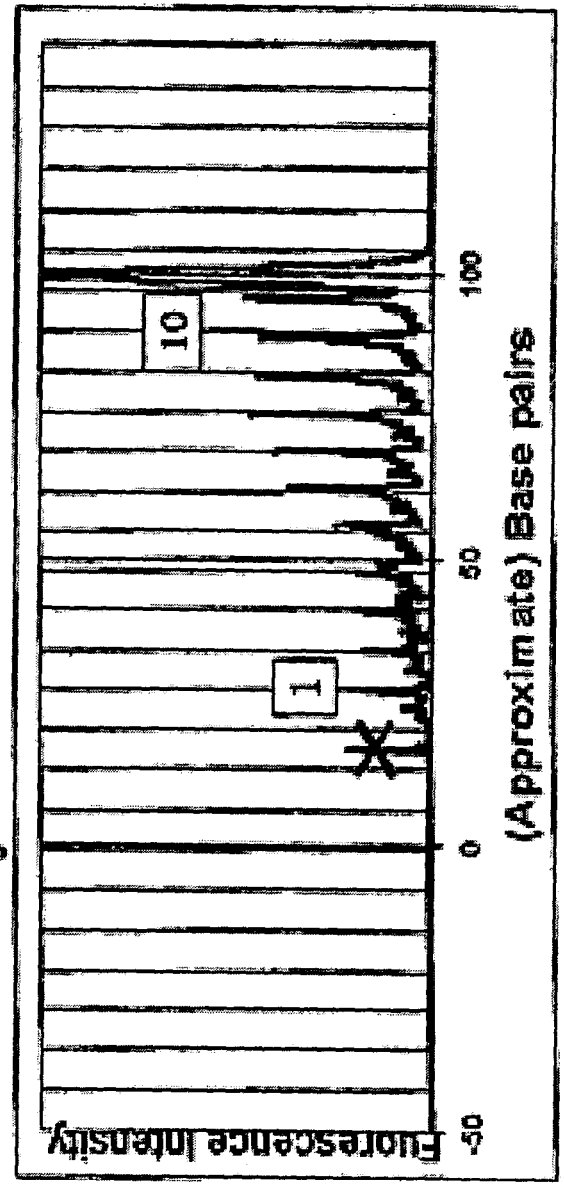
FIG. 5 shows incorporation of multiple labeled nucleotides in a bulk experiment in solution, using biotin-labeled 7G oligonucleotide template (SEQ ID NO:1) and p7G primer (SEQ ID NO:2).

Determining Processivity of DNA Polymerase in the Presence of Labeled Nucleotides To determine whether the DNA polymerase accurately incorporates labeled nucleotides into the template, a bulk extension experiment was performed in a test tube rather than on the surface of a substrate. As shown in FIG. 5, the results indicate that the polymerase incorporate all the labeled nucleotides into the correct positions. In this experiment, incorporation of dCTP-Cy3 and a polymerization terminator, ddCTP, were detected using a 7G DNA template (a DNA strand having a G residue every 7 bases; SEQ ID NO:1). The annealed primer was extended in the presence of non-labeled dATP, dGTP, dTTP, Cy3-labeled dCTP, and ddCTP. The ratio of Cy3-dCTP and ddCTP was 3:1. The reaction products were separated on a gel, fluorescence excited, and the signals detected, using an automatic sequencer ABI-377. The results reveal that incorporation of Cy3-dCTP did not interfere with further extension of the primer along the 7G oligomer template.

FIG. 5 shows fluorescence intensity from primer extension products of various lengths which were terminated by incorporation of ddCTP at the different G residues in the 7G oligomer template (SEQ ID NO:1). The first band is the end of the gel and should not be counted as it is in the very beginning of the gel. The full length of the template is 100 residues. The first band (marked "1" in the graph) corresponds to extension products which were terminated by incorporation of non-labeled ddCTP at the second G residue (position 27) and has incorporated Cy3-dCTP at the first G residue (position 20). Similarly, the tenth band (marked "10" in the graph) represents extension products which were terminated by incorporation of non-labeled ddCTP at the 10th G residue (position 90) and has incorporated Cy3-dCTP at the previous G residue (i.e., positions 20, 27, 34, 41, 48, 55, 62, 69, 76, and 83). The results showed a nice agreement between the expected positions for Cy3 incorporation in the polynucleotide template and the positions of the fluorescence intensity bands.

Example 4

Detection of Single Nucleotide Incorporation by TIR

Total internal reflection (TIR) fluorescence microscopy allows detection of real-time incorporation of labeled nucleotide into single immobilized polynucleotide template. This illumination method reduce the background from the sample by illuminating only a thin layer (e.g., in the order of 150 nm) near the surface. Even in the presence of free dyes in the solution (up to 50 nM), single molecules can be observed. Using TIR, we visualized single molecules of labeled nucleotide bound to DNA in the presence of up to 50 nM free dye in solution. Though this concentration is low compared to the concentration needed for a high rate of incorporation of nucleotides by the DNA polymerase, it was sufficient for its operation.

Optical Setup

The lasers source is shown in FIG. 2, the light sources (e.g., laser) are coupled to the surface by prism. The surface is imaged by a regular 1.3 NA microscope objective onto an Intensified CCD (Pentamax). A fluorescent filter in the optical way block the laser intensity and allow the fluorescent signals from the dye molecules pass through(Chroma filters). Optionally, the camera and the shutters for the lasers are controlled by the computer.

Illumination

Figure 6:
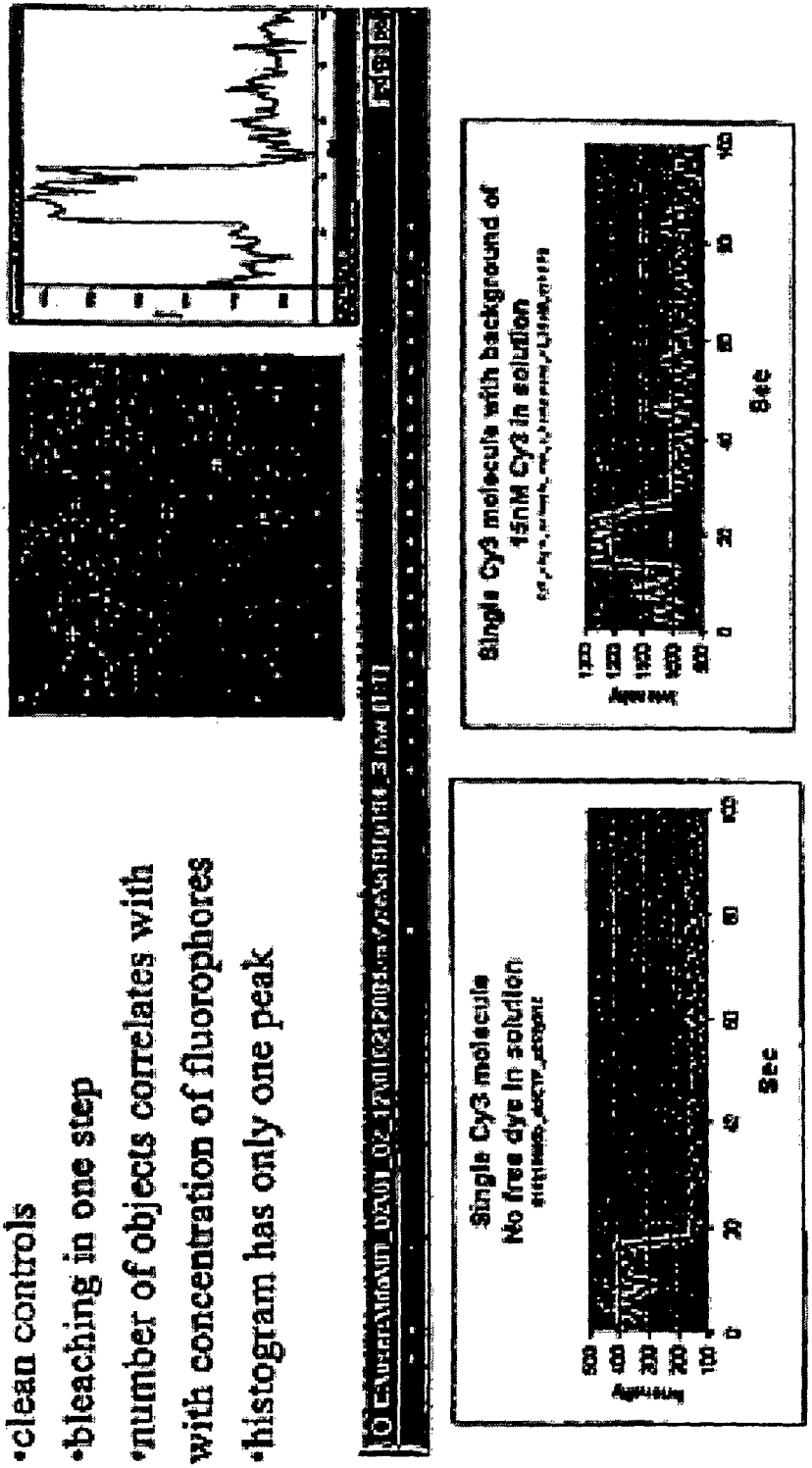
FIG. 6 shows low background signal from free nucleotides in solution and detection of signals from incorporated nucleotides.

As shown in FIG. 6, TIR illumination of polynucleotide-attached slide produced a low background and allowed detection of signals only from immobilized labels. The refraction index of the fused silica glass and the oil beneath the surface is about 1.46. The refraction index of the liquid above the glass is about 1.33 to 1.35. At the interface of the glass and the water the illumination ray was refracted. If the illumination is very shallow, 70-75 degree from the surface orthogonal, the refracted light was reflected back and not continued in the liquid phase as the critical angel for total internal reflection is about 65-67 degrees (TetaCitical=sin−1(n1/n2)).

The illumination process, called evanescent illumination, leaves a decay field near the interface which illuminates only about 150 nm into the liquid phase. Fluorophores dyes can be excited by this field. So only the dyes which are near the surface will emit. Furthermore, free labeled nucleotide molecules in the solution will move around due to Brownian motion. The fast movement of these free molecules produces only a smear signal because the integration time is in the order of hundred millisecond. Thus, the total internal reflection illumination leads to a low back ground from the free molecules, and only signals from the immobilized dyes are detected.

Detection of Single Molecules

FIG. 6 shows detection of signals from single Cy3 molecule with no free dye in solution versus signals from single Cy3 molecule with background of 15 nM Cy3 in solution. Fluorescence image from incorporation of Cy3 labeled nucleotide is shown in the upper panels. The signals tend to bleach in a single step, see the upper graph. When there are free labeled nucleotides in the solution (15 nM free dye), the background signal is stronger (lower right panel) than the background signal in the absence of free labeled nucleotides in the solution. But the signal from the incorporated single molecule can still be detected. The ability to detect single molecule in the presence of free dye enables one to follow incorporation of nucleotide into an immobilized DNA template in real time.

The upper left panel of FIG. 6 showed typical images of single molecules (see the bright spots). When the intensity of a spot is traced in real time (upper right panel), one can see that it appears (incorporation event or sticking to the surface event) and disappears (bleaching or detaching event). The same results are also illustrated in the middle long thin panel of FIG. 6. This panel shows successive images of a small area around the spot that was being traced. The fluorescent signal appeared and disappeared after every few seconds (every frame is a second exposure).

Example 5

Determining Nucleotide Incorporation Based on Correlation of Fluorescence Spots

A correlation was observed between the position of the immobilized DNA template on the surface (indicated by the fluorescently labeled primer) and the incorporation of nucleotide to the surface. In FIG. 4, image of the immobilized DNA which was hybridized to the Cy5 labeled primer was shown in the upper two panels (the middle panel is a magnified image of a small area in the left panel). The small dots in the image represent likely positions of the DNA templates immobilized on the surface. The fluorescence signals were then bleached out by a long radiation (about 1 minute) at 635 nm with a 10 mW laser diode. Subsequently, the polymerase and the nucleotides (including the Cy3-labeled dCTP) were added, and the mixture incubated at room temperature for about an hour. After washing, a second image of the surface was taken. This time a new set of fluorescence-labeled points appeared (see lower left two panels). The results indicate that the two sets of fluorescently-labeled points are correlated (see right panel). It is noted that the significant overlap (about 40%) between DNA primer location (Cy5) and dCTP Incorporation location (Cy3) cannot be a random result. Under the concentrations of labeled DNA primers used in the experiment, the probability for this correlation to occur randomly calculated to be about 10-50. Rather, the correlation is due to incorporation of the Cy3 labeled nucleotides into the immobilized, Cy5 labeled primer.

Figure 7:
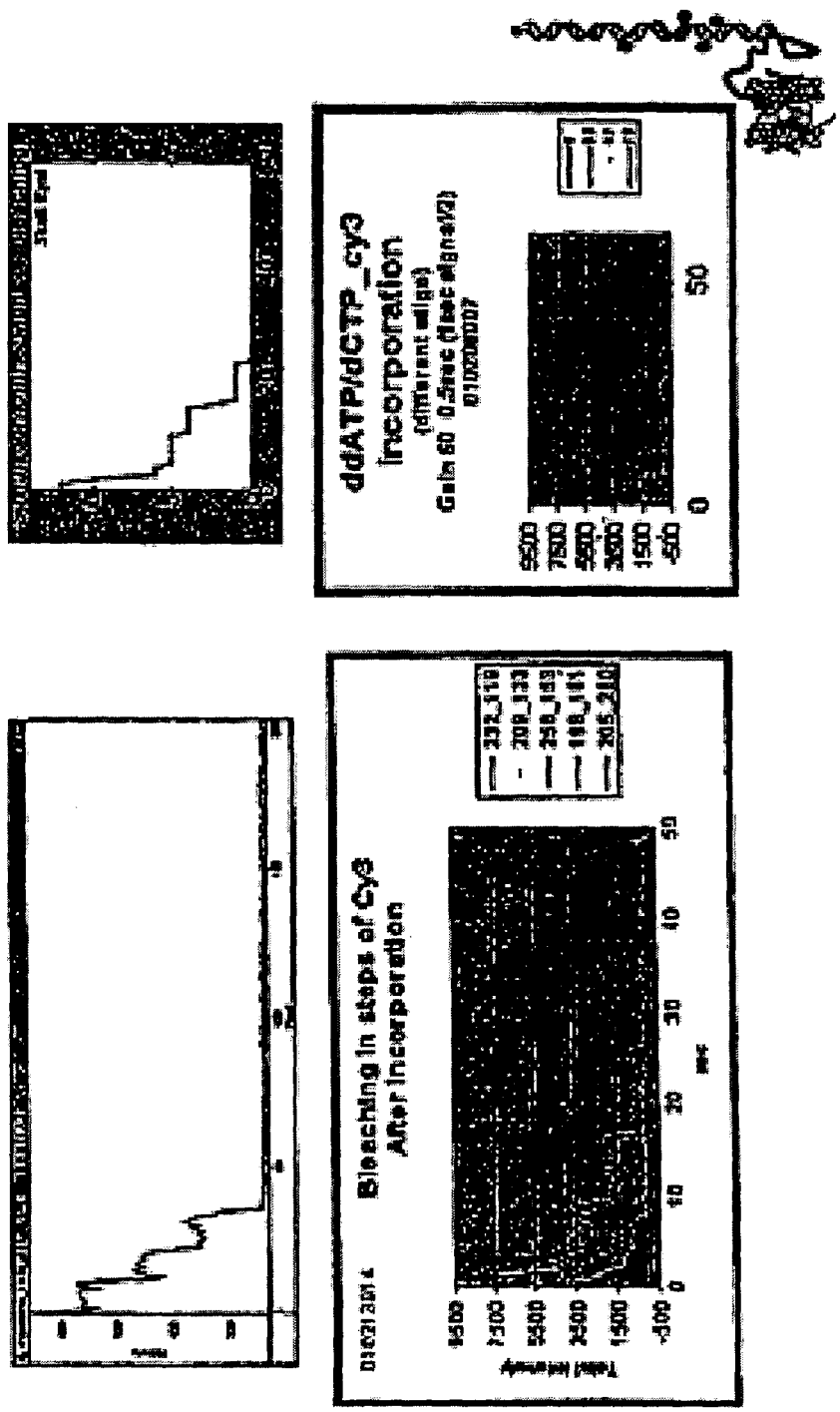
FIG. 7 shows results from experiments and simulation of multiple bleaching.

Incorporation of labeled nucleotide into the immobilized template is also demonstrated by the multi-incorporation data shown in FIG. 7. When the intensity of the spots in FIG. 4 were measured, a multistep bleaching is observed (FIG. 7, upper left panel). Simulation of the multiple bleaching is shown in the upper right panel. The results are what should be expected if few molecules are located in the same place up to the optical resolution. This indicates that the polymerase can incorporate a few labeled nucleotides into the same DNA template. In a control experiment, ddATP, dCTP-Cy3 and dGTP were used to extend Cy5-labeled primer PMu50Cy5, Cy5 5'-gctggcggatgac-3' (SEQ ID NO:4) along the Mu50 oligonucleotide template (SEQ ID NO 3). This allows only one Cy3-labeled nucleotide to be incorporated into the primer because the first codon in the template sequence after the primer is CGT. Incorporation of ddATP immediately after the incorporation of dCTP-Cy3 terminates the elongation. As shown in the lower right panel, there is no multibleaching.

It is noted that because the concentration of the DNA template on the surface was so low, it is unlikely that more than one copy of the DNA template were present on each spot. Further, multiple bleaching is not common when the polymerase was not present (data not shown). In particular, there is no correlation between primer location and fluorescence signal from the surface when the polymerase was not present (see, e.g., FIG. 13, middle panel).

Example 6

Dynamics of Nucleotide Incorporation

Figure 8:
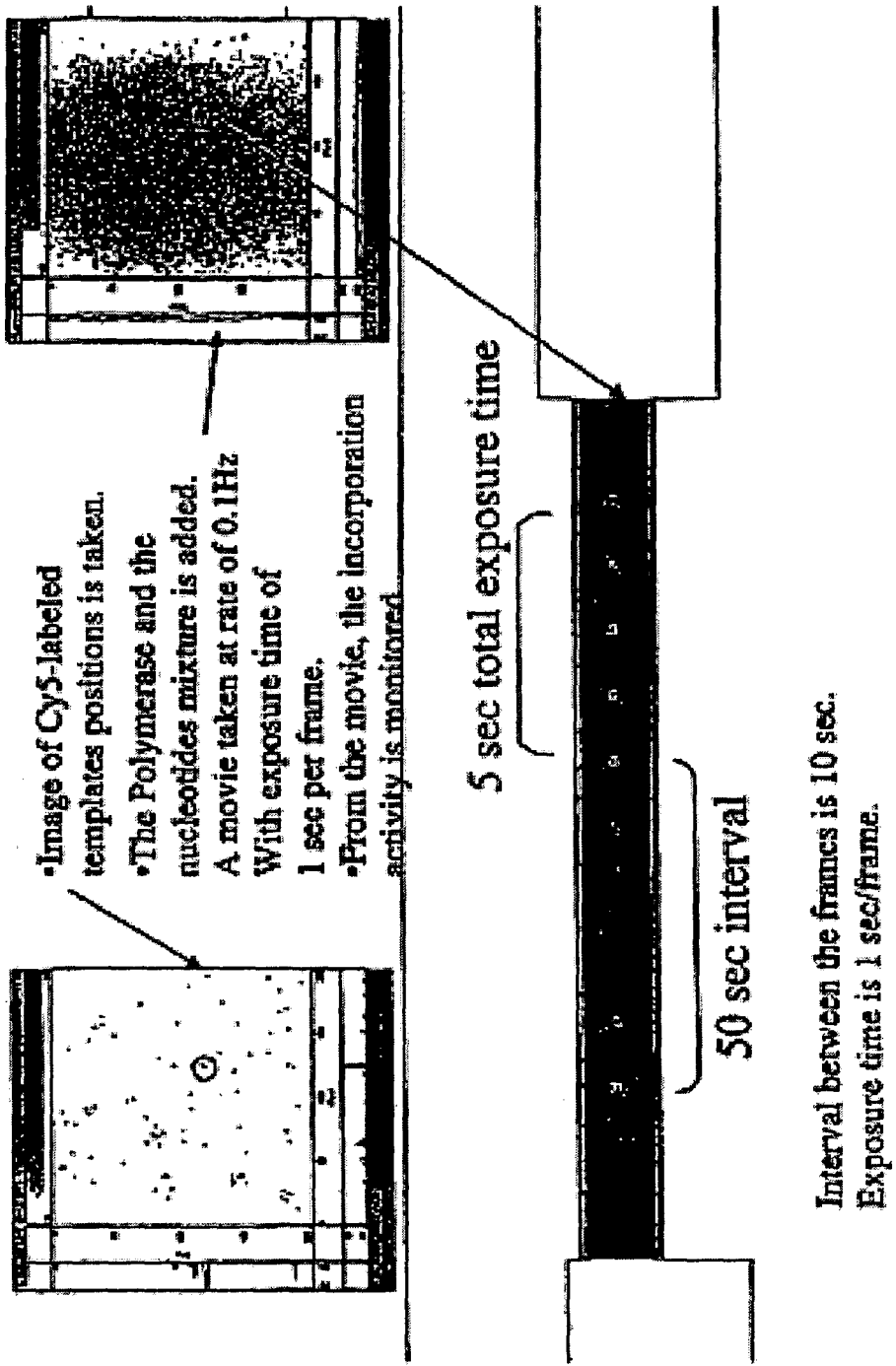
FIG. 8 shows dynamics of incorporation of labeled nucleotides into the immobilized primer.

FIG. 8 shows a time course of incorporation events during the DNA polymerase reaction. In this experiment, the DNA template and Cy5-labeled primer complex was immobilized to the substrate surface as described above, and its position was imaged. The DNA Polymerase was then added along with the nucleotides of which one was labeled with Cy3.

As indicated in the figure, the substrate was imaged every 10 sec, with a 1 sec exposure. Every spot with immobilized DNA template (as indicated by the labeled primer) was monitored as a function of time. A series of small images of these spots were placed along a strip resulting in a movie showing the "activities" at each point.

Figure 9:
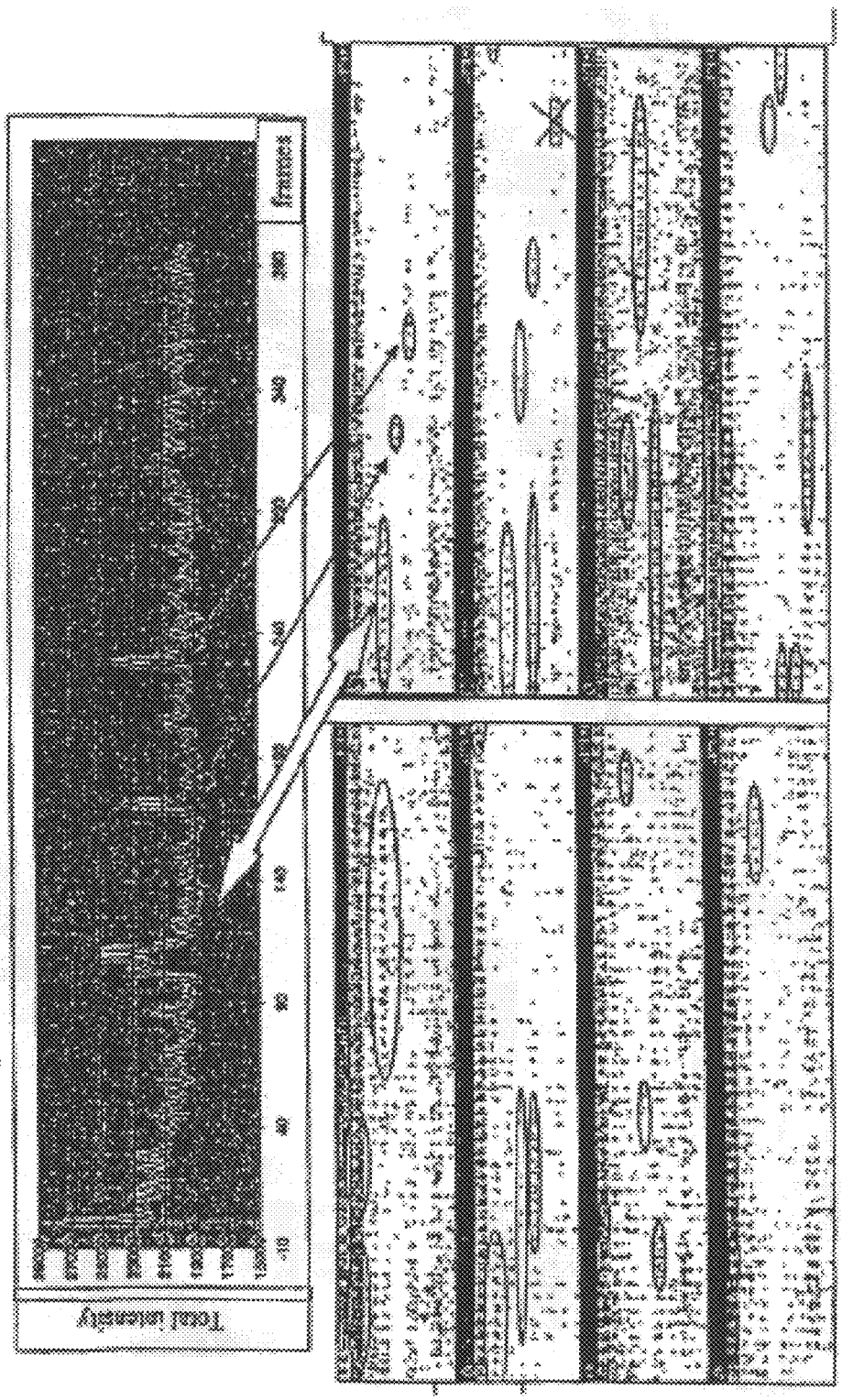
FIG. 9 shows multiple incorporation events of labeled nucleotides over a period of time.

Repeated incorporation of nucleotide into the DNA template was shown in FIG. 9. Using more dyes will enable us to read the sequence of the DNA directly in an asynchronous manner FIG. 9 shows the dynamic incorporation events at 8 different spots. The digital information recorded in these movies indicate that repeated incorporation events occurred at various time points. The data also demonstrated the feasibility of monitoring primer extension activities on single DNA molecules.

Figure 10:
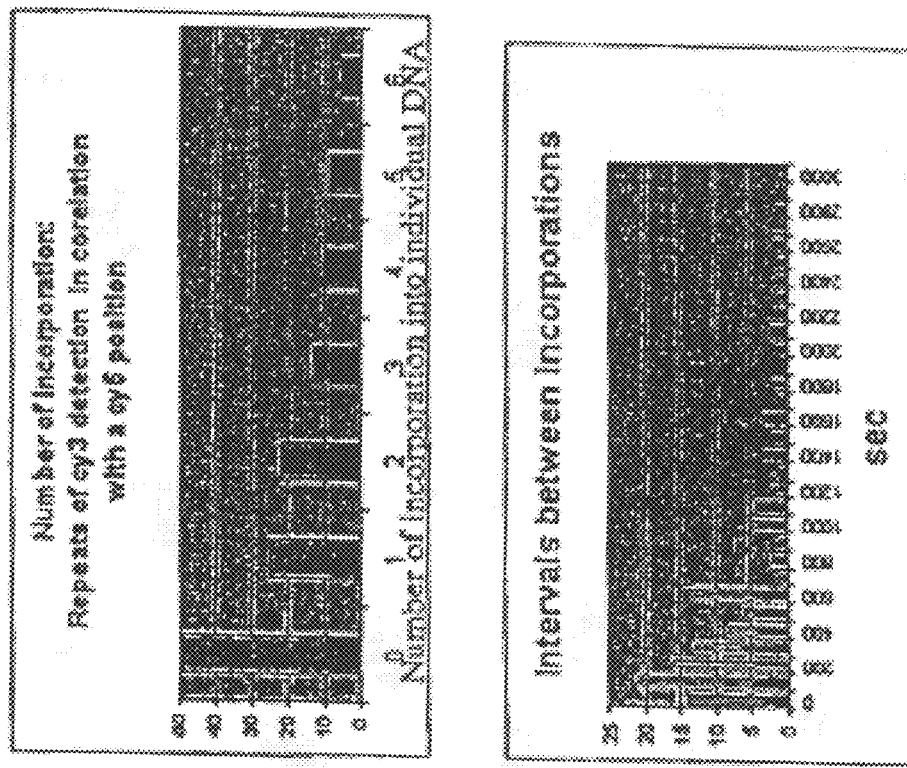
FIG. 10 shows statistics of incorporation of labeled nucleotides over a period of time.

FIG. 10 shows a histogram of the number of incorporation events on single spots and a histogram of the time between incorporation events. From the histograms one can see that a few nucleotides were incorporated into single DNA molecules. The low numbers of events in which more then three nucleotides were incorporated indicate that there is some mechanism that prevents high number of incorporation into the DNA under the experimental conditions. The reason could be that photo-damage to the DNA in the surrounding area of the illuminated dye might produce toxic radicals. Changing the reaction conditions and reagents could increase the numbers of incorporated nucleotides dramatically.

Example 7

Base-by-base Sequence Analysis

This experiment was performed to confirm selectivity of the polymerase and to illustrate feasibility of determining the sequence of a polynucleotide template with base-by-base scheme.

First, fidelity of the polymerase in incorporation was confirmed by analyzing correlation between location of immobilized primer and location of nucleotide incorporation with a correlation graph FIG. 11 shows correlation between primer location and polymerase activity location. The position of each point was determined with a sub pixel resolution. Images for the primer location and the incorporation position were taken first. If there is a correlation between the two, there is a pick in the correlation graph. Otherwise no pick was observed. As shown in the figure, the two images correlate with each other.

Figure 12:
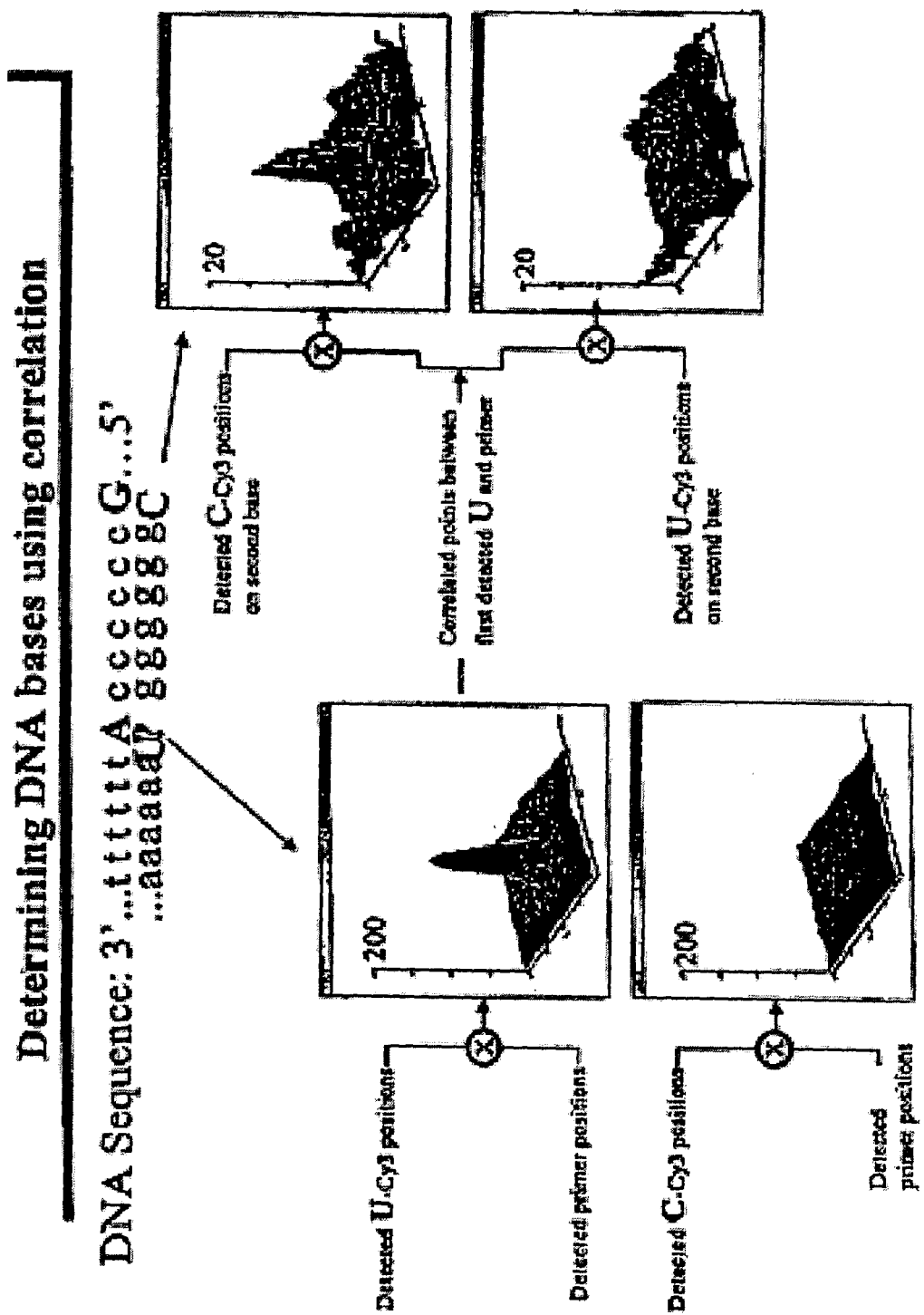
FIG. 12 shows correlation graphs for incorporation of two labeled nucleotides, using a 6TA6GC oligonucleotide template (SEQ ID NO:6) and a p7G primer (SEQ ID NO:2). Partial sequences of the template, 5'-GcccccAtttttt-3' (SEQ ID NO:7), and the extended product, 5'-aaaaaaUgggggggC (SEQ ID NO:8), are also shown in the Figure.

Results demonstrating base-by-base analysis of the sequence of a immobilized template at single molecule resolution is shown in FIG. 12. The data indicated that at least two bases of the template were determined by flowing in and out reagents along with different types of labeled nucleotides (e.g., dCTP-Cy3, dUTP-Cy3, etc.). Here, a 6TA6GC oligo-nucleotide template (SEQ ID NO:6) was immobilized to the fused silica slide. A Cy3-labeled p7G primer (SEQ ID NO:2) was annealed to the template. As illustrated in the Figure, the primer was first extended up to the A residue with non-labeled dATP nucleotides. Then, dUTP-Cy3 nucleotide was incorporated and imaged. Images taken at this time show high correlation (see the upper left correlation graph). After bleaching the dyes, dCTP-Cy3 was applied to the sample. Images taken at this time show low correlation (see the lower left correlation graph). Thereafter, non-labeled dGTP was added to fill the CCCCC gap till the G residue in the sequence. At this time, incorporation of a dCTP-Cy3 nucleotide was examined again. This time there was a correlation between the dCTP-cy3 positions and the primer positions in general, and in particular there was a correlation with the position of the incorporated dUTP in the first incorporation cycle. Thereafter, dUTP-Cy3 was added. Correlation was found between the labeled primer position and signal from dUPT-Cy3, but no correlation was found between the new dUPT-Cy3 positions and the position that has incorporated dUTP in the first incorporation cycle (lower right graph). The interpretation is that not all the primers were extended in the first dUTP incorporation cycle, that those which did not get extended could incorporate dUTP in the second incorporation cycle, and that those which did incorporate dUTP in the first cycle could not incorporate dUTP again in the second cycle. The results indicate that on those spots which have incorporated the first U residue there were also incorporations of a C but not a U residue. Thus, identity of a second base can be determined with the experimental scheme, although the yield for the second base (upper right graph) was not as good as for the first base (upper left graph).

In a control experiment, after filling in with A residues, dCTP-Cy3 (wrong nucleotide for the first base) was added. Correlation between Cy3-labeled primer position and C-Cy3 was low (data not shown). In another control, after filling in the string of A residues, the U residue, G residues, and U-Cy3 (wrong residue for the second base) was added. The correlation observed from the results in this experiment was low (at the noise level; data not shown). Using different oligonucleotide templates, the experiment scheme was repeated for successive incorporations of other combinations of two or more nucleotides (data not shown). The results confirmed correct incorporation of the first labeled nucleotide with high signal-to-noise ratio and subsequent incorporations of more nucleotides with a relatively lower signal-to-noise ratio. Taken together, these data indicate that the observed results (e.g., as shown in FIG. 12) are not due to artifacts, but rather demonstrate efficacy of base-by-base analysis of the experimental scheme.

Example 8

Two Color Incorporation: Fluorescence Resonance Energy Transfer

Figure 13:
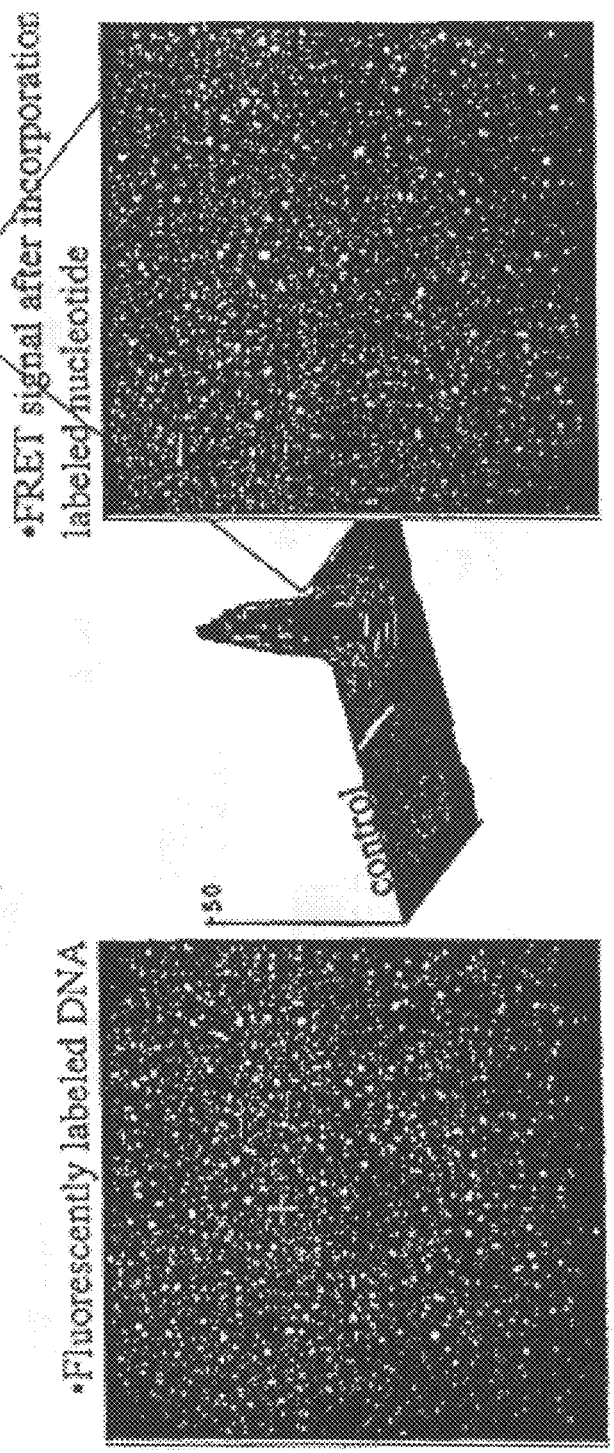
FIG. 13 shows detection of a single DNA molecule using fluorescence resonance energy transfer (FRET), when two different labels are incorporated into the same primer extension product. The polynucleotide template used here is the 7G7A oligonucleotide (SEQ ID NO:5), but only part of the sequence, 5'-AttctttGcttcttAttctttGcttcttAttctttG-3' (SEQ ID NO:9), is shown in the Figure.

This experiment demonstrate incorporation of two different fluorescent labels into the same immobilized polynucleotide template through detection of fluorescence resonance energy transfer (FRET). In this experiment, two fluorescent labels were used (Cy5 and Cy3), and FRET from dUTP-Cy3 (donor) to dCTP-Cy5 (acceptor) was examined at the single molecule level as shown in FIG. 13.

Image of the DNA template with the labeled primer is shown in the left panel. Detection of FRET after incorporation of the two labels is provided in the right image. Correlation between the template location and the incorporation signals is shown in the middle graph. As indicated, there is a high correlation between the template location and the incorporated nucleotide location. A control experiment was performed in which no polymerase is present. Results from the control experiment produced a low correlation between the template location and location of labeled nucleotides. FRET experiment provides particularly high signal to noise ratio as there is almost no signal from nonspecific incorporation of dyes to the surface.

Figure 14:
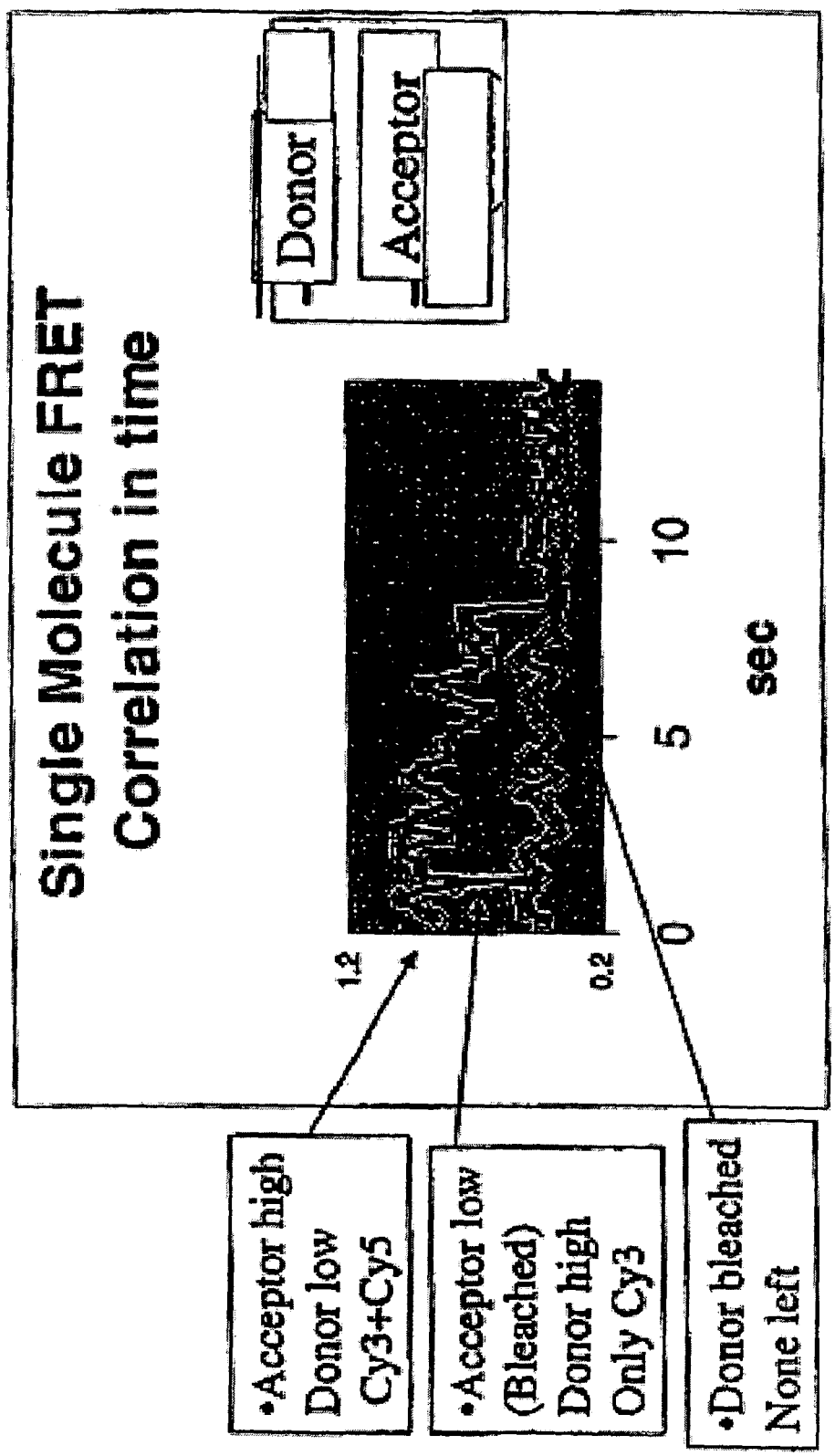
FIG. 14 shows correlation of single molecule FRET signals over a period of time.
Figure 15:
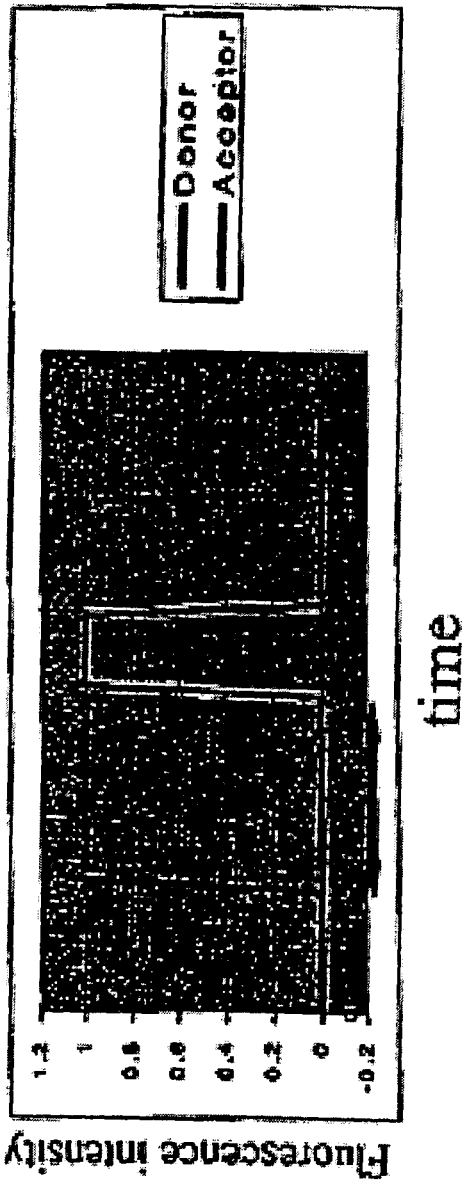
FIG. 15 shows the expected signals from an experiment in which two colors, donor and acceptor, are incorporated sequentially. Partial sequences of the template, 5'-GccccccAtttttt-3' (SEQ ID NO:7), and the extended product, 5'-aaaaaaUgggggggC (SEQ ID NO:8), are also shown in the Figure.

When the two labels were incorporated into a primer at close vicinity, i.e., at a few nanometers apart, a single molecule FRET signal was detected (FIG. 14). To detect the FRET signal, the optic setup was altered. A image splitter was added so that the same area was imaged twice(Optical Insights LTD, micro imager device). In one channel, a fluorescence filter detected only the donor (cy3) fluorescence. In the other channel, a filter for the acceptor (Cy5) was placed. With this setup individual spots were examined after incorporation FIG. 15 further indicates that the FRET detection scheme allows measurement of incorporation rate with a nice signal to noise ratio.

Example 9

Figure 24:
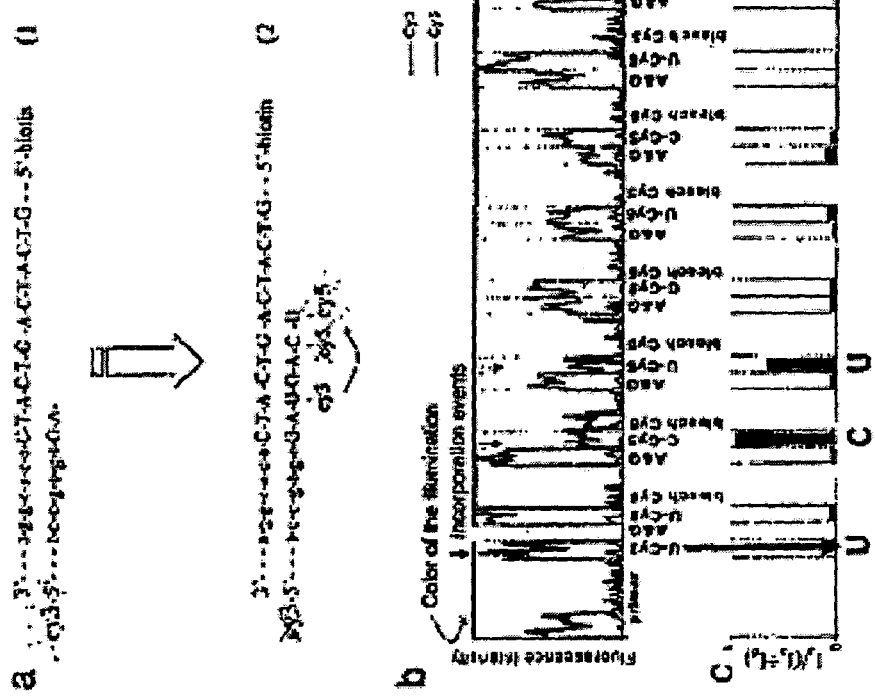
FIG. 24 illustrates one type of choking using Cy5-labeled nucleotides in consecutive incorporations (SEQ ID NOS 11, 12 & 13, respectively in order of appearance).

FIG. 24 illustrates choking using Cy5-labeled nucleotides. The reaction conditions used were as follows:

Detection and Data Analysis. An upright microscope (BH-2, Olympus, Melville, N.Y.) equipped with total internal reflection (TIR) illumination served as a platform for the experiments. Two laser beams, 635 (Coherent, Santa Clara, Calif.) and 532 nm (Brimrose, Baltimore), with nominal powers of 8 and 10 mW, respectively, were circularly polarized by quarter-wave plates and undergo TIR in a dove prism (Edmund Scientific, Barrington, N.J.). The prism was optically coupled to the fused silica bottom (Esco, Oak Ridge, N.J.) of a hybridization chamber (Sigma) so that evanescent waves illuminated up to 150 nm above the surface of the fused silica. An objective (DPlanApo, 100 UV 1.3 oil, Olympus) collected the fluorescence signal through the top plastic cover of the chamber, which was deflected by the objective to 0.40:m from the silica surface. An image splitter (Optical Insights, Santa Fe, N. Mex.) directed the light through two bandpass filters (630dcxr, HQ585/80, HQ690/60; Chroma Technology, Brattleboro, Vt.) to an intensified charge-coupled device (I-PentaMAX; Roper Scientific, Trenton, N.J.), which recorded adjacent images of a 120- ×60-:m section of the surface in two colors. Typically, eight exposures of 0.5 sec each were taken of each field of view to compensate for possible intermittency in the fluorophore emission. Custom IDL software was modified to analyze the locations and intensities of fluorescence objects in the intensified charge-coupled device pictures.

Sample Preparation

The target DNA was composed of a DNA primer, [Cy3•5N•tagaacctccgtgt-3N](SEQ ID NO: 2) which was annealed to template 3 [3N-atcttggaggcacaCTACTGACT-(ACTGACT)I1-5N-biotin] (SEQ ID NO: 1) (all oligonucleotides were synthesized by Operon, Technologies, Alameda, Calif.). This template was designed so that labeled nucleotides would be incorporated in adjacent positions. Surface chemistry based on polyelectrolytes and biotin-streptavidin bonding was used to anchor the DNA molecules to the fused silica surface of the hybridization chamber and to minimize nonspecific binding of the nucleotides to the surface. Slides were sonicated in 2% MICRO-90 soap (Cole-Parmer, Vernon Hills, Ill.) for 20 min and then cleaned by immersion in boiling RCA solution (6:4:1 high-purity H2O/30% NH4OH/30% v H2O2) for 1 h. They were then immersed alternately in polyallylamine (positively charged) and polyacrylic acid (negatively charged; both from Aldrich) at 2 mg/ml and pH 8 for 10 min each and washed intensively with distilled water in between. The carboxyl groups of the last polyacrylic acid layer served to prevent the negatively charged labeled nucleotide from binding to the surface of the sample. In addition, these functional groups were used for further attachment of a layer of biotin. The slides were incubated with 5 mM biotinamine reagent (Biotin-EZ-Link, Pierce) for 10 min in the presence of 1-[3-(dimethylamino)propyl]-3-ethylcarbodiimide hydrochloride (EDC, Sigma) in MES buffer, followed by incubation with Streptavidin Plus (Prozyme, San Leandro, Calif.) at 0.1 mg/ml for 15 min in Tris buffer. The biotinylated DNA templates were deposited onto the streptavidin-coated chamber surface at 10 pM for 10 min in Tris buffer that contained 100 mM MgCl2. For incorporations, the reaction solution contained Klenow fragment Exo-minus polymerase (New England Biolabs) at 10 nM (100 units/ml) in the reaction buffer (EcoPol buffer, New England Biolabs) and a nucleotide triphosphate. dATP, dGTP, dTTP and dCTP from Roche Diagnostics, dCTP-Cy3, dUTP-Cy3, and dUTP-Cy5 from Amersham Pharmacia, dCTP-Cy5, dATP-Cy3, dGTP-Cy3, dATP-Cy5, and dGTP-Cy5 from Perkin-Elmer, and dCTP-Alexa647 from Molecular Probes were used at 0.2 :M for the Cy3 -labeled and 0.5 :M for the Cy5-labeled and unlabeled nucleotides. Incubation times were 6-15 min, with the longer incubation time at the later stages of the experiment. To reduce bleaching of the fluorescence dyes, an oxygen scavenging system was used during all green illumination periods, with the exception of the bleaching of the primer tag.

Reagent Exchange Sequence for Single-Pair FRET Sequencing

The positions of the anchored Cy3-primed DNA were recorded, and then the tags were bleached by the green laser illumination (FIG. 24a). dUTP-Cy3 and polymerase were introduced and washed out. An image of the surface was then analyzed for incorporated U-Cy3. If there were none, the process was repeated with dCTP-Cy3. If there was still no incorporation, incubation was repeated with unlabeled dATP and dGTP and then cycled again from the beginning until the first fluorescently labeled base had been incorporated. The Cy3 dye of this incorporated nucleotide was kept unbleached. Next, a mix of dATP, dGTP, and polymerase was incubated to ensure that the primer was extended until the next A or G of the template. At this point, the reagents were switched to Cy5-labeled nucleotides or Alexa-647, a Cy5 analogue (Molecular Probes). The incorporation and observation process was repeated, except that each observation with green illumination was followed by an observation with red illumination to photobleach any incorporated Cy5 fluorophores. After bleaching the acceptor, the mix of dATP, dGTP, and polymerase was again incubated, washed out, and the sample observed briefly with green illumination to record the recovery of the donor.

FIG. 24(a) is a schematic illustrating extension of template 3, which includes adjacent incorporations of labeled dCTP and dUTP. FIG. 245(b) shows a sequence trace from an experiment with template 3. The label at each column indicates the last nucleotide to be incubated, and successful incorporation events are marked with an arrow. FIG. 24(c) shows the FRET efficiency as a function of the experimental epoch.

Yield was reduced to about 10% for the second incorporation, indicating that, in most cases, the polymerase was halted or choked and elongation was prevented due to the bulkiness of the adjacent label. Use of dyes larger than Cy5 can be used to reduce yield further, halting polymerizing agent in all cases due to the increased bulkiness of an incorporated label.

Example 10

An exemplified scheme of coating a substrate with PEM for immobilizing polynucleotide is as follows:

Carboxylic acid groups are negatively charged at pH 7, and are a common target for covalent bond formation. Terminating the surface with carboxylic acid groups generates a surface which is both strongly negatively-charged and chemically reactive. In particular, amines can link to carboxylic acid groups to form amide bonds, a reaction catalyzed, for example, by carbodiimides. Thus, a molecule with biotin at one end, a hydrophilic spacer, and an amine at the other end can be used to terminate the surface with biotin.

An avidin molecule is capable of binding up to four biotin molecules. This means that avidin, and its derivative Streptavidin, is capable of converting a biotin-terminated surface to a surface capable of capturing biotin. Streptavidin, which carries a slight negative charge, can be used then to attach the polynucleotide templates to be analyzed to the surface by using a biotinylated primer. A buffer with a high concentration of multivalent salt can be used in order to screen the repulsion of the negatively charged surface for the negatively-charged DNA.

To coat the polyelectrolyte multilayer, the glass cover slips can be first cleaned with high purity $H_2O$ ($H_2O$ deionized to 18.3 MOhm-cm and filtered to 0.2 μm) and a RCA Solution (6:4:1 mixture of HIGH PURITY $H_2O$, (30% $NH_4OH$), and (30% $H_2O_2$)). The cover slips can be then sonicated in 2% Micr 90 detergent for 20 minutes. After rinsing thoroughly with high purity $H_2O$, the cover slips can be stirred in gently boiling RCA solution for at least 1 hour, and rinsed again with high purity $H_2O$.

After cleaning, the glass cover slips can be submerged in PAII solution (Poly(allylamine) (PAII, +): 2 mg/ml in high purity $H_2O$, adjusted to pH 7.0) and agitated for at least 10 minutes. The cover slips can then be removed from PAII and washed with BP $H_2O$ by submerging in BP $H_2O$ with agitation, repeated for at least three times. The treatment can continue by agitation in a PAcr solution (Poly(acrylic acid) (PAcr, −): 2 mg/ml in HIGH PURITY $H_2O$, adjusted to pH 7.0) for at least 10 minutes and washed with HIGH PURITY $H_2O$. The treatment steps can then be repeated once.

After PEM coating, the PEM coated glass can be incubated with an EDC/BLCPA solution for 30 minutes. The EDC/BLCPA solution can be prepared by mixing equal amounts of 50 mM EDC solution (in MES buffer) and 50 mM BLCPA (in MES buffer) and diluting to 5 mM in MES buffer. The glass can then be rinsed with 10 mM Tris-NaCl and incubated with 0.1 mg/ml streptavidin solution for 1 hour. After washing with 10 mM Tris-NaCl, the glass can be incubated with a solution containing the polynucleotide template (for example, $10^{-7}$ M in Tris 100 mM $MgCl_2$) for 30 minutes. The glass can be again rinsed thoroughly with 10 mM Tris-NaCl.

For in-situ attachment, the microfluidic substrate can be bonded to the glass cover slip by HCl-assisted bonding. Essentially, the chips can be first washed with a surfactant (e.g., first with HIGH PURITY $H_2O$, then in 0.1% Tween 20, then rinse again with HIGH PURITY $H_2O$). The washed microfluidic chips can then be put on the glass cover slips with a few microliters of dilute HCl (e.g., 1% HCl in HIGH PURITY $H_2O$), followed by baking at 37° C. for 1-2 hours. Such treatment can enhance the bond strength to glass (e.g., >20 psi pressure) without increasing nonspecific adsorption.

Following HCl treatment, PEM formation, biotinylation, and streptavidinylation, template attachment can be performed using essentially the same reagents and methods as described above for ex-situ attachment, except that the solutions can be injected through the channels by pressure instead of just being aliquoted onto the substrate surface.

Example 11

Figure 19A:
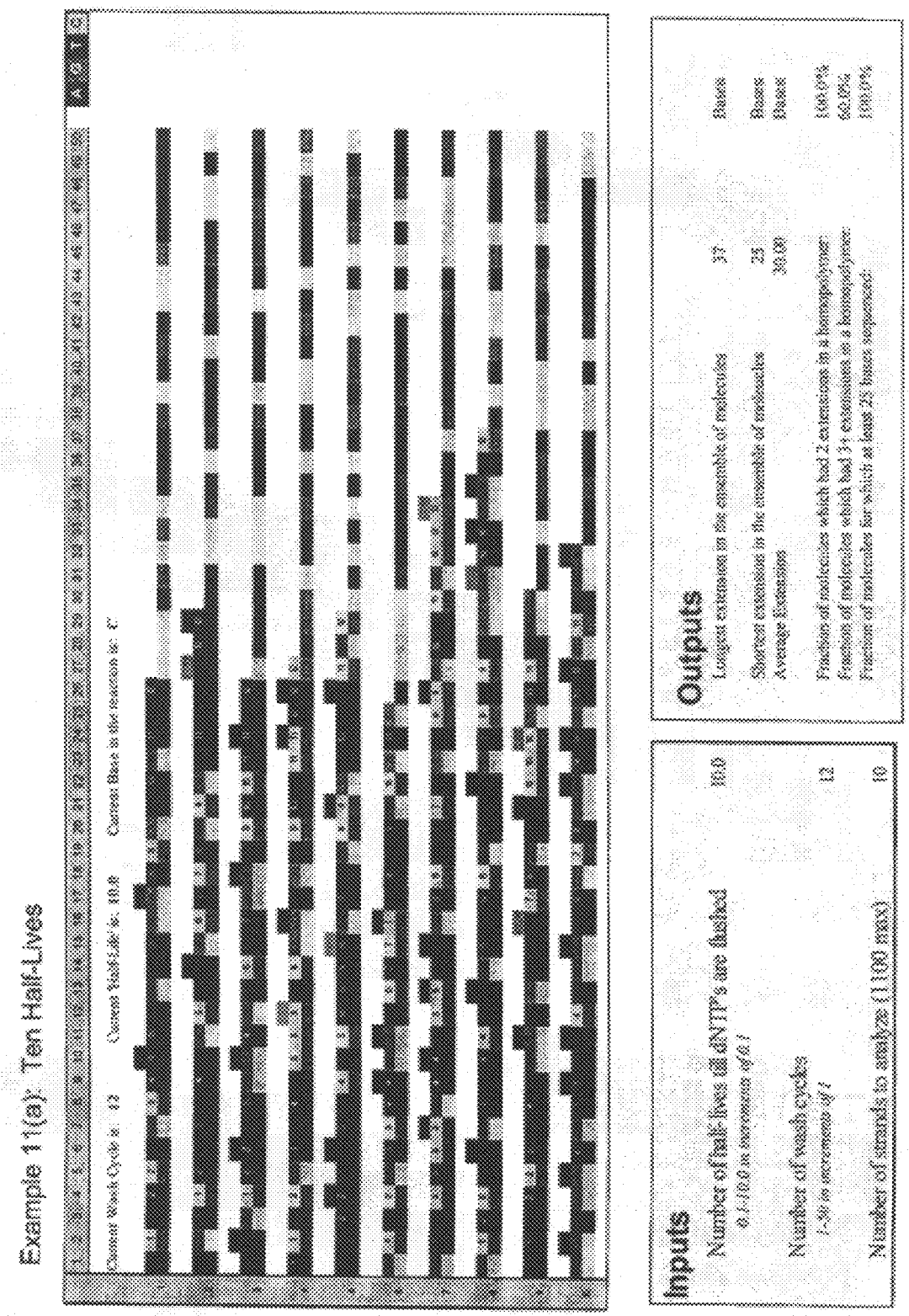
FIG. 19a illustrates the homopolymer issue using non-short cycle sequencing in analyzing 10 target polynucleotides in a stimulated synthesis of their complementary strands using cycle periods of 10 half lives and repeating the cycles 12 times.
Figure 19B:
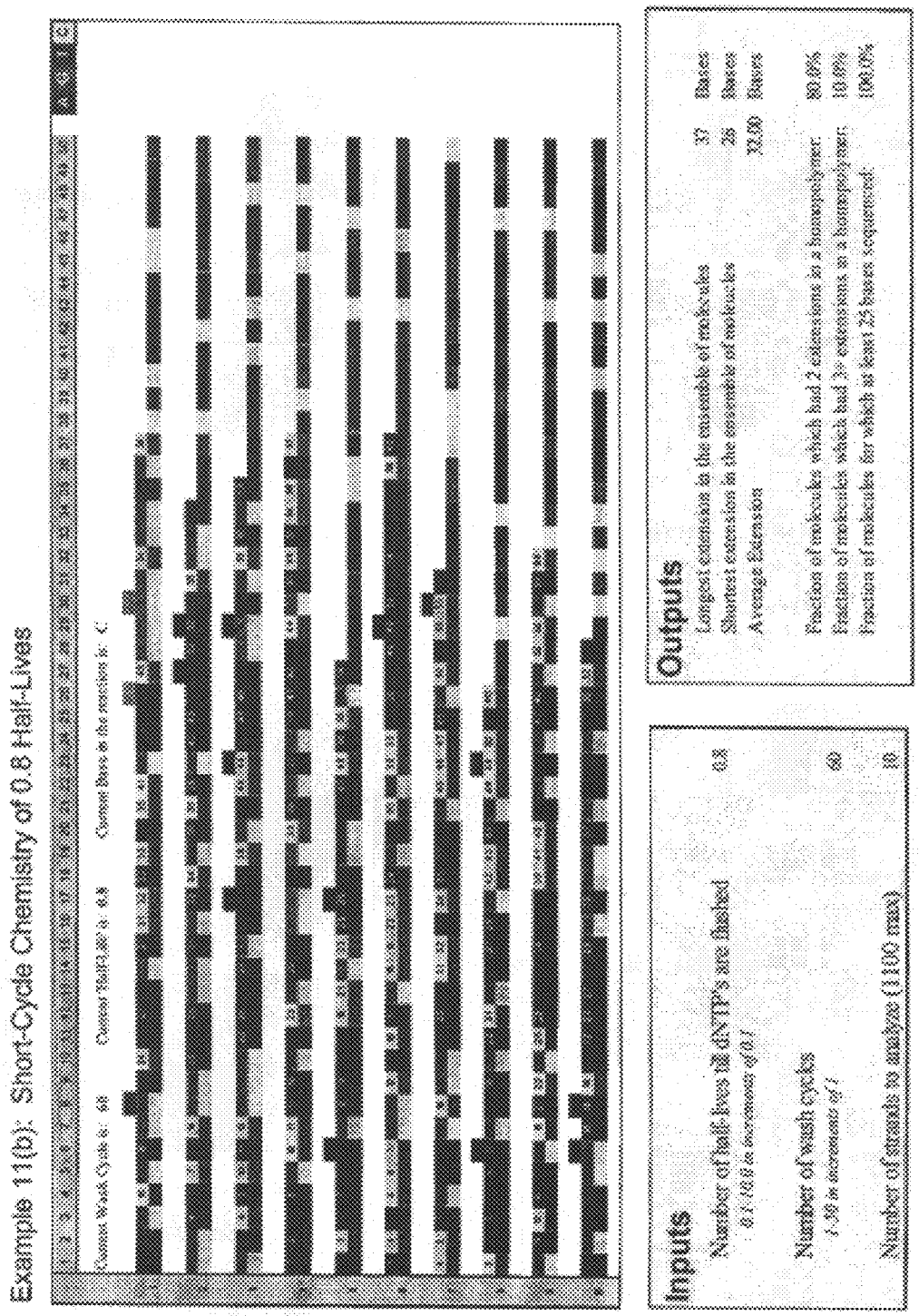
FIG. 19b illustrates a short cycle embodiment for analyzing 10 target polynucleotides by simulating the synthesis of their complementary strands using short-cycle periods of 0.8 half life periods and repeating the cycles 60 times.

FIG. 19 illustrates the advantage of short-cycle sequencing with respect to avoiding long homopolymer reads. FIG. 19a illustrates a simulated analysis of 10 target polynucleotides using non-short-cycle sequencing (Example 11a), whereas FIG. 19b illustrates a simulated analysis of the same number of target polynucleotides using short-cycle sequencing (Example 11b).

The simulations were performed as follows: an Excel spreadsheet was opened and "Customize . . . " selected from the "Tools" menu of the Excel toolbar. The "Commands" tab was selected and, after scrolling down, "Macros" was clicked. The "smiley face" that appeared in the right panel was dragged to the toolbars on top of the spreadsheet. The "Customize" box was closed and the "smiley face" clicked once. From the list of subroutines that appeared, "ThisWorkbook. Main_Line." was selected. The program was run by clicking again on the "smiley face."

Input values were then entered into the tabbed sheet called "In Out." There were three input values:

The first input value corresponded to the period of time allowed for incorporation reactions of provided nucleotides into the growing complementary strands of the polynucleotides to be analyzed. This period was conveniently measured in half lives of the incorporation reaction itself. Each cycle of incorporation was simulatedly halted after a period of time, representing, for example, the time when unincorporated nucleotides would be flushed out or the incorporation reactions otherwise halted.

The second input value corresponds to the number of times each cycle of incorporation was repeated. That is, the number of times the steps of providing nucleotides, allowing incorporation reactions into the complementary strands in the presence of polymerizing agent, and then halting the incorporations are repeated. The nucleotides were simulatedly provided as a wash of each of dATPs, dGTPs, dTTPs, and dCTPs. The program then recorded which nucleotides were incorporated, corresponding to a detection step of detecting incorporation.

The third input value corresponds to number of strands of target polynucleotides to by analyzed in the simulation. The program allowed up to 1100 target polynucleotide molecules to be analyzed in a given simulation.

After the program was started, as described above, the program first generated the inputed number of strands composed of random sequences. The program then simulated hybridization and polymerization of the correct base of each incorporation reaction, based on the generated sequence of the target polynucleotide templates. The program continued these simulated reactions for the allowed amount of simulated time, determined by the inputed number of half lives. Statistics of the simulation were then computed and reported, including the longest strand, the shortest strand, and the average length of all strands, as well as the fraction of strands extended by at least 25 nucleotide incorporations, as discussed in more detail below.

In the first part of this simulation, Example 11a, the input values used were a cycle period of 10 half lives, 12 repeats of the cycle, and 10 target polynucleotide strands.

FIG. 19a illustrates the results obtained. Homopolymers stretches which occured in the same simulated complementary strand are highlighted in magenta wherever 2 nucleotides of the same base type were incorporated in a row, and in cyan wherever more than two nucleotides of the same base type were incorporated in a row.

FIG. 19a illustrates that the output values included the longest extended complementary strand obtained during the simulation (Longest extension in the ensemble of molecules); the shorted extended complementary strand obtained during the simulation (Shortest extension in the ensemble of molecules); and the average extension. These numbers represent the greatest number of incorporations into any of the 10 simulatedly growing complementary strands, the smallest number of incorporations for any of the 10, and the average number of incorporations for the 10. FIG. 19a indicates that the values obtained for Example 11a were 37 incorporations in the longest extension, 25 in the shortest, and 30.00 as the average number of incorporations.

The output values also provided information on the number of incorporations that occurred in each of growing complementary strands during each cycle period of the simulation. For example, FIG. 19a indicates that for the input values of Example 11a, the percentage of growing stands extended by two or more nucleotides in a homopolymer stretch was 100.0%; and the percentage of growing strands extended by three or more nucleotides in a homopolymer stretch was 60.0%. That is, using a cycle period of 10 half lives resulted in only 40% of the complementary strands being extended by two or less nucleotides in a homopolymer stretch per cycle of incorporation.

Further, output values also indicated the total number of incorporations for each of the growing strands for the total number of repeated cycles. This represents the length of the sequence of target polynucleotide analyzed. FIG. 19a illustrates that in Example 11a, 100.0% of the 10 target polynucleotides of the simulation were extended by at least 25 incorporated nucleotides. This illustrates that using a cycle period of 10 half lives, and repeating the cycles 12 times, allowed analysis of a 25 base sequence of 10 target polynucleotides.

In the second part of this simulation, Example 11b, the input values used were a cycle period of 0.8 half lives, 60 repeats of the cycle, and 10 target polynucleotide strands.

FIG. 19b illustrates the results obtained. Homopolymers stretches which occurred in the same simulated complementary strand are highlighted in magenta wherever 2 nucleotides of the same base type were incorporated in a row, and in cyan wherever more than two nucleotides of the same base type were incorporated in a row.

FIG. 19b illustrates that the output values included the longest extended complementary strand obtained during the simulation (Longest extension in the ensemble of molecules); the shorted extended complementary strand obtained during the simulation (Shortest extension in the ensemble of molecules); and the average extension. These numbers represent the greatest number of incorporations into any of the 10 simulatedly growing complementary strands, the smallest number of incorporations for any of the 10, and the average number of incorporations for the 10. FIG. 19b indicates that the values obtained for Example 11b were 37 incorporations in the longest extension, 26 in the shortest, and 32.00 as the average number of incorporations.

The output values also provided information on the number of incorporations that occurred in each of growing complementary strands during each cycle period of the simulation. For example, FIG. 19b indicates that for the input values of Example 11b, the percentage of growing stands extended by two or more nucleotides in a homopolymer stretch was 80.0%; and the percentage of growing strands extended by three or more nucleotides in a homopolymer stretch was 10.0%. That is, using a cycle period of 0.8 half lives resulted in 90% of the complementary strands being extended by two or less nucleotides per cycle of incorporation.

Output values also indicated the total number of incorporations for each of the growing strands for the total number of repeated cycles. As in Example 11a, this represents the length of the sequence of target polynucleotide analyzed. FIG. 19b illustrates that in Example 11b, 100.0% of the 10 target polynucleotides of the simulation were again extended by at least 25 incorporated nucleotides. This illustrates that using a cycle period of 0.8 half lives, and repeating the cycles 60 times, allowed analysis of a 25 base sequence of 10 target polynucleotides.

Comparing the two simulations, it will be appreciated by those in the art that the use of short-cycles of sequencing overcame issues of reading long repeats of homopolymer stretches in sequencing by synthesis, without using blocking moieties, as only a few nucleotides were incorporated per cycle. Comparing Examples 11a and 11b, the long cycles in 11a resulted in 40% of the extended complementary strands having two or less homopolymer nucleotide incorporations per cycle. Conversely, the short cycles in 11b resulted in 90% of the extended complementary strands having two or less homopolymer nucleotide incorporations per cycle, facilitating quantification. That is, as explained more thoroughly above, shorter reads can be quantitated to determine the number of nucleotides incorporated, for example, where the nucleotides are of the same base type and bear the same labeling moiety. That is, methods known in the art can correlate increases in the signal intensity from the same labeling moieties to determine the number of incorporated nucleotides when the number is relatively small. For example, imaging systems known in the art can reliably distinguish the difference between one versus two fluorescent labeling moieties on consecutively-incorporated nucleotides, and/or two versus three fluorescent labeling moieties on consecutively-incorporated nucleotides. Moreover, signals from the incorporated nucleotides can be reduced, e.g., by bleaching or removal of the signal generating moiety of the labeling moiety, before carrying out the next cycle of incorporations or after the number of cycles resulting in too large numbers of incorporated nucleotides (that is, numbers too high to be accurately quantitated based on increasing signal intensity).

Comparing Examples 11a and 11b also indicated that a greater number of repeated cycles were needed to analyze a given length of sequence when using shorter cycles. That is, the 10 half life cycle was repeated 12 times to result in 100.0% of the 10 complementary strands being extended by at least 25 nucleotides, whereas the 0.8 half life cycle was repeated 60 times to obtain this same result and thereby analyze the 25 nucleotides sequence.

Nonetheless, many aspects of the repeated cycles may be automated, for example, using microfluidics for washing nucleotides to sites of anchored target polynucleotides, and washing out unincorporated nucleotides to halt each cycle.

Example 12

FIG. 20 illustrates yet another simulated analysis of a number of target polynucleotides using short-cycle sequencing. The simulation was run using the program described in Examples 11a and 11b but using a larger number of target polynucleotides.

That is, in this simulation, the input values used were a cycle period of 0.8 half lives, 60 repeats of the cycle, and 200 target polynucleotide strands.

FIG. 20 illustrates the results obtained. Homopolymers stretches which occured in the same simulated complementary strand are highlighted in magenta wherever 2 nucleotides of the same base type were incorporated in a row, and in cyan wherever more than two nucleotides of the same base type were incorporated in a row.

The output values obtained were 48 incorporations in the longest extended complementary strand, 20 in the shortest, and 32.00 as the average number of incorporations for the 200 stimulatedly extended complementary strands.

Further, the percentage of growing stands extended by two or more nucleotides in a homopolymer stretch was 78.5%; and the percentage of growing strands extended by three or more nucleotides in a homopolymer stretch was 4.0%. That is, using a cycle period of 0.8 half lives resulted in 96.0% of the complementary strands being extended by two or less nucleotides in a homopolymer stretch per cycle of incorporation. Moreover, 95.5% of the 200 target polynucleotides of the simulation were extended by at least 25 incorporated nucleotides, while 100% were extended by at least 20 nucleotides. This illustrated that using a cycle period of 0.8 half lives, and repeating the cycles 60 times, allows analysis of a 20 base sequence of 200 target polynucleotides.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of increasing accuracy of nucleic acid sequencing, the method comprising the steps of:

a) exposing a duplex comprising a template and a primer to a polymerase and one or more nucleotides comprising a detectable label under conditions sufficient for template-dependent nucleotide addition to said primer, the primer being hybridized to a first region of the template, wherein said duplex is individually optically resolvable;

b) identifying nucleotide incorporated into said primer;

c) repeating steps a) and b), thereby determining a nucleotide sequence;

d) removing the primer from the template;

e) exposing the template to a second primer capable of hybridizing to the first region of the template to form a template/primer duplex, and repeating steps a) through c) to resequence a portion of the template, thereby increasing the accuracy of nucleic acid sequencing.

2. The method of claim 1, wherein the sequence obtained in c) is compared with the sequence obtained in e).

3. The method of claim 1, wherein the first and second primers have identical sequence.

4. The method of claim 1, wherein the first and second primers have different sequences.

5. The method of claim 1, further comprising the step of removing the primer from the template and repeating step (e) at least once.

6. The method of claim 1, wherein said label is an optically-detectable label.

7. The method of claim 6, wherein said optically-detectable label is a fluorescent label.

8. The method of claim 7, wherein said fluorescent label is selected from the group consisting of fluorescein, rhodamine, cyanine, Cy5, Cy3, BODIPY, alexa, and derivatives thereof.

9. The method of claim 1, wherein said duplex is attached to a surface.

10. The method of claim 1, wherein a plurality of primers is hybridized to a plurality of regions on said template.

11. The method of claim 10, wherein a plurality of regions are sequenced.

12. The method of claim 11, wherein a plurality of regions are resequenced.

13. A method of increasing accuracy of nucleic acid sequencing, the method comprising the steps of:
   a) exposing a duplex comprising a template and a plurality of primers to a polymerase and one or more nucleotide comprising a detectable label under conditions sufficient for template-dependent nucleotide addition to at least one of said plurality of primers, the plurality of primers being hybridized to a plurality of regions of the template, wherein said duplex is individually optically resolvable;
   b) identifying incorporated nucleotides;
   c) repeating steps a) and b), thereby determining a nucleotide sequence of at least one of said plurality of regions of the template;
   d) removing at least one of said plurality of primers from the template;
   e) exposing the template to a second plurality of primers capable of hybridizing to a first region of the template to form a template/primer duplex, and repeating steps a) and c) to resequence the at least one of said plurality of regions of the template, thereby increasing the accuracy of nucleic acid sequencing.

14. The method of claim 13, wherein sequence obtained in c) is compared with sequence obtained in e).

15. The method of claim 13, wherein the first and second pluralities of primers have identical sequences.

16. The method of claim 13, wherein the first and second pluralities of primers have different sequences.

17. The method of claim 13, wherein each of the plurality of primers is removed in step d).

18. The method of claim 13, further comprising the step of removing at least one primer from the template and repeating step e) at least once.

19. The method of claim 13, wherein said label is an optically-detectable label.

20. The method of claim 19, wherein said optically-detectable label is a fluorescent label.

21. The method of claim 20, wherein said fluorescent label is selected from the group consisting of fluorescein, rhodamine, cyanine, Cy5, Cy3, BODIPY, alexa, and derivatives thereof.

22. The method of claim 13, wherein said duplex is attached to a surface.

* * * * *

```
                          SEQUENCE LISTING

<160> NUMBER OF SEQ ID NOS: 13

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcagtcatca gtcatcagtc atcagtcatc agtcatcagt catcagtcat cagtcatcag      60
tcatcagtca tcagtcatca gtcatcacac ggaggttcta                           100

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tagaacctcc gtgt                                                        14

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctccagcgtg ttttatctct gcgagcataa tgcctgcgtc atccgccagc                 50

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctggcggat gac                                                         13

<210> SEQ ID NO 5
<211> LENGTH: 100
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 5
tttgcttctt attctttgct tcttattctt tgcttcttat tctttgcttc ttattctttg    60
cttcttattc tttgcttctt attcttacac ggaggttcta                         100

<210> SEQ ID NO 6
<211> LENGTH: 78
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 6
ccattttttg cccccccattt tttgccccccc attttttgcc cccattttttt gccccccatt    60 ttttacacgg aggttcta                                                  78

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 7
gcccccattt tttt                                                      14

<210> SEQ ID NO 8
<211> LENGTH: 14
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 8
aaaaaauggg gggc                                                      14

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 9
attctttgct tcttattctt tgcttcttat tctttg                              36

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 10
aaaaaaaaaa a                                                         11

<210> SEQ ID NO 11
<211> LENGTH: 19
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (16)
<223> OTHER INFORMATION: Unknown base

<400> SEQUENCE: 11
gtcatcagtc atcacncgg                                                    19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (14)
<223> OTHER INFORMATION: Unknown base
<220> FEATURE:
<221> NAME/KEY: misc_feature
<222> LOCATION: (16)
<223> OTHER INFORMATION: Unknown base
<220> FEATURE:
<221> NAME/KEY: misc_feature
<222> LOCATION: (18)..(20)
<223> OTHER INFORMATION: Unknown base

<400> SEQUENCE: 12
gtcatcagtc atcncncnnn                                                   20

<210> SEQ ID NO 13
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: Unknown base
<220> FEATURE:
<221> NAME/KEY: misc_feature
<222> LOCATION: (5)
<223> OTHER INFORMATION: Unknown base
<220> FEATURE:
<221> NAME/KEY: misc_feature
<222> LOCATION: (7)
<223> OTHER INFORMATION: Unknown base

<400> SEQUENCE: 13
nccgngngau gacu                                                         14
```